US012637486B2

(12) United States Patent
Lieberman et al.

(10) Patent No.: US 12,637,486 B2
(45) Date of Patent: May 26, 2026

(54) LIGANDS FOR NANO-SIZED MATERIALS

(71) Applicant: SAMSUNG ELECTRONICS CO., LTD., Suwon-si (KR)

(72) Inventors: Itai Lieberman, Oud-Heverlee (BE); Manuel Hamburger, Mannheim (DE); Christian Matuschek, Frankfurt am Main (DE); Thomas Eberle, Landau (DE); Beate Burkhart, Darmstadt (DE); Sebastian Meyer, Frankfurt am Main (DE)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 1104 days.

(21) Appl. No.: 17/436,189

(22) PCT Filed: Mar. 2, 2020

(86) PCT No.: PCT/EP2020/055424

§ 371 (c)(1),
(2) Date: Sep. 3, 2021

(87) PCT Pub. No.: WO2020/178230

PCT Pub. Date: Sep. 10, 2020

(65) Prior Publication Data

US 2022/0127286 A1 Apr. 28, 2022

(30) Foreign Application Priority Data

Mar. 4, 2019 (EP) .................................... 19160606

(51) Int. Cl.

| | |
|---|---|
| ***C07F 9/38*** | (2006.01) |
| ***B82Y 20/00*** | (2011.01) |
| ***B82Y 40/00*** | (2011.01) |
| ***C01B 19/00*** | (2006.01) |
| ***C07C 323/22*** | (2006.01) |
| ***C07D 251/24*** | (2006.01) |
| ***H10K 50/11*** | (2023.01) |
| ***H10K 50/115*** | (2023.01) |
| ***H10K 50/12*** | (2023.01) |
| ***H10K 85/60*** | (2023.01) |

(52) U.S. Cl.

CPC .......... *C07F 9/3882* (2013.01); *C01B 19/007* (2013.01); *C07C 323/22* (2013.01); *C07D 251/24* (2013.01); *H10K 50/11* (2023.02); *H10K 85/633* (2023.02); *H10K 85/654* (2023.02); *B82Y 20/00* (2013.01); *B82Y 40/00* (2013.01); *H10K 50/115* (2023.02); *H10K 50/121* (2023.02)

(58) Field of Classification Search

CPC .. H10K 50/115; H10K 85/633; H10K 85/649; H10K 85/654; H10K 85/6572; H10K 85/6574; H10K 85/6576; C07F 9/3882; C01B 19/007; C07C 323/22; C07D 251/24

See application file for complete search history.

(56) References Cited

U.S. PATENT DOCUMENTS

| | | | | |
|---|---|---|---|---|
| 5,326,905 | A | 7/1994 | Dow et al. | |
| 7,700,200 | B2 | 4/2010 | Bulović et al. | |
| 8,120,010 | B2 | 2/2012 | Cho et al. | |
| 10,054,834 | B2 | 8/2018 | Shinoda et al. | |
| 2008/0206565 | A1* | 8/2008 | Takahashi .............. | B82Y 30/00 106/31.13 |
| 2010/0237323 | A1* | 9/2010 | Akai .................... | C09K 11/565 257/13 |
| 2013/0146854 | A1* | 6/2013 | Dong ..................... | H10K 50/12 438/45 |
| 2015/0083970 | A1 | 3/2015 | Koh et al. | |
| 2017/0306227 | A1 | 10/2017 | Ippen et al. | |
| 2017/0349824 | A1 | 12/2017 | Kan | |
| 2018/0119007 | A1 | 5/2018 | Ippen et al. | |
| 2022/0010203 | A1* | 1/2022 | Stubbs ................. | C09K 11/883 |

FOREIGN PATENT DOCUMENTS

| | | | | |
|---|---|---|---|---|
| DE | 102012203036 | A1 | 8/2013 | |
| EP | 3182197 | B1 | 5/2018 | |
| JP | 2008089705 | A | 4/2008 | |
| JP | 2011133805 | A | 7/2011 | |
| JP | 2013195710 | A | 9/2013 | |
| JP | 2018037534 | A | 3/2018 | |
| JP | 2018530777 | A | 10/2018 | |
| WO | 9115495 | A1 | 10/1991 | |
| WO | WO-2012013272 | A1 * | 2/2012 | ......... H01L 51/0035 |

OTHER PUBLICATIONS

Karabuga et al., "Efficient transfer hydrogenation reactions with quinazoline-based ruthenium complexes" Tetrahedron Letters (2015) vol. 56, pp. 101-104. (Year: 2015).*

Namhun Kim et al: Color temperature control of quantum dot white light emitting diodes by grafting organic fluorescent molecules, Journal of Materials Chemistry C, vol. 2, No. 46, Jan. 1, 2014, 9800-9804.

Huaping Zhu et al: Synthesis and Optical Properties of Thiol Functionalized CdSe/ZnS (Core/Shell) Quantum Dots by Lingand Exchange, Journal of Nanomaterials, 100, 4, 2014, 3297-3314.

Raquel Gomes, Binding of Phosphonic Acids to CdSe Quantum Dots: A Solution NMR Study, Journal of Physical Chemistry Letters, 2, 7, 2011, 145-152.

Nathan De Roo et al: "Synthesis of Phosphonic Acid Ligands for Nanocrystal Surface Functionalization and Solution Processed Memristors", Chemistry of Materials, vol. 30, No. 21, Nov. 13, 2018 (Nov. 13, 2018), pp. 8034-8039, XP055696756, ISSN: 0897-4756, DOI: 10.1021/acs.chemmater.8b03768.

(Continued)

*Primary Examiner* — Dylan C Kershner

(74) *Attorney, Agent, or Firm* — Sughrue Mion, PLLC

(57) ABSTRACT

The present invention relates to a compound suitable as ligand for binding to the surface of a semiconductor nanoparticle, said compound comprising an anchor group, a linker group and an organic functional group; a semiconductor nanoparticle have said ligand attached to the outermost particle surface; a composition, a formulation and a process for the preparation of said semiconductor nanoparticle; and an electronic device.

17 Claims, No Drawings

(56) References Cited

OTHER PUBLICATIONS

Lihua Dong et al: "Theoretical studies on the interaction of biphenyl inhibitors withprotein tyrosine phosphatase MptpB", Journal of Molecular Modeling, Springer, DE, vol. 18, No. 8, Mar. 11, 2012 (Mar. 11, 2012), pp. 3847-3856, XP035091304, ISSN: 0948-5023, DOI: 10.1007/S00894-012-1384-5.
International Search Report PCT/EP2020/055424 dated Apr. 6, 2020 (pp. 1-12).
European Search Report dated Jun. 24, 2022 issued in corresponding application 20707106.9.
Bruun Leif et al: "Characterization of monoclonal antibodies raised against different structures belonging to the s-triazine group of herbicides", Analytica Chimica Acta, vol. 436, No. 1, Jun. 1, 2001, pp. 87-101.
Abraham Ffion et al: Supporting Information for the article "Surface Energy and Work Function Control of AlOx/Al Surfaces by Fluorinated Benzylphosphonic Acids", ACS Applied Materials & Interfaces, 2016, 8(18), p. 11857-11867.
Communication dated Apr. 30, 2025 issued by the China National Intellectual Property Administration in Chinese Patent Application No. 202080018271.3.

* cited by examiner

LIGANDS FOR NANO-SIZED MATERIALS

The present invention relates to a compound suitable as ligand for binding to the surface of a semiconductor nanoparticle; a semiconductor nanoparticle have said ligand attached to the outermost particle surface; a composition, a formulation and a process for the preparation of said semiconductor nanoparticle; and an electronic device.

Electronic devices in the context of this application are understood to mean what are called “organic electronic devices”, which contain organic semiconductor materials as functional materials. More particularly, these devices are understood to mean organic electroluminescent (EL) devices, especially organic light emitting diodes (OLEDs).

Soluble organic semiconductors have been thoroughly investigated for their potential use in electronic devices. In particular, they are of much interest for solar cells and OLEDs. The advantage of using soluble molecules (small molecules or polymers) is that inkjet printing technique can be used for the preparation of devices. Regarding these inks, the challenge remains to find a suitable solvent or solvent mixture, rapidly solubilizing the organic semiconductor materials and having a suitable viscosity, surface tension and boiling point to achieve a homogeneous film formation when using deposition by inkjet printing.

Semiconductor nanocrystals (NCs) have attracted great interest due to the ability to tailor their absorption and emission over a wide spectral range, by changing their size, shape and composition, thereby replacing the fluorescent organic molecules or phosphorescent metal complexes commonly employed in OLEDs to tune the emission color. In particular, group II-VI and group III-V semiconductor NCs are of importance due to their fluorescence, covering the visible to the near infrared (NIR) spectrum, which is appealing for a variety of technological applications.

Semiconductor NCs are usually covered with a layer of organic molecules which act as ligands. These ligands function to passivate the surface of the semiconductor nanocrystal and render it soluble in different media. Common ligands, as for example disclosed in U.S. Pat. No. 7,700,200 B2, are made of a polar anchor group, which binds to the semiconductor nanocrystal surface, and a hydrocarbon group pointing out of the surface. According to U.S. Pat. No. 8,120,010 B2, the ligand may additionally contain a functional group selected from acid groups and highly electronegative electron withdrawing groups.

However, these hydrocarbon group are insulators, which do not allow for an efficient charge transport within the emissive layer (EML) and into the quantum material.

Thus, it is an object of the present invention to provide compounds which are suitable as ligands for binding to the surface of semiconducting nanoparticles, which allow passivation of the nanocrystal surface and solubility in solution, ensure an improved surface binding process and increased ligand density on the surface and which enable improved charge transport through the layer and into the quantum material, thereby improving the overall performance of an electronic device.

It is furthermore an object of the present invention to provide a semiconductor nanocrystal which has a high fluorescent quantum yield, can realize a high contrast, can improve charge transport into the semiconductor nanocrystal and within the semiconductor nanocrystal layer, and by doing so, can improve the efficiency of an electronic device, in particular an electroluminescent device.

The present invention provides novel compounds suitable as ligand for binding to the outermost surface of a semiconductor nanoparticle in order to achieve the technical object(s) described above.

The invention thus relates to a compound comprising in the given order an anchor group, AG, being capable of binding to the surface of a semiconductor nanoparticle, followed by an electronically inert and conjugating interrupting linker group, L, followed by an organic functional group, FG, and wherein the compound has a molecular weight of 1000 g/mol or less.

As used herein, the term “anchor group” denotes an organic functional group which is capable of interacting with the surface of a semiconductor nanoparticle, thereby binding the compound of the present invention to the semiconductor nanoparticle surface, for example via covalent bonding or ionic bonding, or dipole-dipole interaction, without being limited thereto.

Preferably, the anchor group, AG, is selected from the group consisting of thiols or salts thereof, phosphonic acids or salts thereof, carboxylic acids or salts thereof, selenols or salts thereof, sulfinic acids or salts thereof, mercaptoesters or salts thereof, carbodithioic acids or salts thereof, boronic acids or salts thereof, amines and phosphines; more preferably from the group consisting of thiols or salts thereof, phosphonic acids or salts thereof, carboxylic acids or salts thereof, boronic acids or salts thereof, and mercaptoesters or salts thereof, and most preferably the anchor group, AG, is selected from thiols or salts thereof, from phosphonic acids or salts thereof, or from mercaptoacetates or salts thereof.

Further, the compound according to the invention includes a linker group, L, which is a divalent group that interconnects the anchor group, AG, and the organic functional group, FG, via chemical bonding, and which is electronically inert and conjugating interrupting. As used herein, the term “conjugating interrupting” means that the linker group, L, is an organic group that comprises at least one structural unit which interrupts conjugation, i.e., the overlap of one p orbital with another across an intervening σ bond, within a conjugated system, i.e., a system of connected overlapping p orbitals with delocalized π-electrons in a molecule. For example, the linker group may contain in its main chain (backbone) at least one C atom with only σ bonds (i.e. 4 σ bonds), so that delocalization of π-electrons does not occur. The term “electronically inert” as used herein means the inability to transport charges from one end of the linker group to the other end of the linker group by any other transport mechanism than tunneling. Preferably, an electronically inert group as used herein may have a band gap equal to or larger than 3 eV, more preferably equal to or larger than 3.5 eV, even more preferably equal to or larger than 4 eV, particularly preferably equal to or larger than 5 eV, and most preferably equal to or larger than 6 eV, wherein the term “band gap” means the energy gap between the highest occupied molecular orbital (HOMO) and the lowest unoccupied molecular orbital (LUMO).

Preferably, the linker group, L, is selected from the group consisting of a straight-chain alkylene group having 1 to 20 C atoms, or a cyclic or branched alkylene group having 3 to 20 C atoms, wherein one or more non adjacent methylene groups may be replaced by —O—, —S—, —C(═O)O—, —C(═S)S—, aromatic rings or heteroaromatic rings.

The aromatic and heteroaromatic rings are preferably simple aromatic and heteroaromatic rings, more preferably 5- or 6-membered aromatic and heteroaromatic rings, respectively. The simple heteroaromatic rings comprise at least one heteroatom in the aromatic ring, preferably one or two heteroatoms, preferably a heteroatom selected from N, O and S.

Further, the compound according to the invention includes an organic functional group, FG, connected to the linker group, L. The organic functional group, FG, is preferably selected from the group consisting of aromatic ring systems having 6 to 60 aromatic ring atoms or heteroaromatic ring systems having 5 to 60 aromatic ring atoms, both of which may optionally be further substituted, for example by a group $R^1$ or $R^4$ as defined below. Preferred examples of aromatic or heteroaromatic ring systems as the group FG are selected from biphenyls, terphenyls, quaterphenyls, fluorenes, spirobifluorenes, dihydrophenanthrenes, dihydropyrenes, tetrahydropyrenes, indenofluorenes, truxenes, isotruxenes, spirotruxenes, spiroisotruxenes, and indenocarbazoles. Particularly preferred examples of the group FG are selected from biphenyls, terphenyls, quaterphenyls, or fluorenes, even more preferably from biphenyls.

Very preferred examples of ring systems suitable as groups FG are selected from the following aromatic groups:

(FG-1)

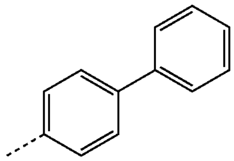

(FG-2)

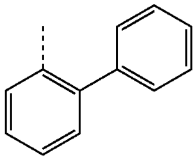

(FG-3)

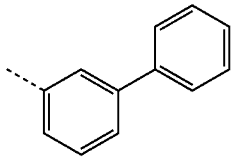

(FG-4)

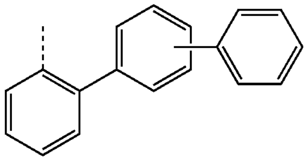

(FG-5)

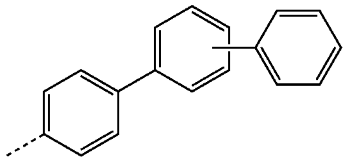

(FG-6)

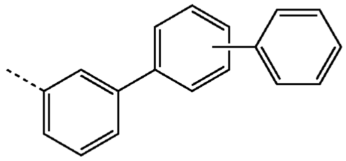

-continued (FG-7)

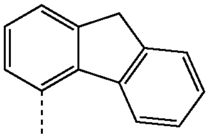

(FG-8)

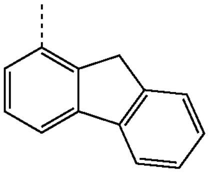

(FG-9)

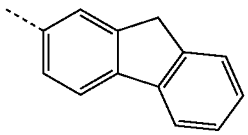

(FG-10)

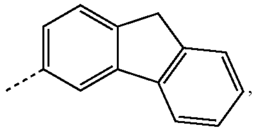

wherein the dashed line represents the bonding position to the linker group, L and wherein the groups can be further substituted by one or more groups $R^1$. $R^1$ is defined below.

The compound according to the present invention is preferably a small molecule. The term "small molecule" as used herein means a compound that has a molecular weight of less than 2000 g/mol. Preferably, the compound according to the present invention has a molecular weight of 1000 g/mol or less. More preferably, it has a molecular weight of 900 g/mol or less, even more preferably 800 g/mol or less, still even more preferably 700 g/mol or less, and particularly preferably 600 g/mol or less. For example, the compound of the invention has a molecular weight of 100 g/mol to 1000 g/mol, or from 100 g/mol to 900 g/mol, or from 100 g/mol to 800 g/mol, or from 100 g/mol to 700 g/mol, or from 100 g/mol to 600 g/mol.

The small molecules of the present invention can be prepared and processed easily. Particularly the preparation of the compounds and the preparation of quantum materials bearing the ligands is very simple. The processes are suitable for commercial production (mass production) of the ligand and the quantum material. Furthermore, fine tuning of the ligands can be accomplished easily and customization of the quantum material comprising the ligand is convenient. Small molecules enable fine tuning of the surface chemistry of the quantum dots. Concentration of the small molecules can be controlled easily, allowing mixtures of different kinds of ligands on the quantum dot surface. Furthermore, the small molecules are easily dissolvable in various commonly used organic solvents, allowing easy processability. Polymeric materials typically do not provide these advantages. Thus, the small molecules and the quantum materials of the instant invention are suitable for mass production.

More preferably, the organic functional group, FG, is selected from the group consisting of electron injecting groups, electron transporting groups, hole blocking groups, n-dopant-groups, host-groups, matrix groups, wide band gap groups, fluorescent emitter groups, delayed fluorescent groups, phosphorescent groups, electron blocking groups, hole transport groups, hole injecting groups or p-dopant groups.

Particularly preferably, the organic functional group, FG, exhibits a rather large energy gap $\Delta E_{ST}$ between their singlet energy ($S_1$) and triplet energy ($T_1$). The energy gap of FG is preferably larger than the energy gaps disclosed below for the delayed fluorescent materials, i.e. it is preferably larger than 0.2 eV, very preferably larger than 0.3 eV, particularly preferably larger than 0.5 eV.

Very preferably the FG is selected from the above-mentioned groups, but not a delayed fluorescent group, wherein the above-mentioned preferences for $\Delta E_{ST}$ apply.

Even more preferably, the organic functional group, FG, is an electron transporting or hole transporting group, but particularly not a delayed fluorescent group, i.e. the electron transporting group and the hole transporting group exhibit a rather large energy gap $\Delta E_{ST}$ between their singlet energy ($S_1$) and triplet energy ($T_1$). The energy gap of the electron and hole transporting group is preferably larger than the energy gaps disclosed below for the delayed fluorescent materials, i.e. it is preferably larger than 0.2 eV, very preferably larger than 0.3 eV, particularly preferably larger than 0.5 eV.

Having a larger $\Delta E_{ST}$ results in improved performance data of electroluminescent devices, such as efficiencies, voltages, lifetimes, color (e.g. purity or gamut).

Species of these groups are well known in the prior art. In general, all species of these groups as used in accordance with the prior art and as are known to a person skilled in the art in the field of organic electroluminescent devices are suitable and can be used as the organic functional group, FG.

Preferred wide band gap groups can be derived from the material as disclosed in U.S. Pat. No. 7,294,849, which is characterized in having a band gap of at least 3.5 eV. Thus, in a preferred embodiment the wide band gap material is a material having a band gap (i.e. a difference between the LUMO and HOMO energy level, wherein LUMO and HOMO are defined as being the lowest unoccupied molecular orbital and the highest occupied molecular orbital, respectively) of 3.0 eV or more, preferably 3.2 eV or more, very preferably 3.5 eV or more, particularly preferably 3.7 eV or more and very particularly preferably 4.0 eV or more.

It is preferred if the wide band gap material is a purely organic compound, i.e. an organic compound without any metals or metal ions. It is very preferred if the purely organic compound is an aromatic or heteroaromatic compound. Particularly preferably the wide band gap material is a purely aromatic organic compound.

Preferred fluorescent emitter groups can be derived from the compounds described in the following. Preferred fluorescent groups are selected from the class of the arylamines.

An arylamine in the sense of this invention is taken to mean a compound which contains three substituted or unsubstituted aromatic or heteroaromatic ring systems bonded directly to the nitrogen. At least one of these aromatic or heteroaromatic ring systems is preferably a condensed ring system, particularly preferably having at least 14 aromatic ring atoms.

Preferred examples thereof are aromatic anthracenamines, aromatic anthracenediamines, aromatic pyrenamines, aromatic pyrenediamines, aromatic chrysenamines or aromatic chrysenediamines. An aromatic anthracenamine is taken to mean a compound in which one diarylamino group is bonded directly to an anthracene group, preferably in the 9-position. An aromatic anthracenediamine is taken to mean a compound in which two diarylamino groups are bonded directly to an anthracene group, preferably in the 9,10-position. Aromatic pyrenamines, pyrenediamines, chrysenamines and chrysenediamines are defined analogously thereto, where the diarylamino groups are preferably bonded to the pyrene in the 1-position or in the 1,6-position. Further preferred fluorescent emitters are indenofluorenamines or indenofluorenediamines, for example in accordance with WO 2006/108497 or WO 2006/122630, benzoindenofluorenamines or benzoindenofluorenediamines, for example in accordance with WO 2008/006449, and dibenzoindenofluorenamines or dibenzoindeno-fluorenediamines, for example in accordance with WO 2007/140847, and the indenofluorene derivatives containing condensed aryl groups which are disclosed in WO 2010/012328. Still further preferred fluorescent emitters are benzanthracene derivatives as disclosed in WO 2015/158409, anthracene derivatives as disclosed in WO 2017/036573, fluorene dimers like in WO 2016/150544 or phenoxazine derivatives as disclosed in WO 2017/028940 and WO 2017/028941. Preference is likewise given to the pyrenarylamines disclosed in WO 2012/048780 and WO 2013/185871. Preference is likewise given to the benzoindenofluorenamines disclosed in WO 2014/037077, the benzofluorenamines disclosed in WO 2014/106522 and the indenofluorenes disclosed in WO 2014/111269 or WO 2017/036574.

Preferably, the delayed fluorescent group is an e-type delayed fluorescent group, i.e. an eosin-type delayed fluorescent group, wherein the energy levels $S_1$ and $T_1$ of the delayed fluorescent group are close to each other to make thermally activated reverse intersystem crossing (RISC) from $T_1$ to $S_1$ possible.

One skilled in the art knows many compounds and groups that are suitable as being used for the purpose of the instant invention.

Preferred delayed fluorescent groups are disclosed in e.g. Tanaka et al., Chemistry of Materials 25(18), 3766 (2013), Ye Tao et al., Adv. Mater. 2014, 26, 7931-7958, Zhang et al., Nature Photonics advance online publication, 1 (2014), doi: 10.1038/nphoton.2014.12, Serevicius et al., Physical Chemistry Chemical Physics 15(38), 15850 (2013), Youn Lee et al., Applied Physics Letters 101(9), 093306 (2012), Nasu et al., ChemComm, 49, 10385 (2013), M. Y. Wong et al., Adv. Mater. 2017, 29, 1605444, Chem. Soc. Rev., 2017, 46, 915 and Nature Reviews Materials, 2018, Volume 3, Article Number 18020; Chem. Rec. 2018, 18, 1-14, WO 2011/070963, WO 2012/133188, WO 2015/022974, WO 2015/098975, WO 2013/154064, WO 2013/161437, WO 2013/081088 and WO 2013/011954.

Preferably the delayed fluorescent group is a purely organic (i.e. without metal or metal ion) group, very preferably an aromatic or heteroaromatic group. It is further preferred if the delayed fluorescent group which is an aromatic or heteroaromatic group, preferably an aromatic group, is substituted with one or more donor groups and with one or more acceptor groups.

One skilled in the art has no difficulty to identify groups having donor or acceptor properties.

A donor group is understood as being an electron donor group, i.e. a group having +I and/or +M effect. The determination of such parameters by using the Hammett equation is well known to one skilled in the art. Suitable and preferred donor groups are, e.g., diaryl- or heteroarylamino groups, carbazole or indeno- or indolocarbazole groups and derivatives thereof, which are preferably bonded via the nitrogen atom to the aromatic or heteroaromatic part of the group.

An acceptor group is understood as being an electron accepting group, i.e. a group having −I and/or −M effect. The determination of such parameters by using the Hammett equation is well known to one skilled in the art. Suitable and preferred acceptor groups are cyano groups, $CF_3$, ketones, preferably aromatic ketones, phosphinoxides and electron poor heteroaromatic groups such as triazines, pyridines, pyrimidines, pyrazines that can be further substituted.

Preferred phosphorescent groups are also well known to the skilled person and widely used in the field of organic electroluminescent devices.

A phosphorescent compound is a compound that emits light or irradiation, either through photoluminescence or electroluminescence, wherein the electronic transition represents a spin forbidden transition. Thus, the irradiation is based on a transition from an excited triplet or quintet state or from a mixed state having triplet or quintet character.

A phosphorescent compound (also called triplet emitter) preferably comprises an element having a high atomic number of at least 20 or more, very preferably larger than 38 and smaller than 84, particularly preferably larger than 56 and smaller than 80.

Preferably the phosphorescent group is an organometallic group, particularly preferably comprising a transition metal.

Very preferably, the phosphorescent group comprises copper, tungsten, rhenium, ruthenium, osmium, rhodium, iridium, palladium, platinum, silver, aurum or europium, particularly preferably copper, iridium and platinum.

Very particularly preferred phosphorescent organometallic complexes are disclosed in WO2015/091716 and WO00/70655, WO2001/41512, WO2002/02714, WO2002/15645, EP1191612, WO2005/033244, WO2005/019373, US2005/0258742, WO2006/056418, WO2007/115970, WO2007/115981, WO2008/000727, WO2009/050281, WO2009/050290, WO2011/051404, WO2011/073149, WO2012/121936, US2012/0305894, WO2012/170571, WO2012/170461, WO2012/170463, WO2006/121811, WO2007/095118, WO2008/156879, WO2008/156879, WO2010/068876, WO2011/106344, WO2012/172482, EP3126371, WO2015/014835, WO2015/014944, WO2016/020516, US2016/0072081, WO2010/086089, WO2011/044988, WO2014/008982, WO2014/023377, WO2014/094961, WO2010/069442, WO2012/163471, WO2013/020631, US2015/0243912, WO2008/000726, WO2010/015307, WO2010/054731, WO2010/054728, WO2010/099852, WO2011/032626, WO2011/157339, WO2012/007086, WO2015/036074, WO2015/104045, WO2015/117718, WO2016/015815, wobei es sich vorzugsweise um Iridium und Platinkomplexe handelt.

Further preferred phosphorescent organometallic complexes exhibit polypodal ligands as disclosed in WO2004081017, WO2005042550, US20050170206, WO2009/146770, WO2010/102709, WO2011/066898, WO2016124304, WO2017032439, WO2018019688, EP3184534, WO2018/011186, WO 2016/193243 und WO 2015/091716A1.

Furthermore, preferred binuclear phosphorescent organometallic complexes are disclosed in WO2011/045337, US2015/0171350, WO2016/079169, WO2018/019687, WO2018/041769, WO2018/054798, WO2018/069196, WO2018/069197, WO2018/069273.

Copper complexes as disclosed in WO2010/031485, US2013/150581, WO2013/017675, WO2013/007707, WO2013/001086, WO2012/156378, WO2013/072508, EP2543672 are also preferred.

Examples of suitable phosphorescent complexes comprising palladium are disclosed in WO2014/109814.

Typically any phosphorescent complexes that are known to the skilled person and used in phosphorescent OLEDs are suitable for the use for the purpose of the instant application.

Explicit examples of phosphorescent complexes are $Ir(ppy)_3$ and derivatives thereof and the following structures

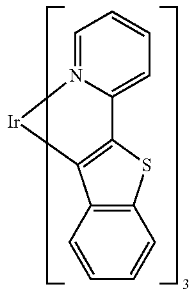
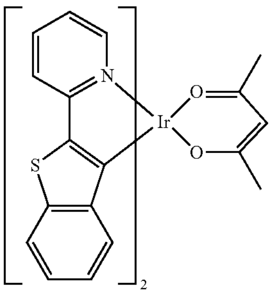
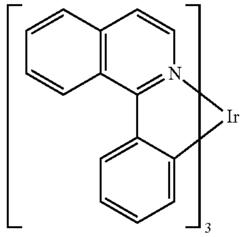
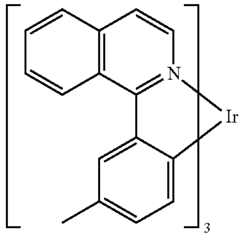
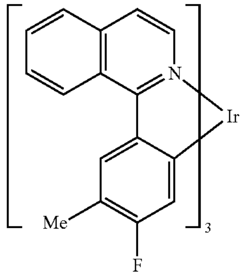
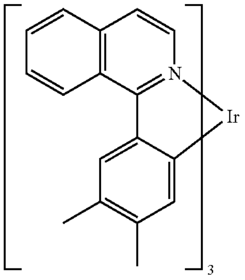
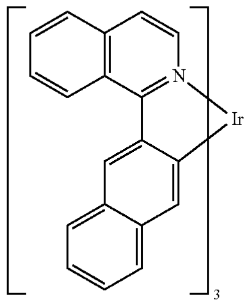
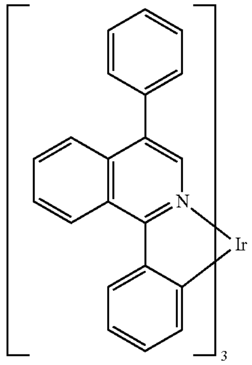
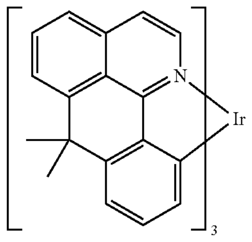
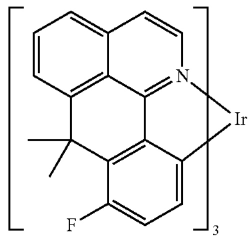

-continued
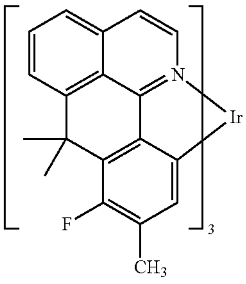
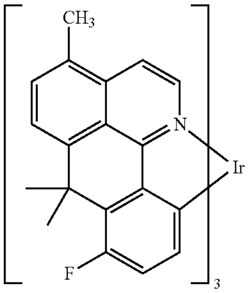
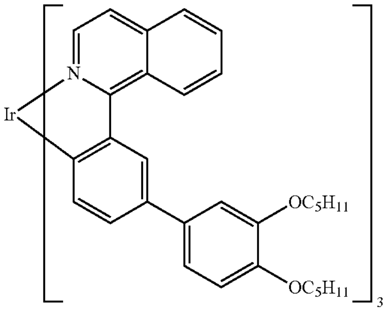
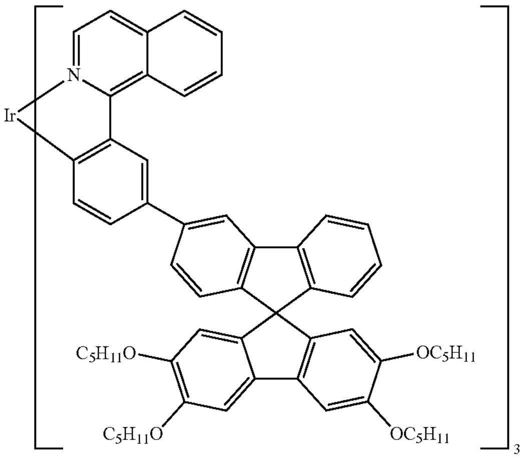
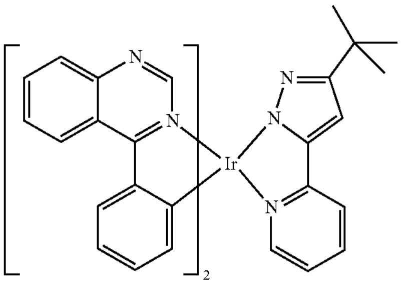
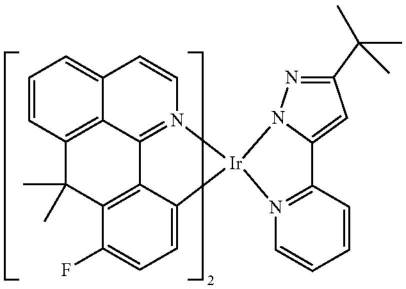
-continued
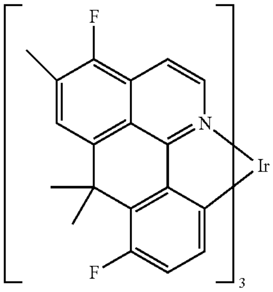
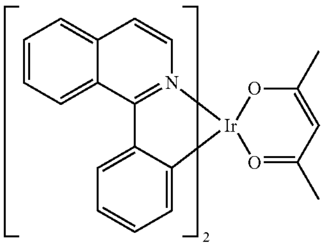
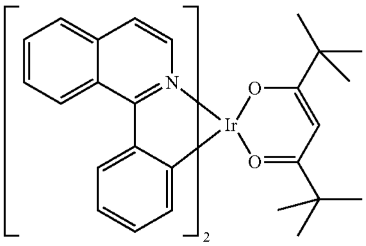
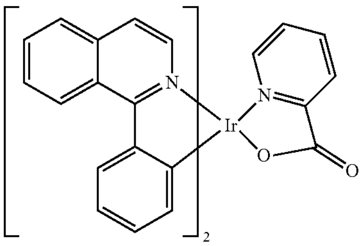
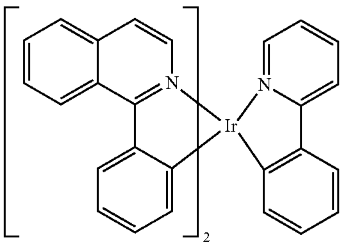
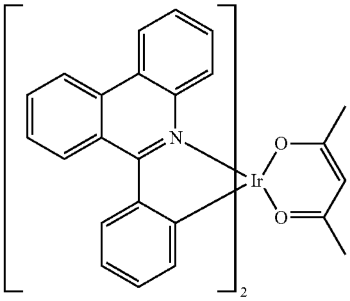

-continued
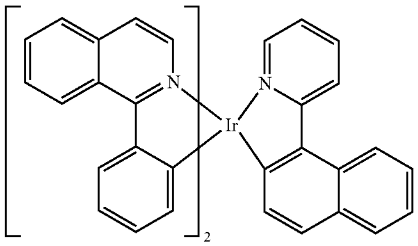
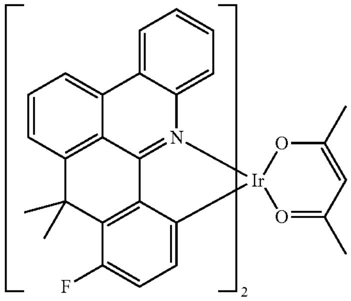
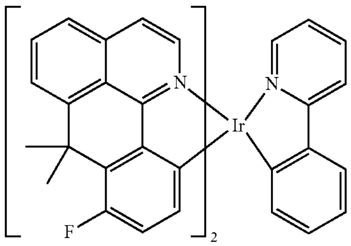
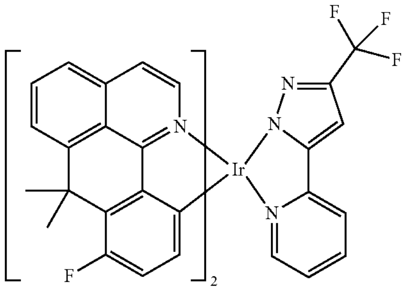
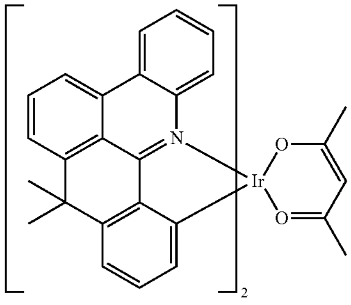
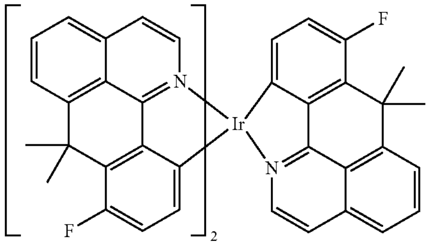
-continued
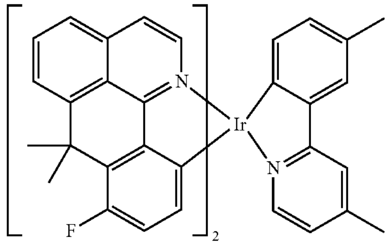
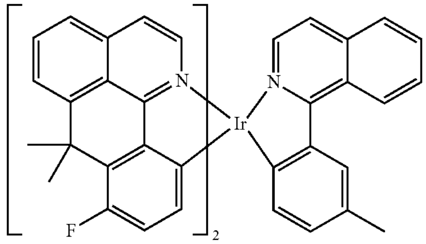
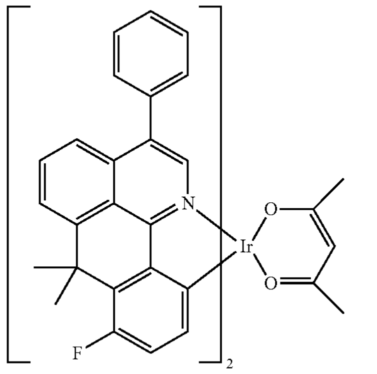
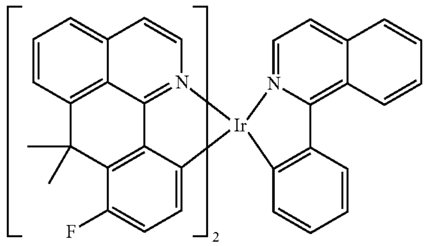
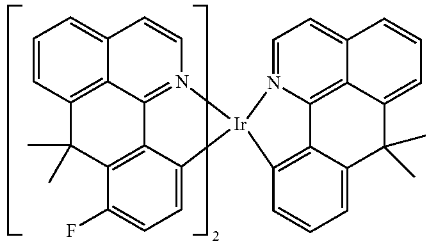

-continued
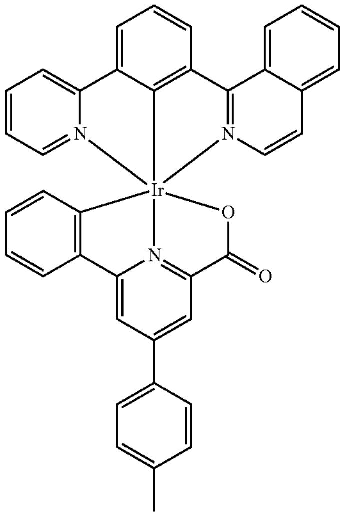
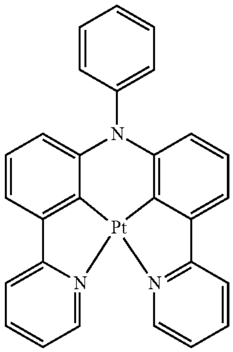
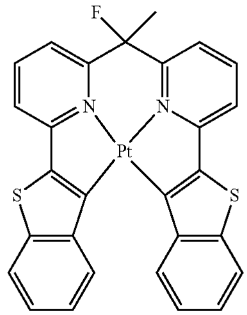
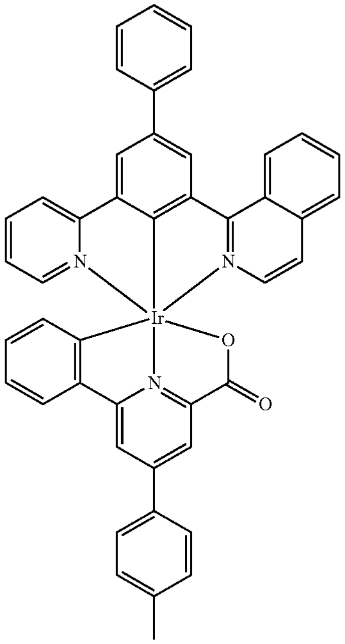
-continued
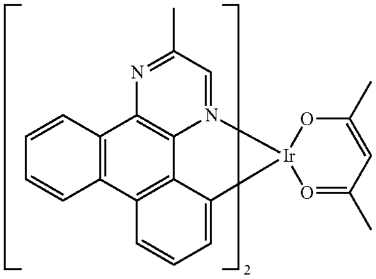
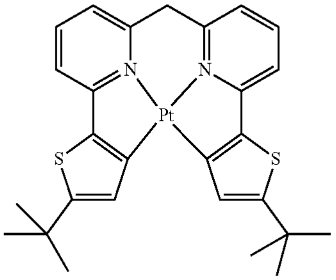
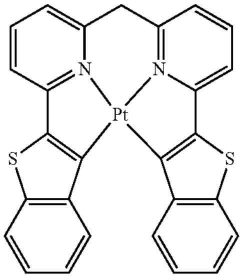
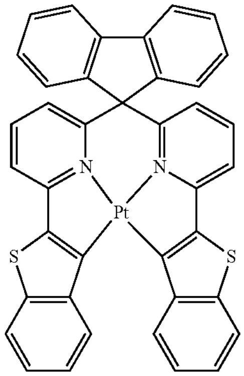
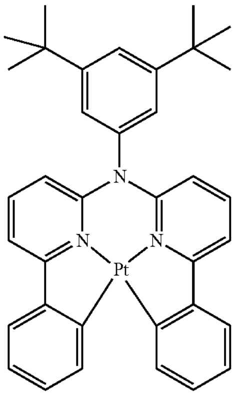
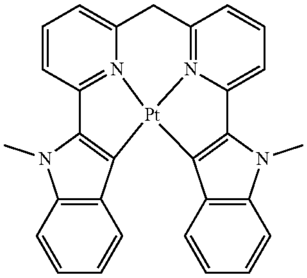

-continued
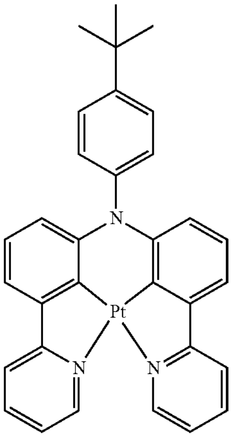
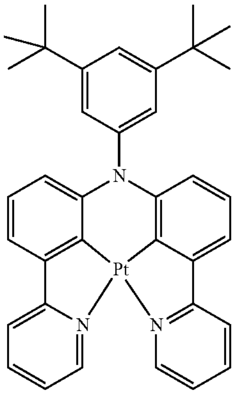
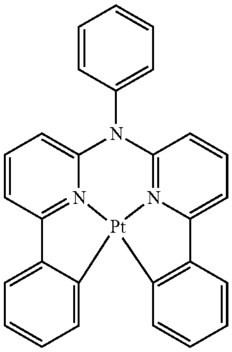
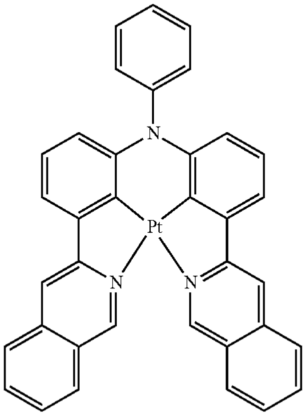
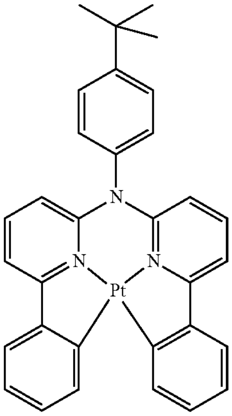
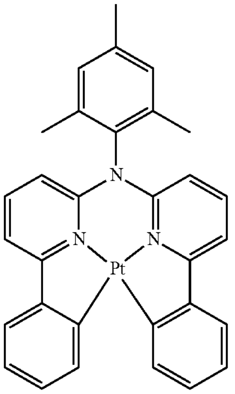
-continued
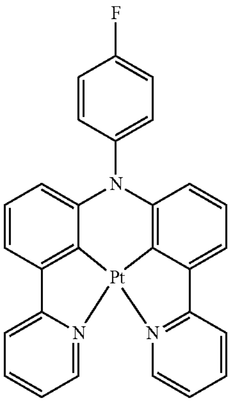
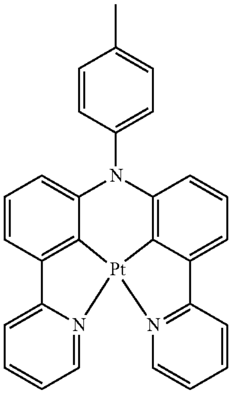
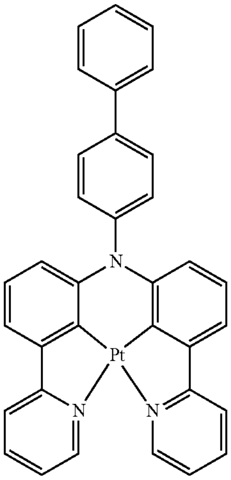
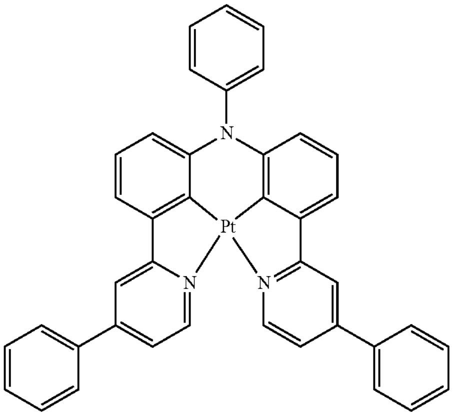

-continued
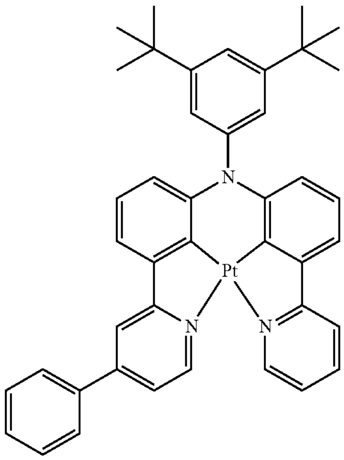
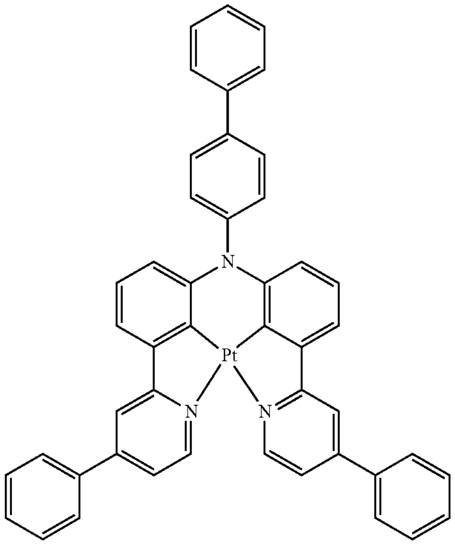
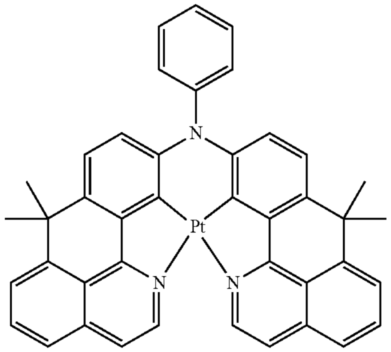
-continued
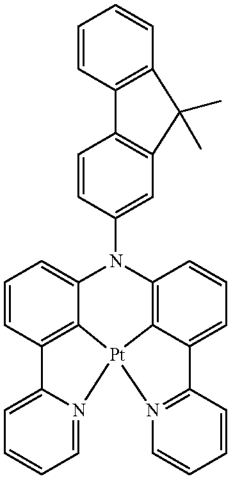
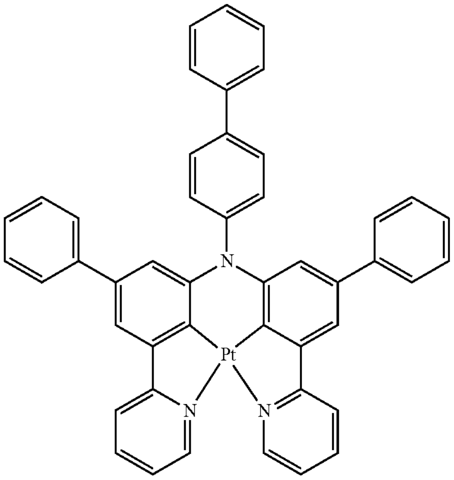
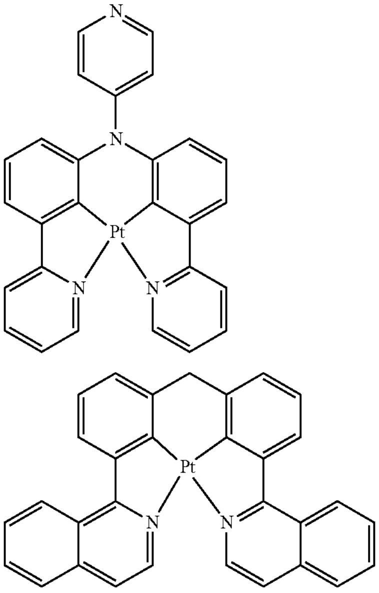

-continued
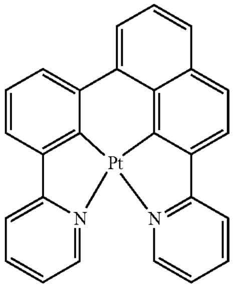
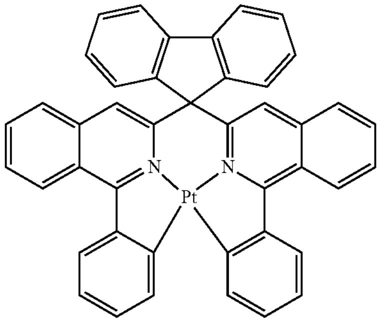
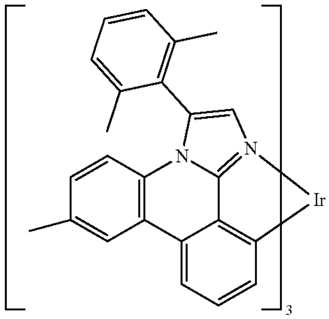
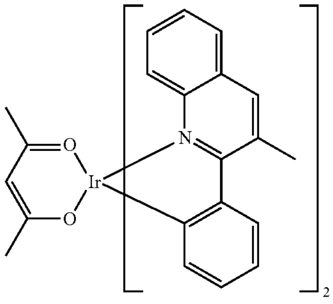
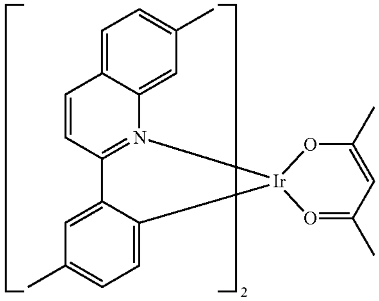
-continued
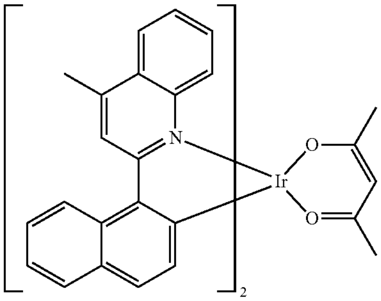
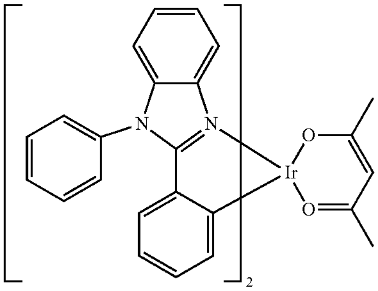
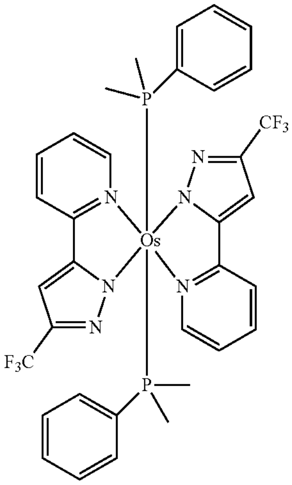
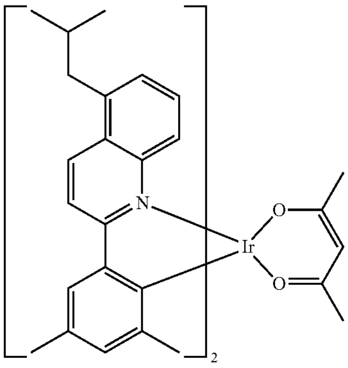
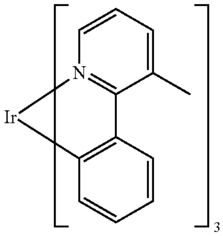
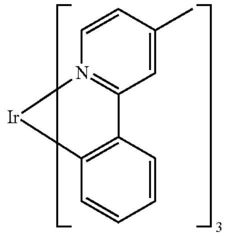

-continued
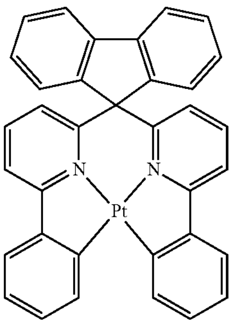
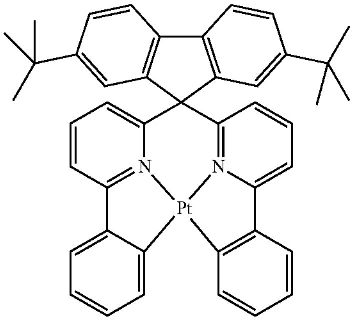
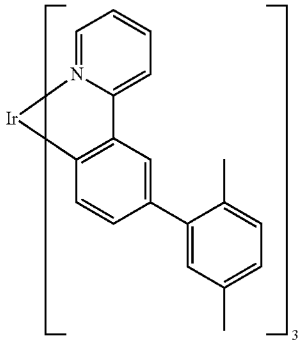
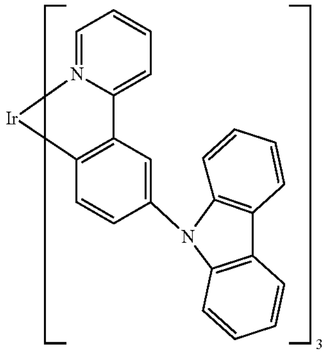
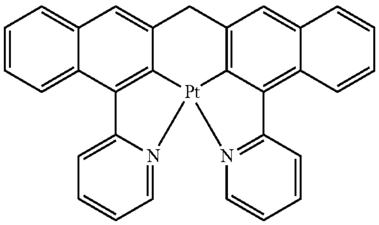
-continued
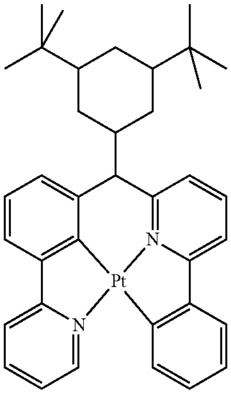
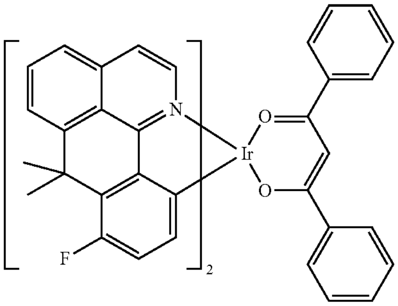
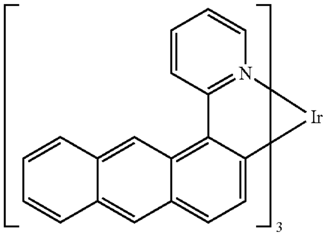
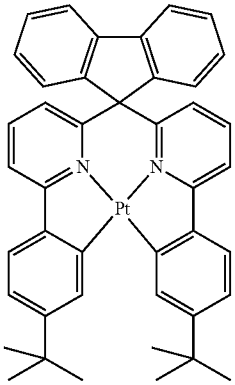
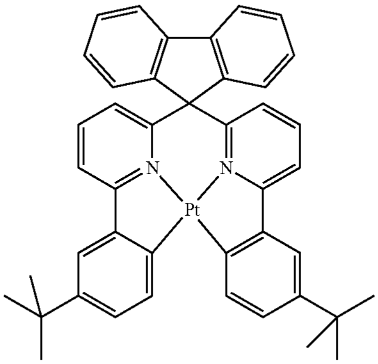

-continued
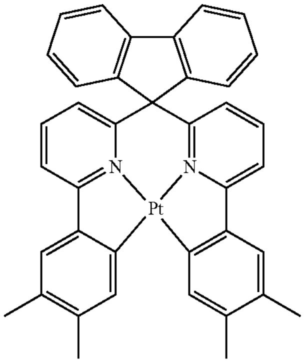
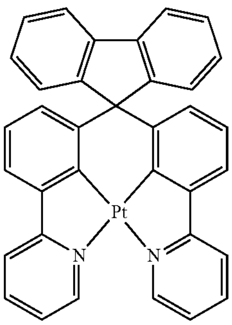
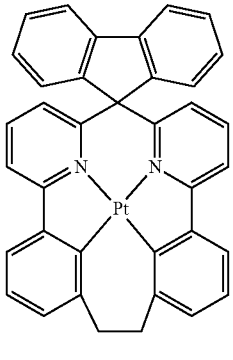
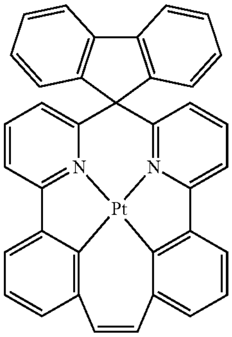
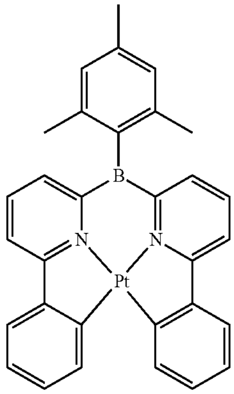
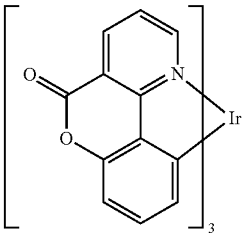
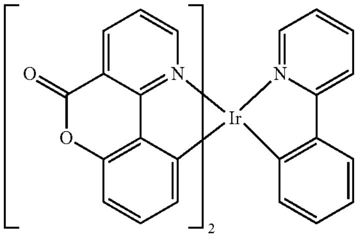
-continued
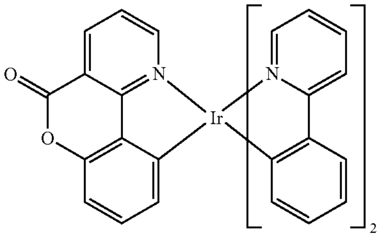
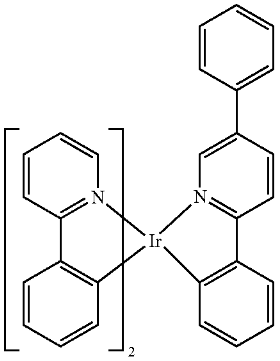
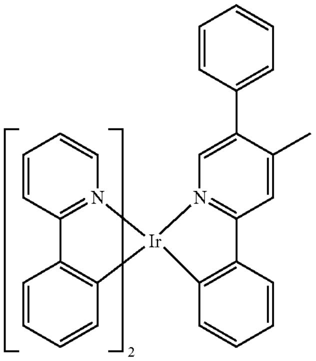
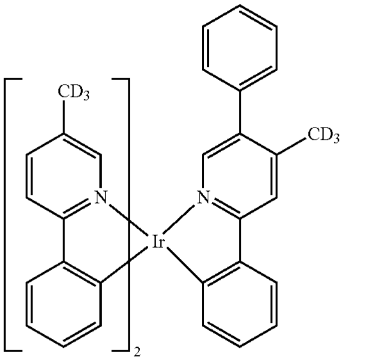
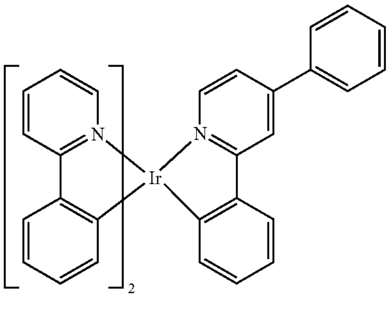

-continued
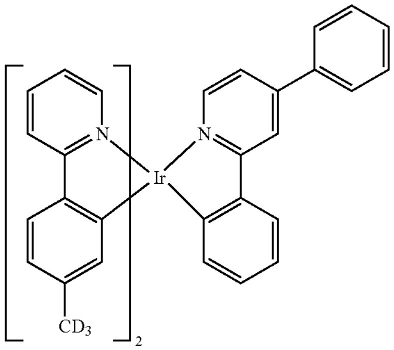
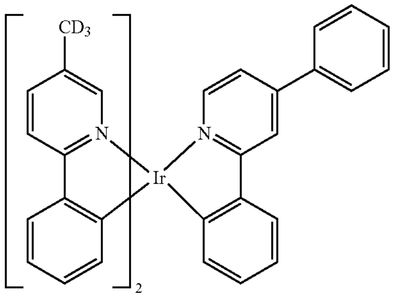
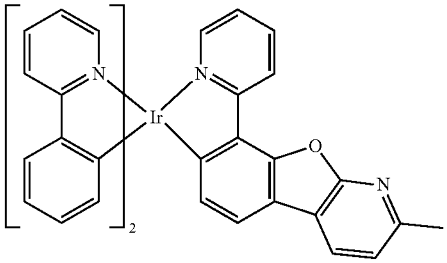
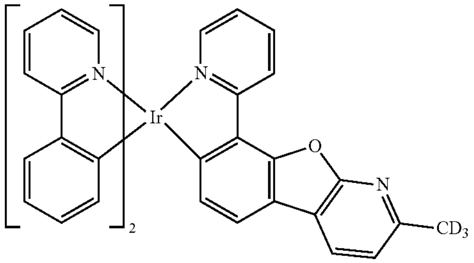
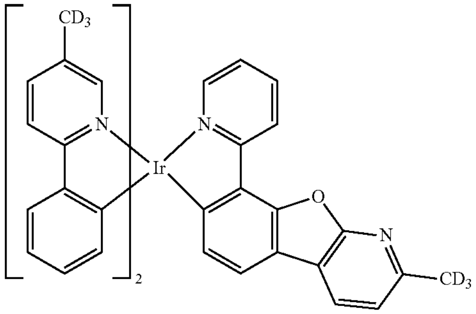
-continued
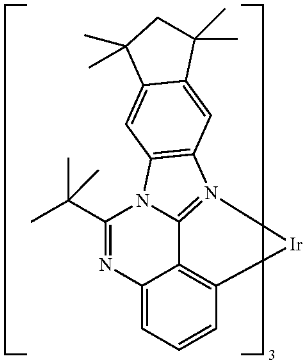
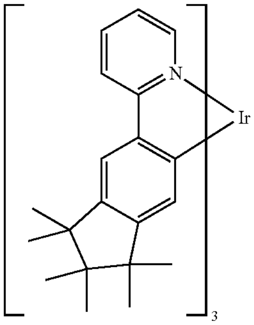
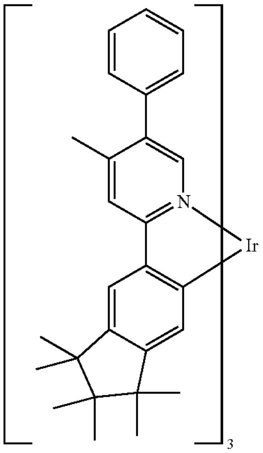
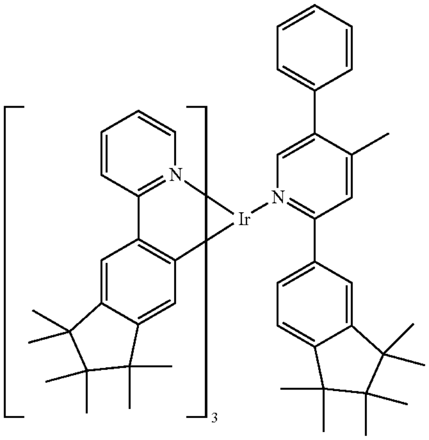
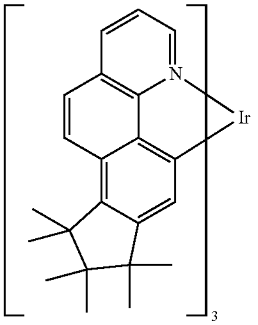

-continued
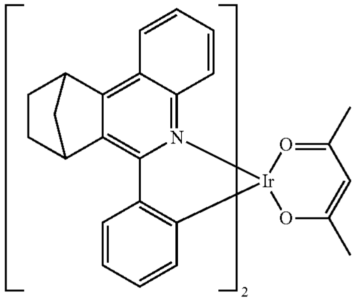
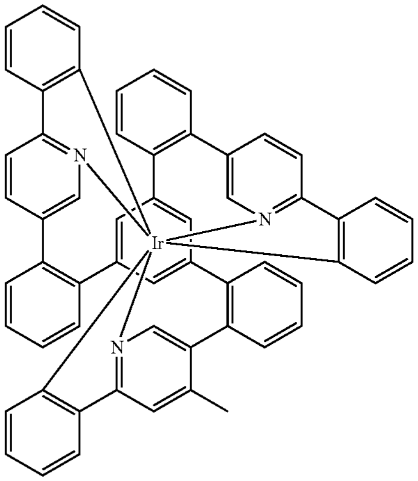
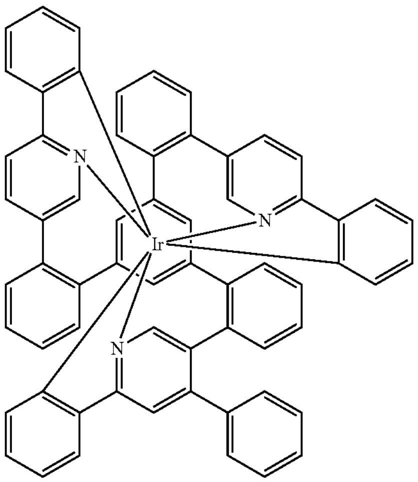
-continued
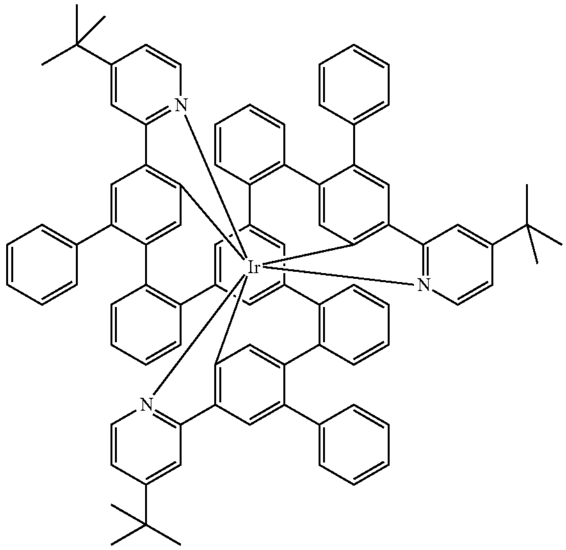
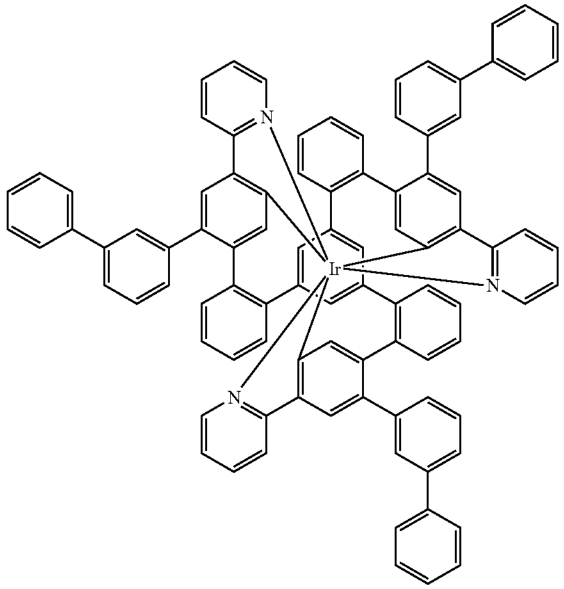
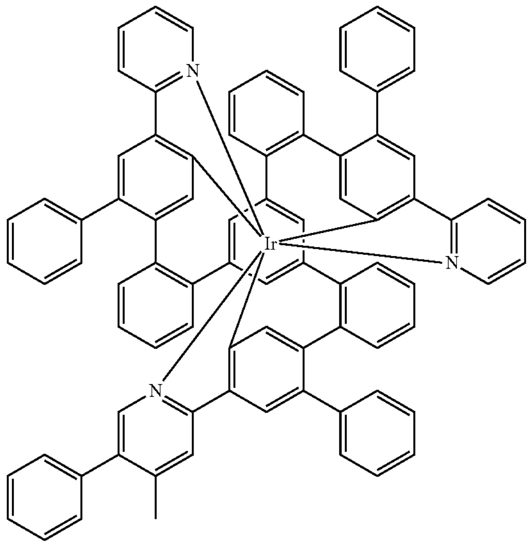

-continued
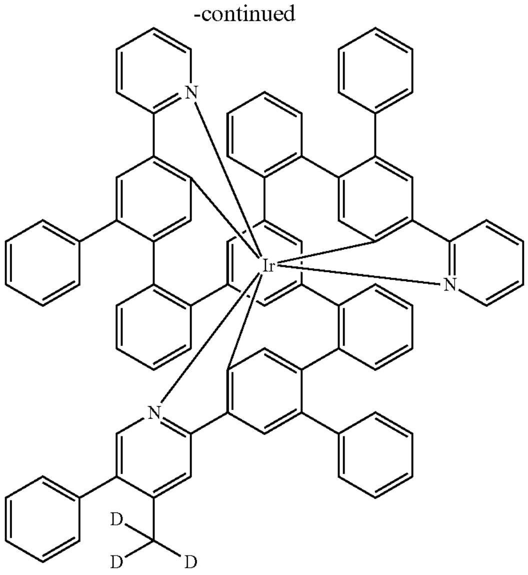
Further explicit examples for phosphorescent complexes are iridium and platinum complexes comprising carbene ligands wherein also heteroleptic and homoleptic, meridonale and faciale isomers of the following complexes can be used.
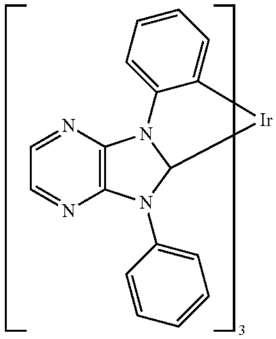
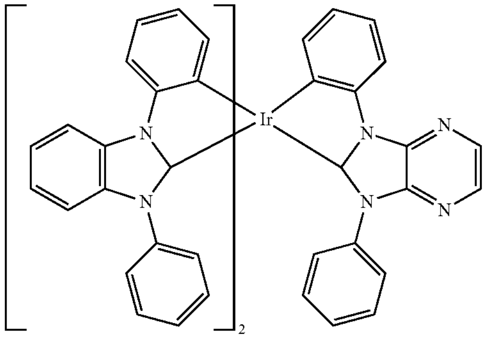
-continued
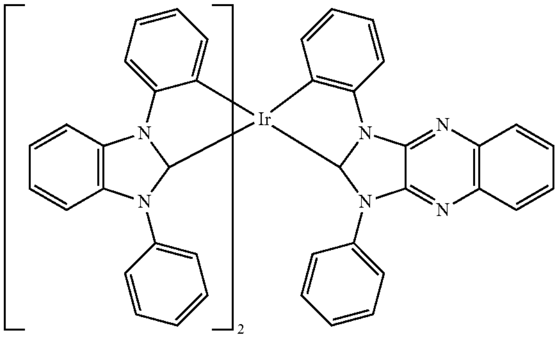
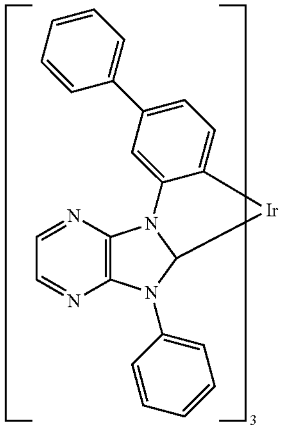
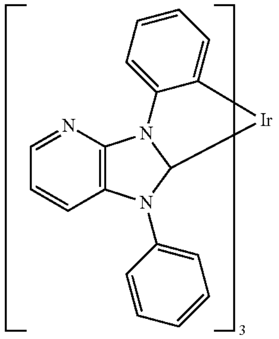
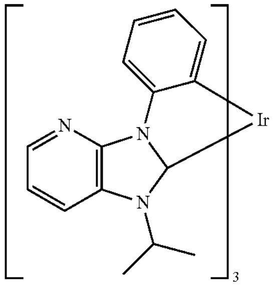
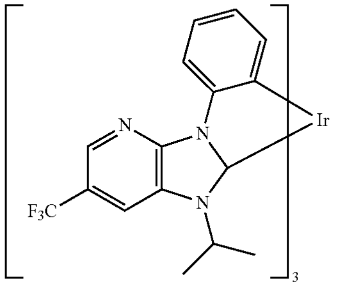

-continued

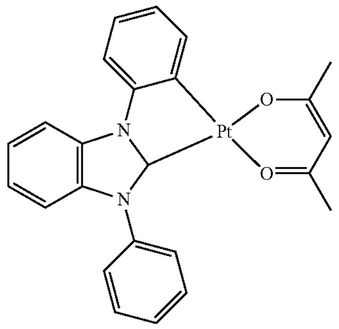

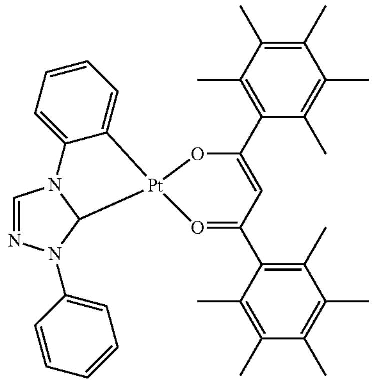

The following copper complexes are also suitable examples for phosphorescent complexes.

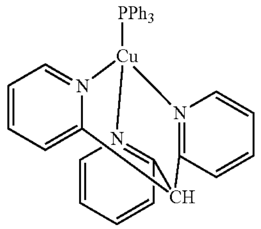

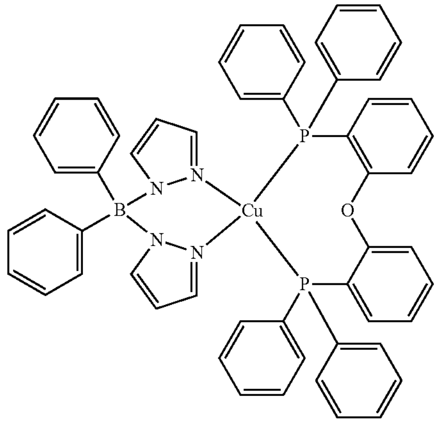

-continued

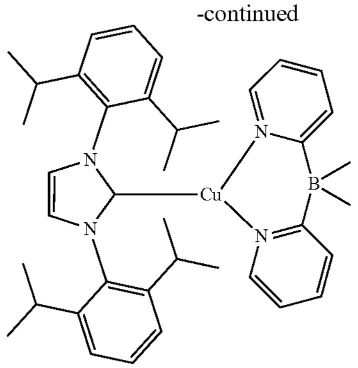

Preferred host or matrix groups are, in addition to all structural units mentioned as electron-transporting or hole-transporting groups below, those having larger band gaps between HOMO and LUMO than the emitter materials employed, in particular anthracene, benzanthracene, benzophenanthrene, phenanthrene, tetracene, coronene, chrysene, fluorene, spirofluorene, perylene, phthaloperylene, naphthaloperylene, decacyclene, rubrene, the oligoarylenevinylenes (for example DPVBi=4,4'-bis(2,2-diphenylethenyl)-1,1'-biphenyl), polypodal metal complexes like metal complexes of 8-hydroxyquinoline (e.g. $AlQ_3$ (=aluminium (III) tris(8-hydroxyquinoline)), quinoline-metal complexes, aminoquinoline-metal complexes, or benzoquinoline-metal complexes.

Preferred electron transporting group are triazines, pyrimidines, pyridines, pyrazines, pyrazoles, pyridazines, quinolines, isoquinolines, quinoxalines, quinazolines, tiazoles, benzothiazoles, oxazoles, benzoxazoles, benzimidazoles, oxadiazoles, phenoxazines, lactames, phenanthrolines and dibenzofurans.

Preferred hole transporting group are carbazoles, biscarbazoles, indenocarbazoles, indolocarbazoles, amines, triarylamines, fluoreneamines and spirobifluoreneamines.

Further preferably, the compound of the present invention has the general formula (1)

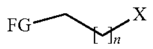

formula (1)

wherein the following applies to the symbols and indices:

X is selected from —SH, —C(=O)OH, —$NH_2$, —P(=O)(OH)(OH), —SeH, —P(R'R''), —$S^-Y^+$, —S(=O)OH, —S(=O)$O^-Y^+$, —C(=O)$O^-Y^+$, —OC(=O)R'''SH, —OC(=O)R'''$S^-Y^+$, —P(=O)(OH)($O^-Y^+$), —$Se^-Y^+$, —C(=S)SH, —C(=S)$S^-Y^+$, —$B(OH)_2$, —B(OH)$O^-Y^+$, —$B(O^-Y^+)_2$, —$B(O^-)_2Z^{2+}$, —P(=O)($O^-Y^+$)($O^-Y^+$) or —P(=O)($O^-$)($O^-$)$Z^{2+}$;

$Y^+$ is selected from $Na^+$, $K^+$, $Li^+$, ½ $Cd^{2+}$, ½ $Zn^{2+}$, ½ $Mg^{2+}$, ½ $Ca^{2+}$, or ½ $Sr^{2+}$, ⅓ $In^{3+}$, ⅓ $Ga^{3+}$;

$Z^{2+}$ is selected from $Cd^{2+}$, $Zn^{2+}$, $Mg^{2+}$, $Ca^{2+}$, $Sr^{2+}$;

R',R'' are, identically or differently, selected from H, linear or branched alkyl groups having 1 to 20 C atoms;

R'' is selected from linear or branched alkyl groups having 1 to 10 C atoms;

n is an integer from 0 to 20.

Accordingly, in the compound represented by general formula (1) group X takes the function of the anchor group, AG, as defined above, and the alkylene group/chain of the compound represented by general formula (1), the length of which is defined by index n, takes the function of the linker group, L, as defined above.

More preferably, X is selected from —SH, —$S^-$ $Y^+$, —C(═O)OH, —C(═O)$O^-Y^+$, —$B(OH)_2$, —B(OH)$O^-Y^+$, —$B(O^-Y^-)_2$, —$B(O^-)_2Z^{2+}$, —P(═O)(OH)(OH), —P(═O)(OH) ($O^-Y^+$), —P(═O)($O^-Y^+$)($O^-Y^+$), —P(═O)($O^-$)($O^-$) $Z^{2+}$, —OC(═O)R'''SH, or —OC(═O)R'''$S^-Y^+$, and most preferably X is +, —SH, —$S^-Y^+$, —P(═O)(OH)(OH), —P(═O)(OH)($O^-Y^+$), —P(═O)($O^-Y^+$)($O^-Y^+$), —P(═O)($O^-$)($O^-$)$Z^{2+}$, OC(═O)R'''SH, or —OC(═O)R'''$S^-Y^+$.

Index n is an integer from 0 to 20. That is, in case n is 0 then the organic functional group FG and the group X according to the general formula (1) are linked only by a group —$CH_2$—. Preferably, n is an integer from 0 to 10, very preferably from 0 to 6, particularly preferably from 0 to 4, very particularly preferably 0 or 2, and most preferably n is 2.

The notation "½ $Cd^{2+}$", or "½ $Zn^{2+}$", or "⅓ $In^{3+}$" or the like, as used herein for defining the cation $Y^+$ in the above formula (1), should be understood to mean that $Y^+$ can also represent a divalent cation, such as $Cd^{2+}$, or $Zn^{2+}$ and the like, or a trivalent cation, such as "⅓ $In^{3+}$" and the like. In this case, it shares its positive charges with two or three distinct monovalent anionic groups X (i.e., one divalent or trivalent cation acts as counter-ion for two and three distinct molecules of the compound of formula (1), respectively).

Further preferably, $Y^+$ is selected from $Na^+$, $K^+$ or $Li^+$. Also preferably, $Z^{2+}$ is selected from $Cd^{2+}$, $Zn^{2+}$, $Mg^{2+}$.

According to a preferred embodiment, the organic functional group FG is an electron transporting group, ET, which is more preferably selected from an electron-deficient heteroaromatic group. Even more preferred are heteroaromatic groups having 6 aromatic ring atoms of which at least one, preferably two and very preferably at least three is a nitrogen atom, or heteroaromatic groups having 5 aromatic ring atoms of which at least two are heteroatoms, and preferably at least one of them is a nitrogen atom.

Particularly preferable, the electron transporting group is selected from triazines, pyrimidines, pyridines, pyrazines, pyrazoles, pyridazines, quinolines, isoquinolines, quinoxalines, quinazolines, tiazoles, benzothiazoles, oxazoles, benzoxazoles, benzimidazoles, oxadiazoles, phenoxazines, lactames, phenanthrolines and dibenzofurans.

The electron transporting group ET preferably has a LUMO (lowest unoccupied molecular orbital) energy of less than −1.3 eV, very preferably less than −2.5 eV and most preferably less than −2.7 eV.

Molecular orbitals, especially also the highest occupied molecular orbital (HOMO) and the lowest unoccupied molecular orbital (LUMO), the energy levels thereof and the energy of the lowest triplet state $T_1$ and that of the lowest excited singlet state $S_1$ of the materials are determined via quantum-chemical calculations. For calculation of organic substances without metals, an optimization of geometry is first conducted by the "Ground State/Semi-empirical/Default Spin/AM1/Charge 0/Spin Singlet" method. Subsequently, an energy calculation is effected on the basis of the optimized geometry. This is done using the "TD-SCF/DFT/Default Spin/B3PW91" method with the "6-31G(d)" basis set (charge 0, spin singlet). For metal-containing compounds, the geometry is optimized via the "Ground State/Hartree-Fock/Default Spin/LanL2 MB/Charge 0/Spin Singlet" method. The energy calculation is effected analogously to the above-described method for the organic substances, except that the "LanL2DZ" basis set is used for the metal atom and the "6-31 G(d)" basis set for the ligands. The HOMO energy level HEh or LUMO energy level LEh is obtained from the energy calculation in Hartree units. This is used to determine the HOMO and LUMO energy levels in electron volts, calibrated by cyclic voltammetry measurements, as follows:

$$HOMO(eV)=((HEh*27.212)-0.9899)/1.1206;$$

$$LUMO(eV)=((LEh*27.212)-2.0041)/1.385$$

These values are to be regarded as HOMO and LUMO energy levels of the materials in the context of this application.

The lowest triplet state $T_1$ is defined as the energy of the triplet state having the lowest energy, which is apparent from the quantum-chemical calculation described. The lowest excited singlet state $S_1$ is defined as the energy of the excited singlet state having the lowest energy, which is apparent from the quantum-chemical calculation described.

The method described herein is independent of the software package used and always gives the same results. Examples of frequently utilized programs for this purpose are "Gaussian09 W" (Gaussian Inc.) and Q-Chem 4.1 (Q-Chem, Inc.).

More preferably, the electron transporting group ET is a heteroaromatic group selected from the following groups (ET-1)

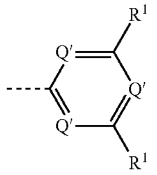

(ET-2)

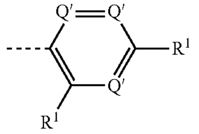

(ET-3)

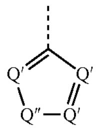

(ET-4)

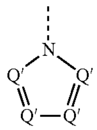

(ET-5)

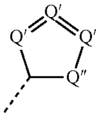

(ET-6)

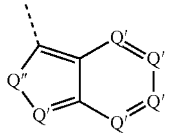

-continued (ET-7)

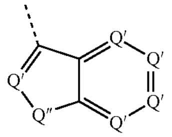

(ET-8)

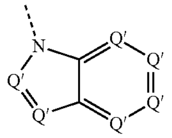

(ET-9)

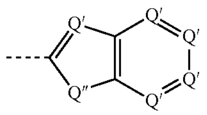

(ET-10)

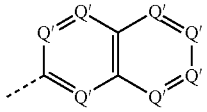

(ET-11)

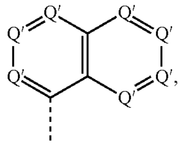

wherein the dashed line represents the bonding position to the linker group, L, i.e., the alkylene group linking groups FG and X in formula (1);

Q' is selected, identically or differently at each occurrence, from $CR^1$ and N;

Q'' is selected from $NR^1$, O and S;

$R^1$ is, identically or differently at each occurrence, selected from H, D, F, Cl, Br, I, $N(R^2)_2$, CN, $NO_2$, $Si(R^2)_3$, $B(OR^2)_2$, $C(=O)R^2$, $P(=O)(R^2)_2$, $S(=O)R^2$, $S(=O)_2R^2$, $OSO_2R^2$, a straight-chain alkyl, alkoxy or thioalkoxy group having 1 to 40 carbon atoms or a straight-chain alkenyl or alkynyl group having 2 to 40 carbon atoms or a branched or cyclic alkyl, alkenyl, alkynyl, alkoxy, alkylalkoxy or thioalkoxy group having 3 to 40 carbon atoms, each of which may be substituted by one or more $R^2$ radicals, where one or more nonadjacent $CH_2$ groups may be replaced by $R^2C{=}CR^2$, C≡C, $Si(R^2)_2$, $Ge(R^2)_2$, $Sn(R^2)_2$, C=O, C=S, C=Se, $C{=}NR^2$, $P(=O)(R^2)$, SO, $SO_2$, $NR^2$, O, S or $CONR^2$ and where one or more hydrogen atoms may be replaced by D, F, Cl, Br, I, CN or $NO_2$, or an aromatic or heteroaromatic ring system which has 5 to 60 aromatic ring atoms and may be substituted in each case by one or more $R^2$ radicals, or an aryloxy, arylalkyl or heteroaryloxy group which has 5 to 60 aromatic ring atoms and may be substituted by one or more $R^2$ radicals, or a combination of two or more of these groups or a crosslinkable Q group; wherein two or more adjacent $R^1$ radicals together may form a mono- or polycyclic, aliphatic or aromatic ring system, wherein it is preferred that two or more adjacent $R^1$ radicals together do not form a mono- or polycyclic, aliphatic or aromatic ring system;

$R^2$ is the same or different at each instance and is H, D, F, Cl, Br, I, $N(R^3)_2$, CN, $NO_2$, $Si(R^3)_3$, $B(OR^3)_2$, $C(=O)R^3$, $P(=O)(R^3)_2$, $S(=O)R^3$, $S(=O)_2R^3$, $OSO_2R^3$, a straight-chain alkyl, alkoxy or thioalkoxy group having 1 to 40 carbon atoms or a straight-chain alkenyl or alkynyl group having 2 to 40 carbon atoms or a branched or cyclic alkyl, alkenyl, alkynyl, alkoxy, alkylalkoxy or thioalkoxy group having 3 to 40 carbon atoms, each of which may be substituted by one or more $R^3$ radicals, where one or more nonadjacent $CH_2$ groups may be replaced by $R^3C{=}CR^3$, C≡C, $Si(R^3)_2$, $Ge(R^3)_2$, $Sn(R^3)_2$, C=O, C=S, C=Se, $C{=}NR^3$, $P(=O)(R^3)$, SO, $SO_2$, $NR^3$, O, S or $CONR^3$ and where one or more hydrogen atoms may be replaced by D, F, Cl, Br, I, CN or $NO_2$, or an aromatic or heteroaromatic ring system which has 5 to 60 aromatic ring atoms and may be substituted in each case by one or more $R^3$ radicals, or an aryloxy, arylalkyl or heteroaryloxy group which has 5 to 60 aromatic ring atoms and may be substituted by one or more $R^3$ radicals, or a combination of two or more of these groups; wherein two or more adjacent $R^2$ radicals together may form a mono- or polycyclic, aliphatic or aromatic ring system;

$R^3$ is the same or different at each instance and is H, D, F or an aliphatic, aromatic and/or heteroaromatic hydrocarbyl radical having 1 to 20 carbon atoms, in which one or more hydrogen atoms may also be replaced by F; wherein two or more $R^3$ substituents together may also form a mono- or polycyclic, aliphatic or aromatic ring system, and wherein at least one Q' is N.

The following definitions apply to the chemical groups used as general definitions. They only apply insofar as no more specific definitions are given.

An aryl group in the sense of this invention contains 5 to 60 or 6 to 40 aromatic ring atoms, of which none is a heteroatom. An aryl group here is taken to mean either a simple aromatic ring, for example benzene, or a condensed aromatic polycycle, for example naphthalene, phenanthrene, or anthracene. A condensed aromatic polycycle in the sense of the present application consists of two or more simple aromatic rings condensed with one another.

A heteroaryl group in the sense of this invention contains 5 to 60 or 5 to 40 aromatic ring atoms, at least one of which is a heteroatom. The heteroatoms are preferably selected from N, O and S. A heteroaryl group here is taken to mean either a simple heteroaromatic ring, such as pyridine, pyrimidine or thiophene, or a condensed heteroaromatic polycycle, such as quinoline or carbazole. A condensed heteroaromatic polycycle in the sense of the present application consists of two or more simple heteroaromatic rings condensed with one another.

An aryl or heteroaryl group, which may in each case be substituted by the above-mentioned radicals and which may be linked to the aromatic or heteroaromatic ring system via any desired positions, is taken to mean, in particular, groups derived from benzene, naphthalene, anthracene, phenanthrene, pyrene, dihydropyrene, chrysene, perylene, fluoranthene, benzanthracene, benzophenanthrene, tetracene, pentacene, benzopyrene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, pheno-thiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phen-anthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

An aryloxy group in the sense of this invention is understood to mean an aryl group as defined above, which is bonded via an oxygen atom. In analogy, the same applies to an heteroaryloxy group.

An arylalkyl group in the sense of this invention is understood to mean an aryl group as defined above, to which an alkyl group as defined below is bonded.

An aromatic ring system in the sense of this invention contains 6 to 60 or 6 to 40 C atoms in the ring system and does not comprise any heteroatoms as aromatic ring atoms. An aromatic ring system in the sense of this application therefore does not comprise any heteroaryl groups. An aromatic ring system in the sense of this invention is intended to be taken to mean a system which does not necessarily contain only aryl groups, but instead in which, in addition, a plurality of aryl groups may be connected by a non-aromatic unit such as one or more optionally substituted C, Si, N, O or S atoms. The non-aromatic unit in such case comprises preferably less than 10% of the atoms other than H, relative to the total number of atoms other than H of the whole aromatic ring system. Thus, for example, systems such as 9,9'-spirobifluorene, 9,9'-diarylfluorene, triarylamine, diaryl ether, and stilbene are also intended to be taken to be aromatic ring systems in the sense of this invention, as are systems in which two or more aryl groups are connected, for example, by a linear or cyclic alkyl, alkenyl or alkynyl group or by a silyl group. Furthermore, systems in which two or more aryl groups are linked to one another via single bonds are also taken to be aromatic ring systems in the sense of this invention, such as, for example, systems such as biphenyl and terphenyl.

Preferably, an aromatic ring system is understood to be a chemical group, in which the aryl groups which constitute the chemical group are conjugated with each other. This means that the aryl groups are connected with each other via single bonds or via connecting units which have a free pi electron pair which can take part in the conjugation. The connecting units are preferably selected from nitrogen atoms, single C═C units, single C≡C units, multiple C═C units and/or C≡C units which are conjugated with each other, —O—, and —S—.

A heteroaromatic ring system in the sense of this invention contains 5 to 60 or 5 to 40 aromatic ring atoms, at least one of which is a heteroatom. The heteroatoms are preferably selected from N, O or S. A heteroaromatic ring system is defined as an aromatic ring system above, with the difference that it must obtain at least one heteroatom as one of the aromatic ring atoms. It thereby differs from an aromatic ring system according to the definition of the present application, which cannot comprise any heteroatom as aromatic ring atom.

An aromatic ring system having 6 to 60 or 6 to 40 aromatic ring atoms, or a heteroaromatic ring system having 5 to 60 or 5 to 40 aromatic ring atoms is in particular a group which is derived from the above mentioned aryl or heteroaryl groups, or from biphenyl, terphenyl, quaterphenyl, fluorene, spirobifluorene, dihydrophenanthrene, dihydropyrene, tetrahydropyrene, indenofluorene, truxene, isotruxene, spirotruxene, spiroisotruxene, and indenocarbazole.

For the purposes of the present invention, a straight-chain alkyl group having 1 to 40 or 1 to 20 C atoms or a branched or cyclic alkyl group having 3 to 40 or 3 to 20 C atoms or an alkenyl or alkynyl group having 2 to 40 or 2 to 20 C atoms, in which, in addition, individual H atoms or $CH_2$ groups may be substituted by the groups mentioned above under the definition of the radicals, is preferably taken to mean the radicals methyl, ethyl, n-propyl, i-propyl, n-butyl, i-butyl, s-butyl, t-butyl, 2-methylbutyl, n-pentyl, s-pentyl, cyclopentyl, neopentyl, n-hexyl, cyclohexyl, neohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl or octynyl. Considering the above definition, a straight-chain alkylene group having 1 to 20 C atoms, or a cyclic or branched alkylene group having 3 to 20 C atoms is taken to mean the respective diradicals of the above-mentioned radicals.

An alkoxy or thioalkyl group having 1 to 40 or 1 to 20 C atoms is preferably taken to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy, 2,2,2-trifluoroethoxy, methylthio, ethylthio, n-propylthio, i-propylthio, n-butylthio, i-butylthio, s-butylthio, t-butylthio, n-pentylthio, s-pentylthio, n-hexylthio, cyclohexyl-thio, n-heptylthio, cycloheptylthio, n-octylthio, cyclooctylthio, 2-ethylhexyl-thio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio.

According to a further preferred embodiment, the electron transporting group ET is not directly bonded to the linker group, L, i.e., the alkylene group linking groups FG and X in formula (1), but via a divalent group $Ar^J$ that interconnects the linking group L and the electron transporting group ET according to the following structure:

$$—[Ar_J]_g\text{-ET}$$

wherein the dashed line indicates the bond to the linker group, L, i.e., the alkylene group in formula (1), and wherein group ET is as described above and g is 0 or 1.

In case index g is 0, this means that the group $Ar^J$ is not present, so that the linker group and the electron transporting group ET are directly connected with each other, as shown in formula (1).

Preferably, divalent group $Ar^J$ is selected from aromatic or heteroaromatic ring systems having 6 to 30 aromatic ring atoms, which may be substituted by one or more radicals $R^1$. It is particularly preferred if $Ar^J$ is selected from divalent groups derived from benzene, pyridine, pyrimidine, biphenyl, terphenyl, fluorene, spirobifluorene, furan, dibenzofuran, thiophene, dibenzothiophene, which may each be substituted by one or more radicals $R^1$. Particular preferably, $Ar^J$ is a phenylene, biphenylene or terphenylene group, and most preferably $Ar^J$ is a phenylene group.

Preferred examples of heteroaromatic electron transporting groups ET are (independent of g being 0 or 1 as indicated above): pyridines, pyrazines, pyrimidines, pyridazines, 1,2,4-triazines, 1,3,5-triazines, quinolines, isoquinolines, quinoxalines, quinazoline, pyrazoles, imidazoles, benzimidazoles, thiazoles, benzothiazoles, oxazoles or benzoxazoles, each of which may be substituted by $R^1$. Even more preferably, the electron-transporting group is a pyridine, pyrazine, pyrimidine, pyridazine and 1,3,5-triazine substituted by one or more $R^1$ radicals.

Very preferred heteroaromatic electron transporting groups ET are selected from the following groups (ET-12) to (ET-21):

(ET-12)

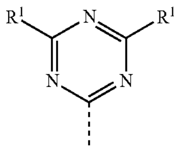

(ET-13)

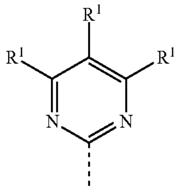

(ET-14)

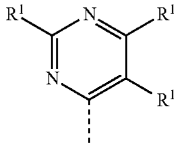

(ET-15)

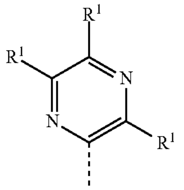

(ET-16)

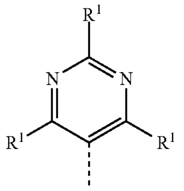

(ET-17)

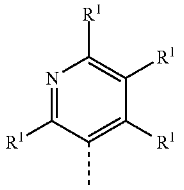

(ET-18)

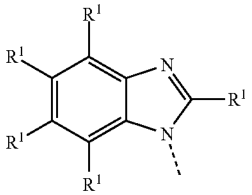

-continued (ET-19)

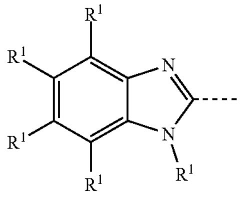

(ET-20)

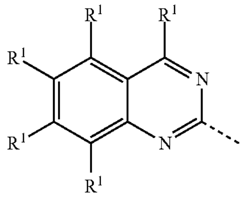

, (ET-21)

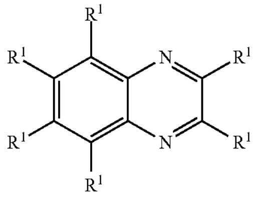

wherein $R^1$ is as defined above and the dashed line represents the bonding position to the linker group, L, i.e., the alkylene group linking groups FG and X in formula (1), or to the group $Ar^J$, if present.

The $R^1$ substituents in the electron transporting groups ET are preferably selected from the group consisting of H and an aromatic or heteroaromatic ring system which has 5 to 60 aromatic ring atoms, which may be substituted in each case by one or more $R^2$ radicals, wherein it is preferred that an electron transporting group ET, which is substituted with one or more radicals $R^1$, does not comprise any electron-rich aromatic or heteroaromatic rings or ring systems.

Examples of very particularly preferred heteroaromatic electron transporting groups ET are the following groups, which may be substituted by one or more independent $R^2$ radicals as defined above, where the dotted bonds indicate the binding positions to the linker group, L, i.e., the alkylene group linking groups FG and X in formula (1):

(ET-22)

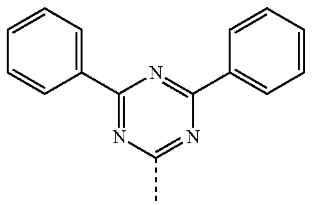

(ET-23)

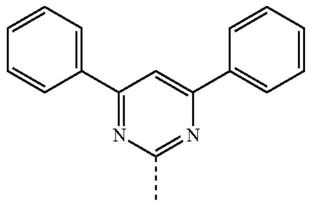

-continued
(ET-24)
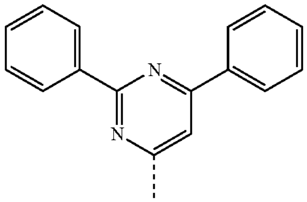
(ET-25)
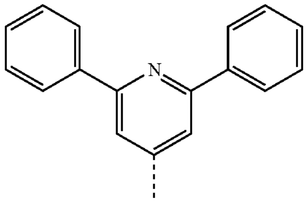
(ET-26)
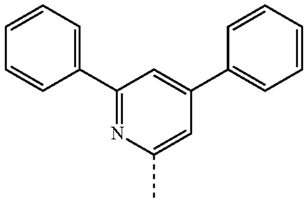
(ET-27)
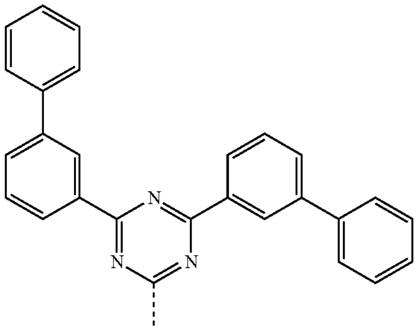
(ET-28)
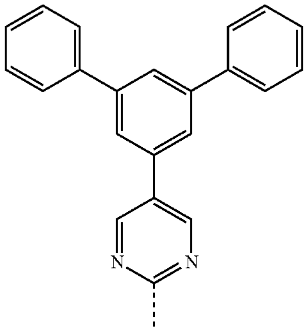
(ET-29)
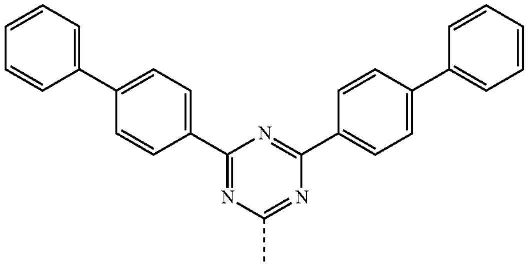
-continued
(ET-30)
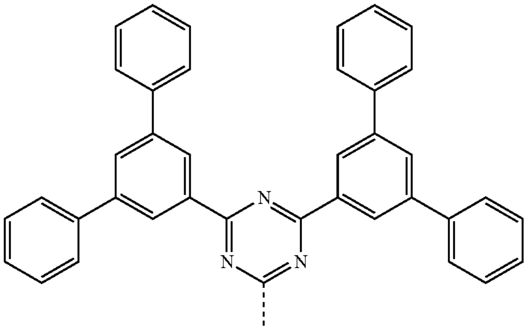
(ET-31)
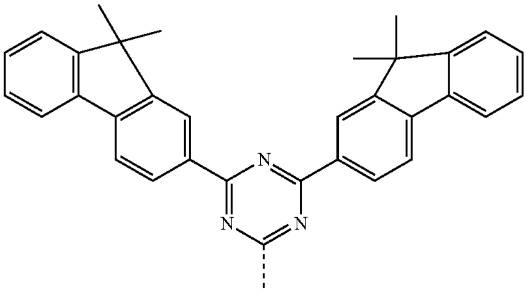
(ET-32)
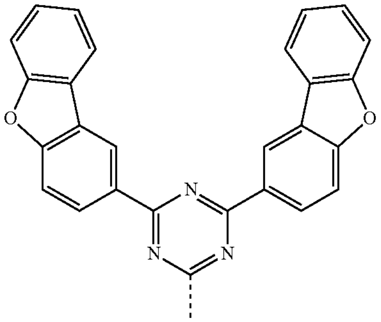
(ET-33)
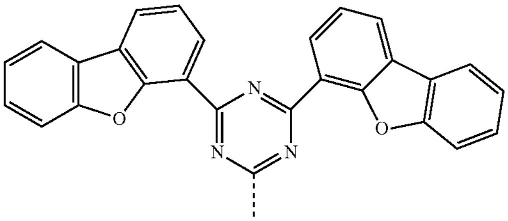
(ET-34)
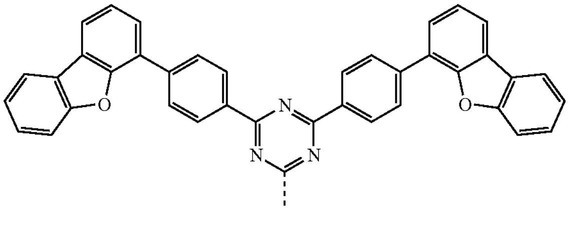

-continued
(ET-35)
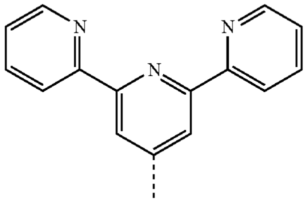
(ET-36)
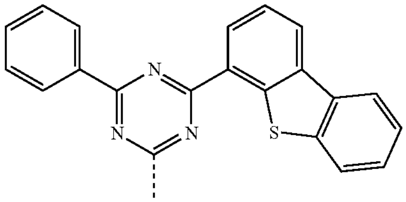
(ET-37)
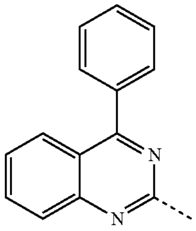
(ET-38)
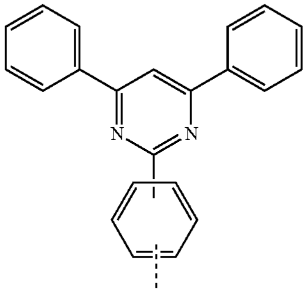
(ET-39)
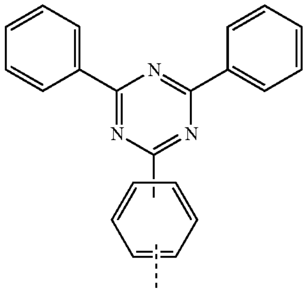
(ET-40)
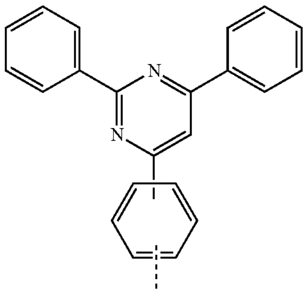
-continued
(ET-41)
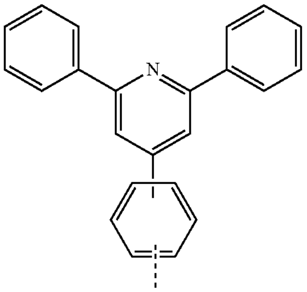
(ET-42)
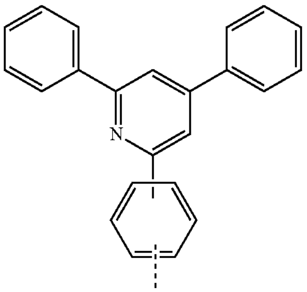
(ET-43)
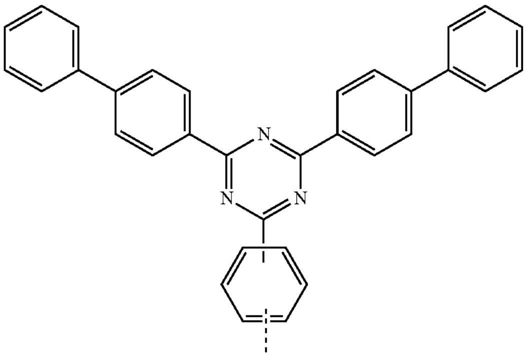
(ET-44)
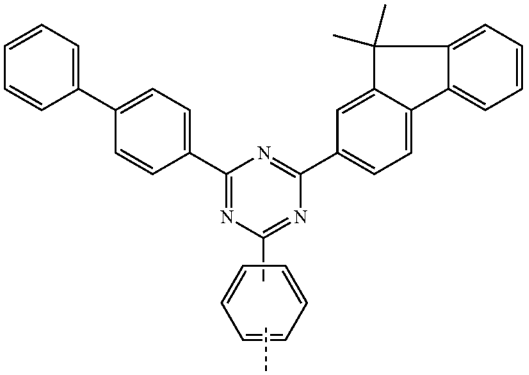

-continued (ET-45)

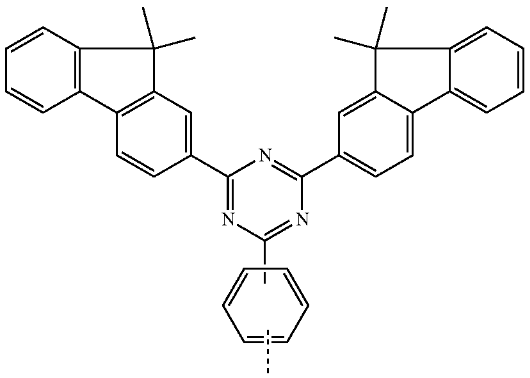

(ET-46)

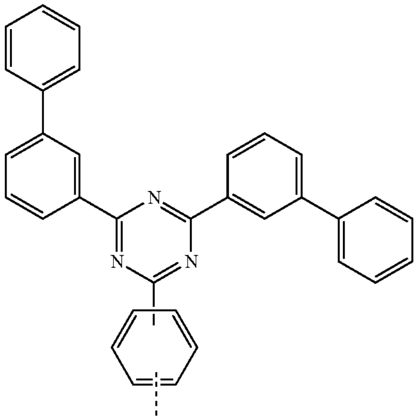

(ET-47)

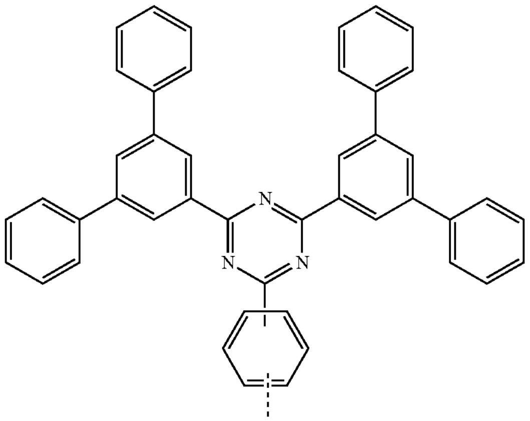

-continued (ET-48)

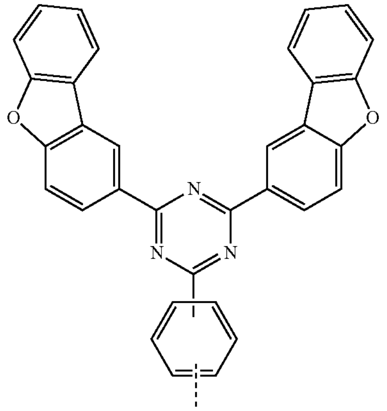

(ET-49)

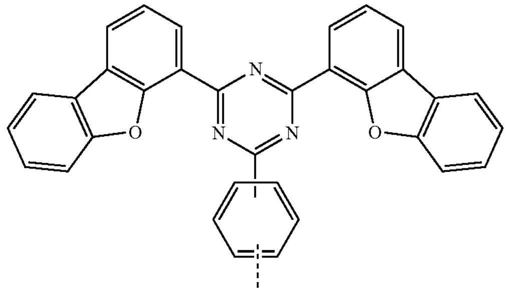

(ET-50)

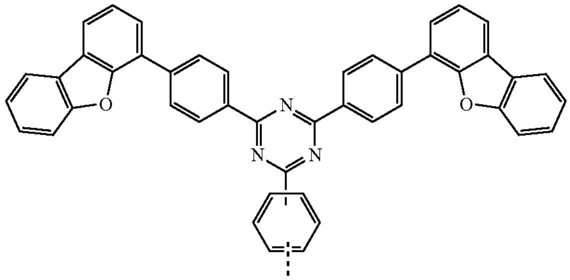

(ET-51)

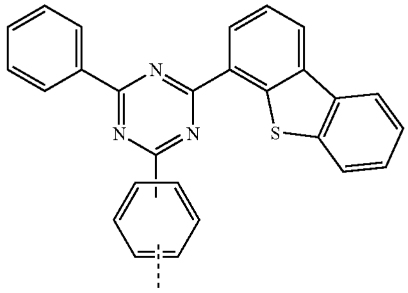

According to another preferred embodiment, the organic functional group FG is a hole transporting group HT, which is more preferably selected from an electron-rich heteroaromatic group. The term hole transporting here describes a functional group which enables a compound carrying this functional group in an electronic device (e.g. an electroluminescent device) to transport positive charges as the majority charge carrier. Even more preferred are heteroaryl groups having 5 to 60 aromatic ring atoms, wherein nitrogen atoms are preferred heteroatoms. Particularly preferable, the hole transporting group is selected from carbazoles, biscarbazoles, indenocarbazoles, indolocarbazoles, amines, triarylamines, fluoreneamines and spirobifluoreneamines.

Further preferably, the hole transporting group HT is a group

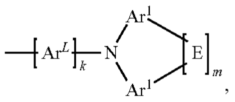

wherein $Ar^L$ is, identically or differently on each occurrence, selected from aromatic ring systems having 6 to 40 aromatic ring atoms, which may be substituted by one or more radicals $R^4$, and heteroaromatic ring systems having 5 to 40 aromatic ring atoms, which may be substituted by one or more radicals $R^4$;

$Ar^1$ is, identically or differently on each occurrence, selected from aromatic ring systems having 6 to 40 aromatic ring atoms, which may be substituted by one or more radicals $R^4$, and heteroaromatic ring systems having 5 to 40 aromatic ring atoms, which may be substituted by one or more radicals $R^4$;

E is a single bond or is a divalent group selected from —$C(R^4)_2$—, —$N(R^4)$—, —O—, and —S—; and k is on each occurrence, identically or differently, 0 or 1; where in the case of k=0, the group $Ar^L$ is not present and the nitrogen atom and the linker group are directly connected;

m is on each occurrence, identically or differently, 0 or 1, where in the case of m=0, the group E is not present and the groups $Ar^1$ are not connected;

$R^4$ is, identically or differently at each occurrence, selected from H, D, F, C(=O)$R^5$, CN, $Si(R^5)_3$, $N(R^5)_2$, P(=O)$(R^5)_2$, $OR^5$, S(=O)$R^5$, $S(=O)_2R^5$, straight-chain alkyl or alkoxy groups having 1 to 20 C atoms, branched or cyclic alkyl or alkoxy groups having 3 to 20 C atoms, alkenyl or alkynyl groups having 2 to 20 C atoms, aromatic ring systems having 6 to 40 aromatic ring atoms, and heteroaromatic ring systems having 5 to 40 aromatic ring atoms; where two or more radicals $R^4$ may be connected to each other to form a ring; where the said alkyl, alkoxy, alkenyl and alkynyl groups and the said aromatic and heteroaromatic ring systems may in each case be substituted by one or more radicals $R^5$, and where one or more $CH_2$ groups in the said alkyl, alkoxy, alkenyl and alkynyl groups may in each case be replaced by —$R^5C$=$CR^5$—, —C≡O—, $Si(R^5)_2$, C=O, C=$NR^5$, —C(=O)O—, —C(=O)$NR^5$—, $NR^5$, P(=O)($R^5$), —O—, —S—, SO or $SO_2$;

$R^5$ is, identically or differently at each occurrence, selected from H, D, F, C(=O)$R^6$, CN, $Si(R^6)_3$, $N(R^6)_2$, P(=O)$(R^6)_2$, $OR^6$, S(=O)$R^6$, $S(=O)_2R^6$, straight-chain alkyl or alkoxy groups having 1 to 20 C atoms, branched or cyclic alkyl or alkoxy groups having 3 to 20 C atoms, alkenyl or alkynyl groups having 2 to 20 C atoms, aromatic ring systems having 6 to 40 aromatic ring atoms, and heteroaromatic ring systems having 5 to 40 aromatic ring atoms; where two or more radicals $R^5$ may be connected to each other to form a ring; where the said alkyl, alkoxy, alkenyl and alkynyl groups and the said aromatic and heteroaromatic ring systems may in each case be substituted by one or more radicals $R^6$, and where one or more $CH_2$ groups in the said alkyl, alkoxy, alkenyl and alkynyl groups may in each case be replaced by —$R^6C$=$CR^6$—, —C≡O—, $Si(R^6)_2$, C=O, C=$NR^6$, —C(=O)O—, —C(=O)$NR^6$—, $NR^6$, P(=O)($R^6$), —O—, —S—, SO or $SO_2$; and $R^6$ is selected, identically or differently at each occurrence, from H, D, F, CN, alkyl groups having 1 to 20 C atoms, aromatic ring systems having 6 to 40 C atoms, and heteroaromatic ring systems having 5 to 40 aromatic ring atoms; where two or more radicals $R^6$ may be connected to each other to form a ring; and where the said alkyl groups, aromatic ring systems and heteroaromatic ring systems may be substituted by F and CN.

Group $Ar^L$ is a divalent group. Preferably, group $Ar^L$ is selected from aromatic ring systems having 6 to 30 aromatic ring atoms, which may be substituted by one or more radicals $R^4$. It is particularly preferred if $Ar^L$ is selected from divalent groups derived from benzene, biphenyl, terphenyl, naphthyl, fluorenyl, indenofluorenyl, spirobifluorenyl, dibenzofuranyl, dibenzothiophenyl, and carbazolyl, which may each be substituted by one or more radicals $R^4$. Most preferably, $Ar^L$ is a divalent group derived from benzene, which may be substituted by one or more radicals $R^4$.

According to a further embodiment, index k is 0, meaning that the group $Ar^L$ is not present, so that the linker group and the nitrogen atom of the amine are directly connected with each other.

Particularly preferred groups $Ar^1$ are, identically or differently, selected from phenyl, biphenyl, terphenyl, quaterphenyl, naphthyl, fluorenyl, especially 9,9'-dimethylfluorenyl and 9,9'-diphenylfluorenyl, benzofluorenyl, spirobifluorenyl, indenofluorenyl, dibenzofuranyl, dibenzothiophenyl, carbazolyl, benzofuranyl, benzothiophenyl, benzofused dibenzofuranyl, benzofused dibenzothiophenyl, naphthyl-substituted phenyl, fluorenyl-substituted phenyl, spirobifluorenyl-substituted phenyl, dibenzofuranyl-substituted phenyl, dibenzothiophenyl-substituted phenyl, carbazolyl-substituted phenyl, pyridyl-substituted phenyl, pyrimidyl-substituted phenyl, and triazinyl-substituted phenyl, each of which may optionally be substituted by one or more radicals $R^4$.

Preferably, groups $Ar^1$ are, at each occurrence, selected differently.

Preferred groups $Ar^1$ are, identically or differently, selected from groups of the following formulae Ar-1

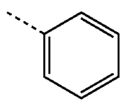

Ar-2

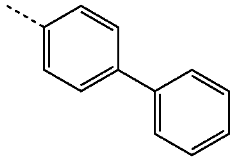

Ar-3

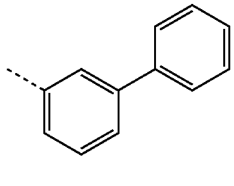

-continued
Ar-4
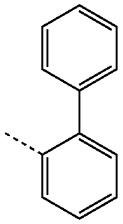
Ar-5
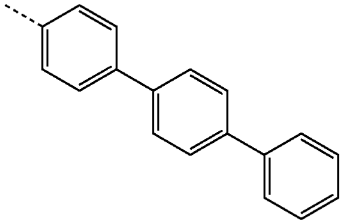
Ar-6
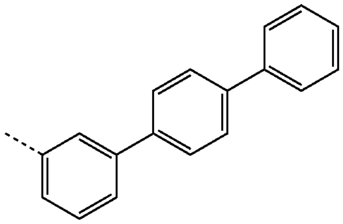
Ar-7
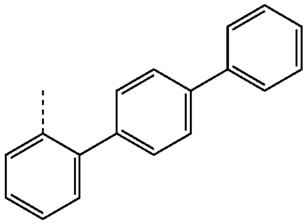
Ar-8
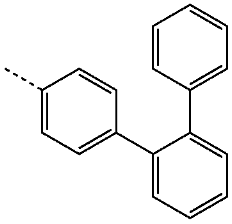
Ar-9
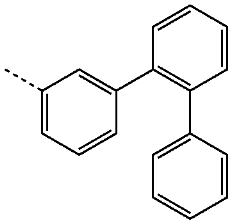
Ar-10
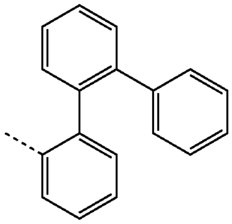
-continued
Ar-11
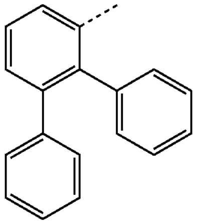
Ar-12
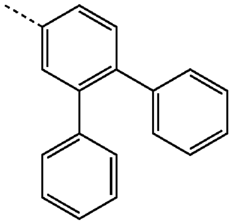
Ar-13
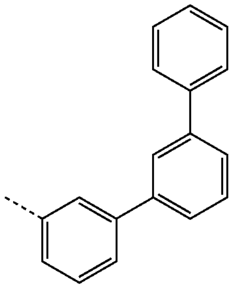
Ar-14
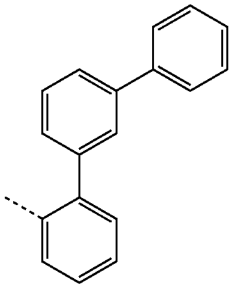
Ar-15
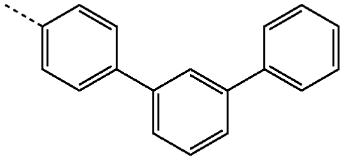
Ar-16
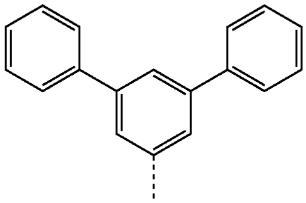
Ar-17
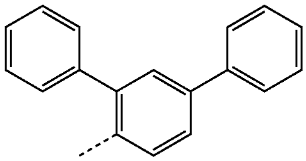

-continued
Ar-18
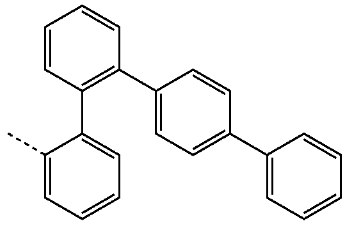
Ar-19
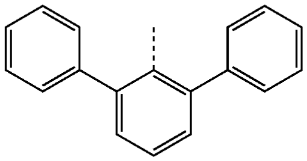
Ar-20
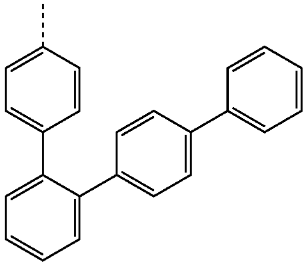
Ar-21
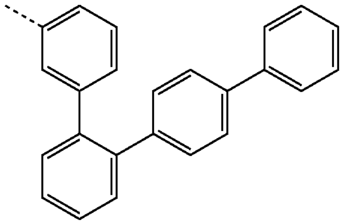
Ar-22
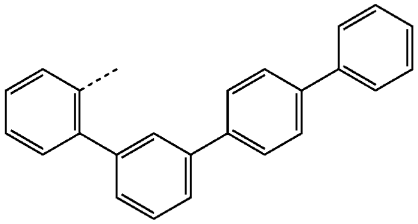
Ar-23
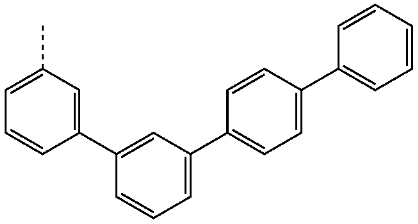
Ar-24
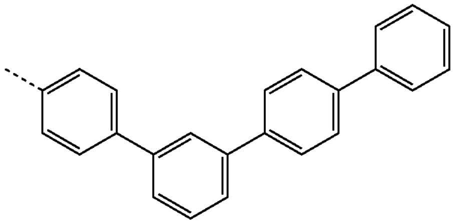
-continued
Ar-25
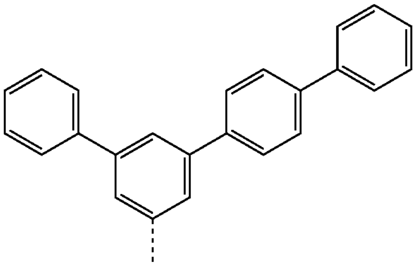
Ar-26
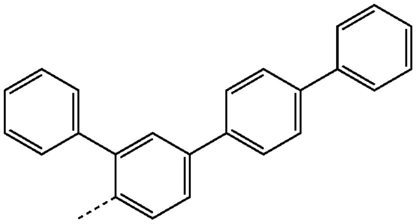
Ar-27
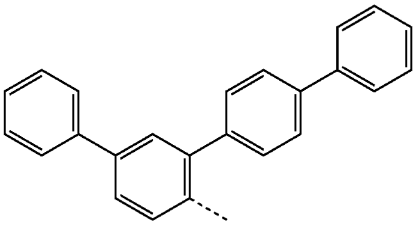
Ar-28
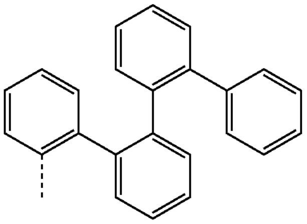
Ar-29
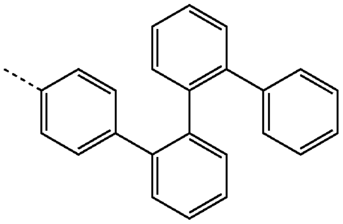
Ar-30
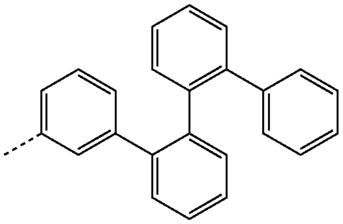

-continued
Ar-31
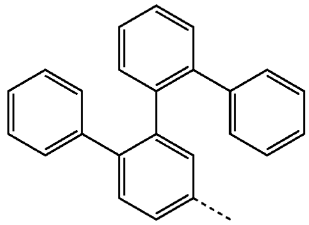
Ar-32
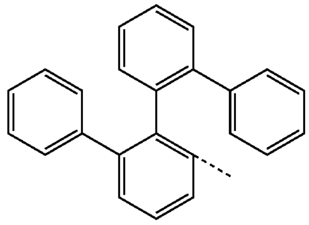
Ar-33
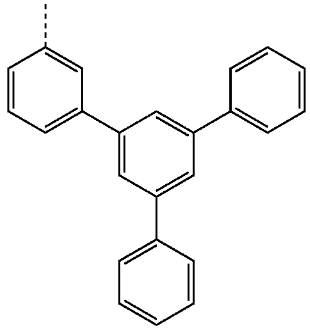
Ar-34
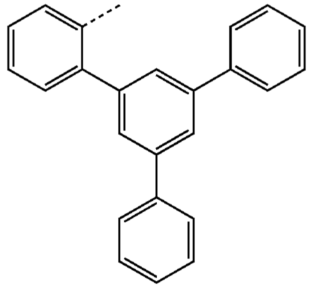
Ar-35
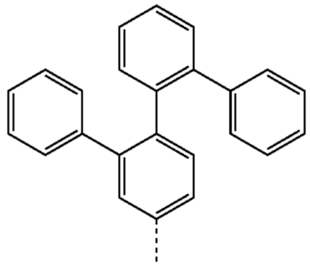
Ar-36
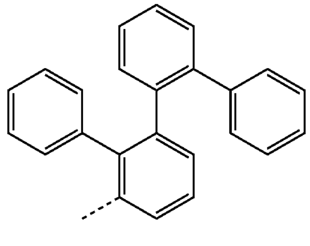
-continued
Ar-37
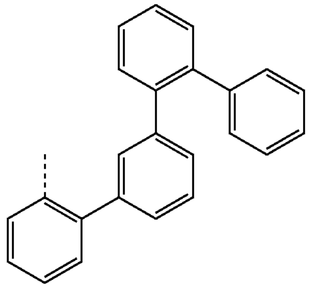
Ar-38
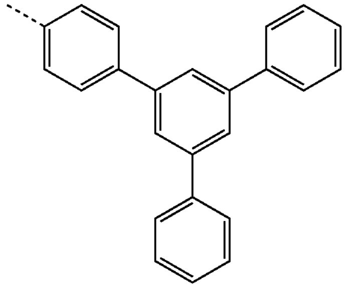
Ar-39
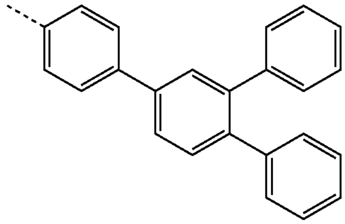
Ar-40
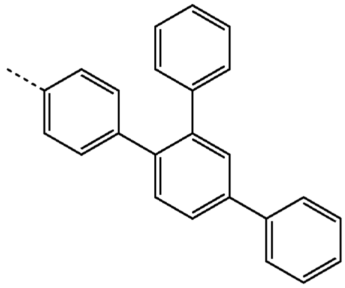
Ar-41
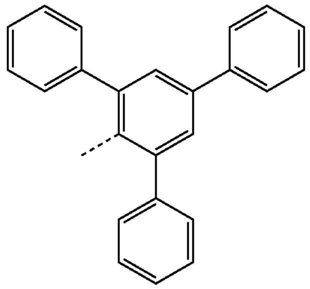
Ar-42
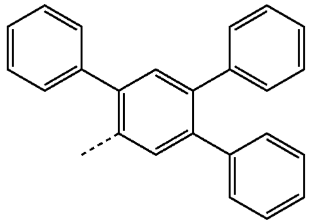

-continued
Ar-43
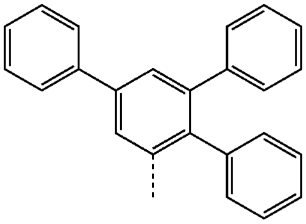
Ar-44
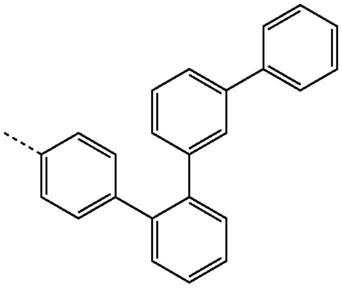
Ar-45
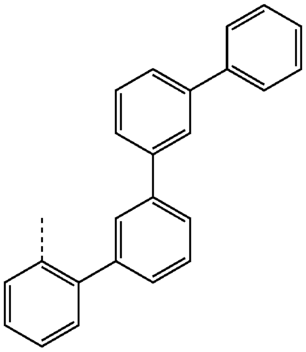
Ar-46
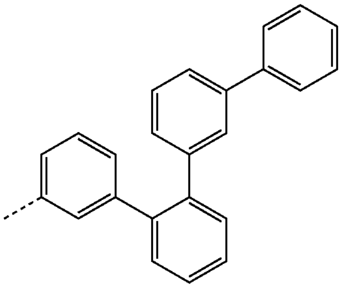
Ar-47
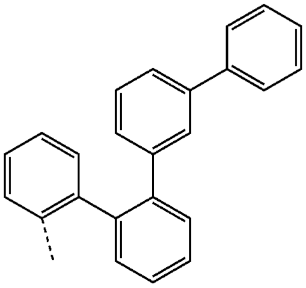
Ar-48
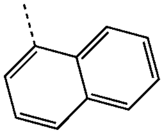
-continued
Ar-49
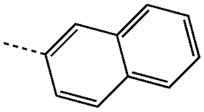
Ar-50
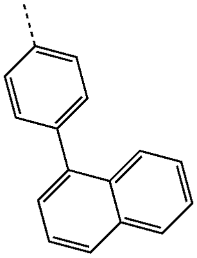
Ar-51
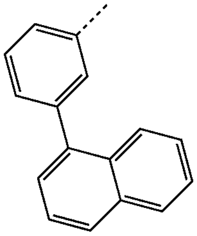
Ar-52
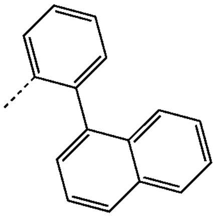
Ar-53
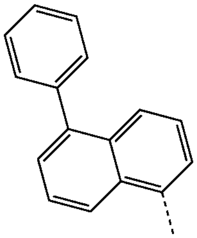
Ar-54
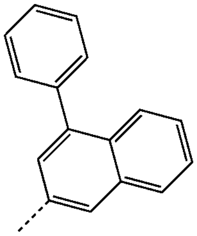
Ar-55
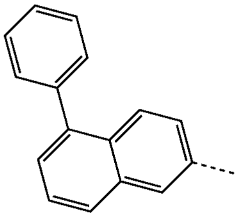

-continued
Ar-56
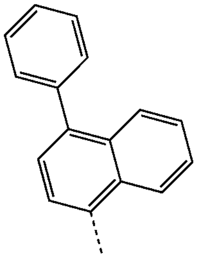
Ar-57
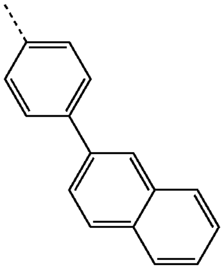
Ar-58
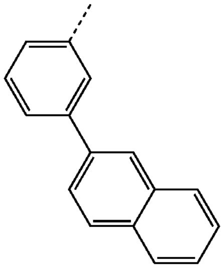
Ar-59
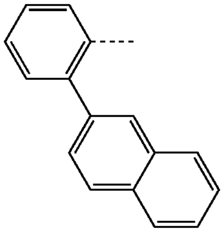
Ar-60
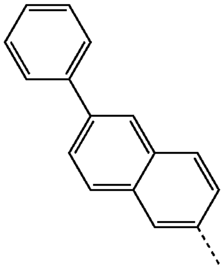
Ar-61
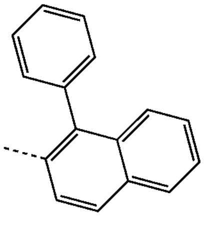
-continued
Ar-62
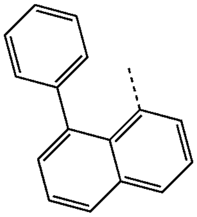
Ar-63
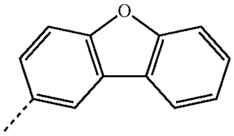
Ar-64
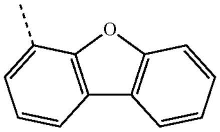
Ar-65
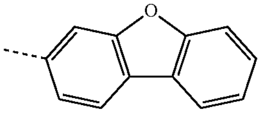
Ar-66
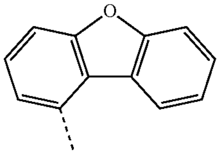
Ar-67
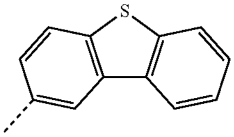
Ar-68
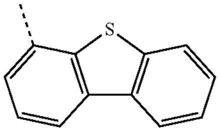
Ar-69
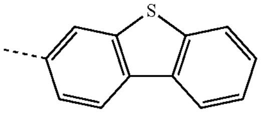
Ar-70
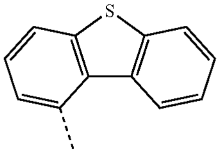
Ar-71
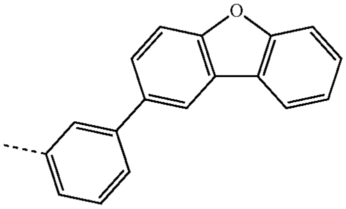

-continued
Ar-72
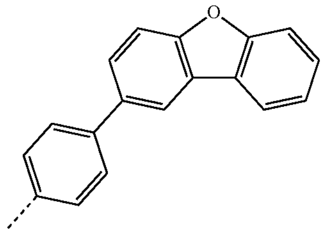
Ar-73
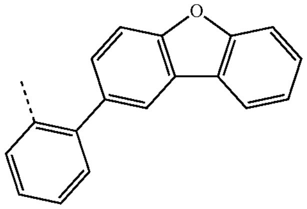
Ar-74
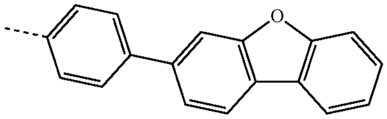
Ar-75
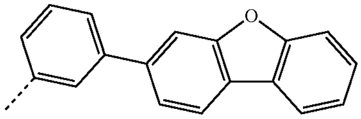
Ar-76
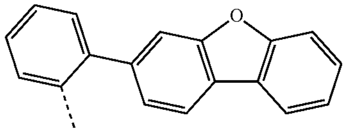
Ar-77
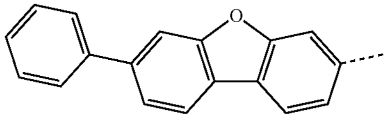
Ar-78
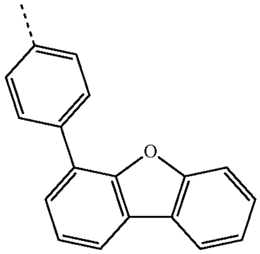
Ar-79
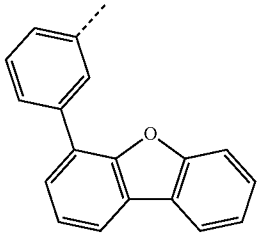
-continued
Ar-80
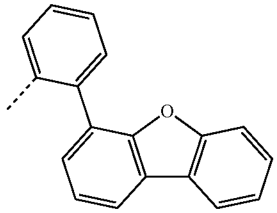
Ar-81
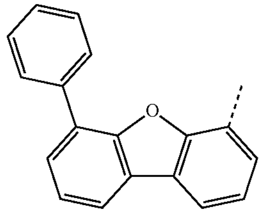
Ar-82
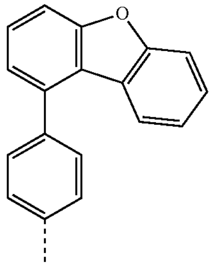
Ar-83
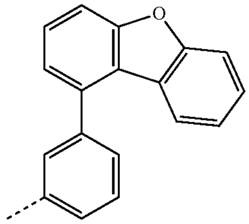
Ar-84
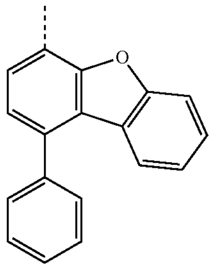
Ar-85
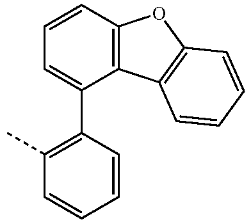

-continued
Ar-86
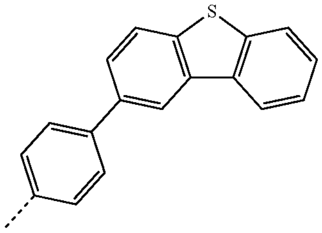
Ar-87
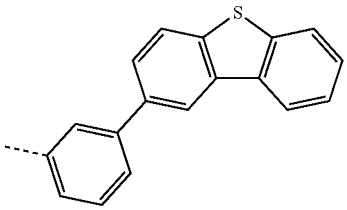
Ar-88
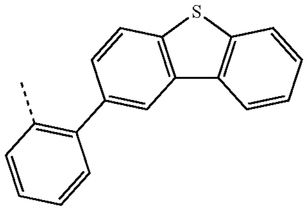
Ar-89
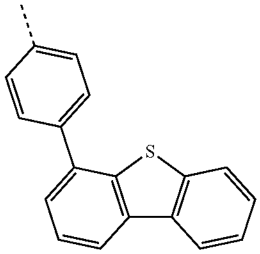
Ar-90
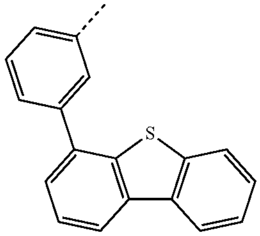
Ar-91
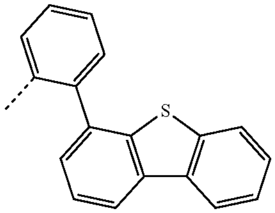
Ar-92
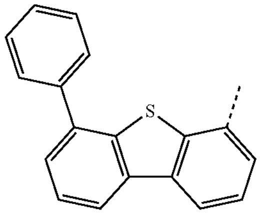
-continued
Ar-93
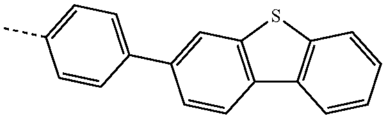
Ar-94
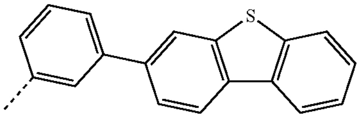
Ar-95
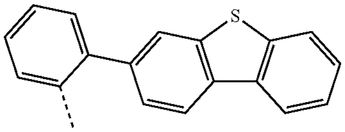
Ar-96
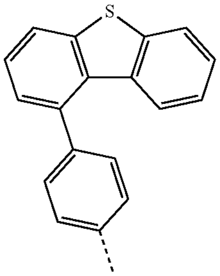
Ar-97
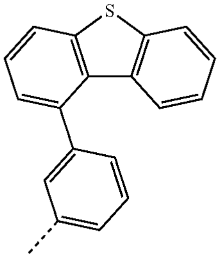
Ar-98
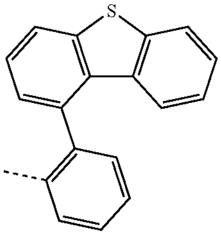
Ar-99
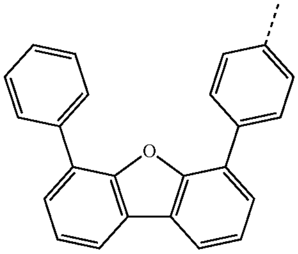

-continued
Ar-100
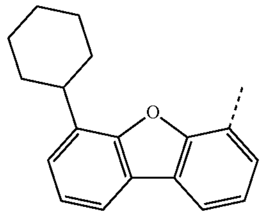
Ar-101
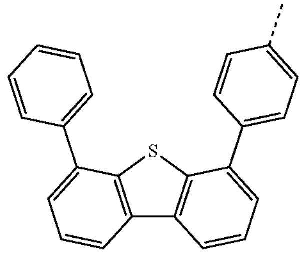
Ar-102
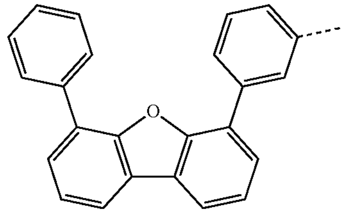
Ar-103
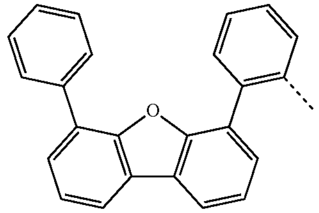
Ar-104
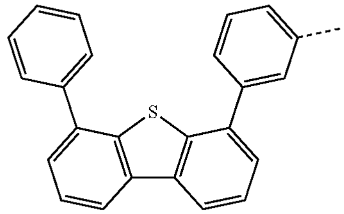
Ar-105
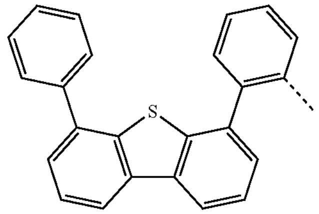
Ar-106
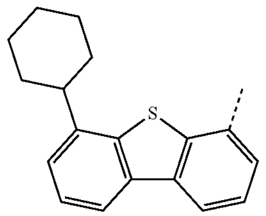
-continued
Ar-107
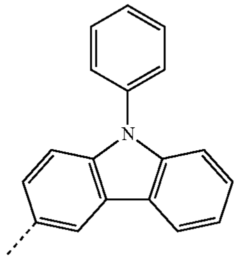
Ar-108
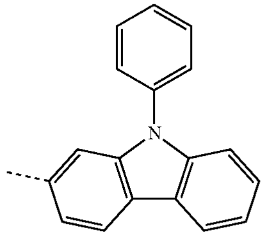
Ar-109
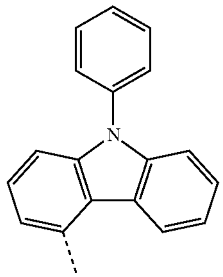
Ar-110
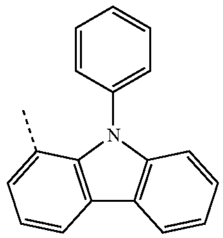
Ar-111
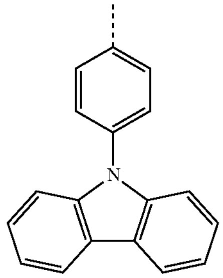
Ar-112
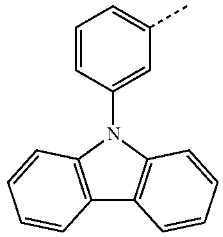

-continued
Ar-113
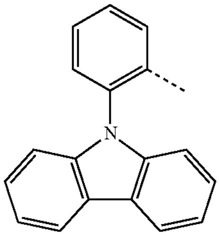
Ar-114
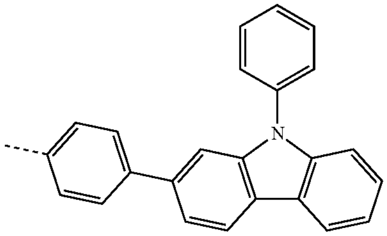
Ar-115
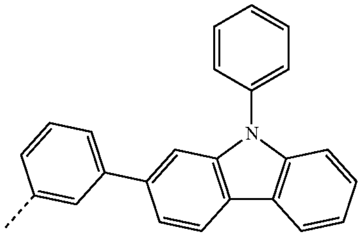
Ar-116
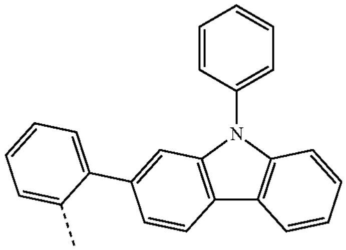
Ar-117
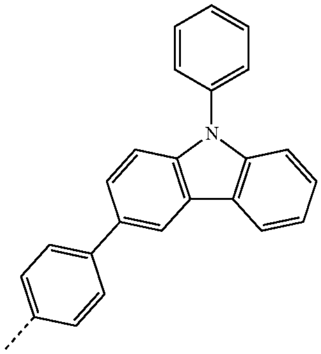
-continued
Ar-118
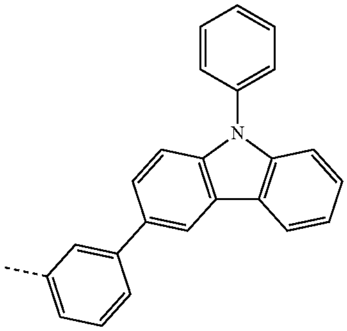
Ar-119
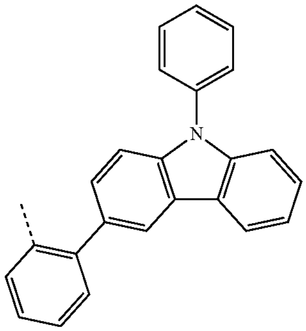
Ar-120
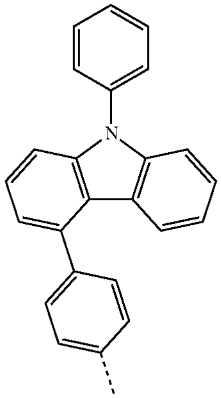
Ar-121
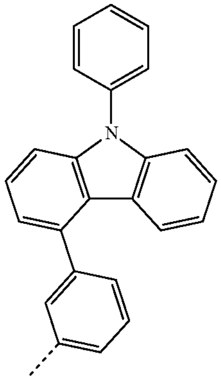

-continued
Ar-122
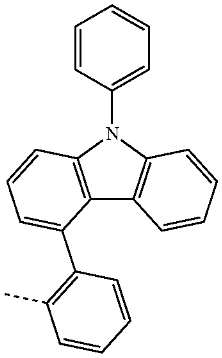
Ar-123
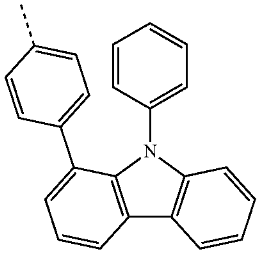
Ar-124
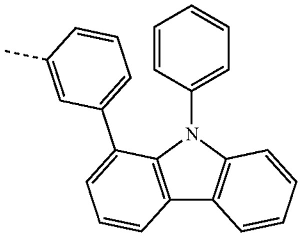
Ar-125
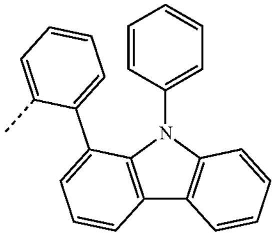
Ar-126
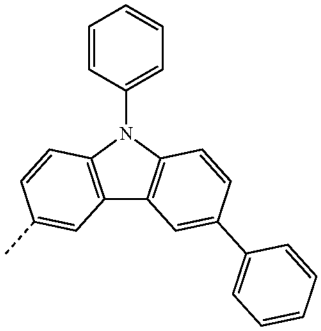
-continued
Ar-127
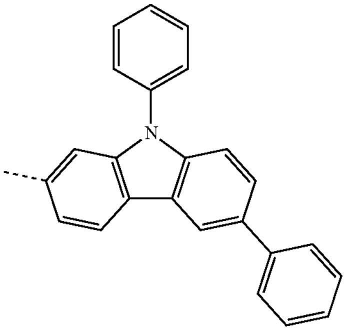
Ar-128
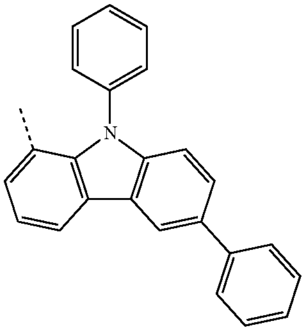
Ar-129
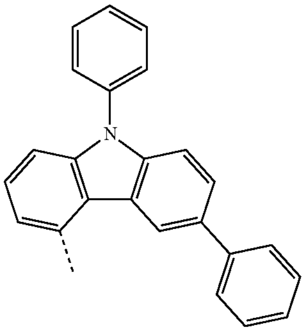
Ar-130
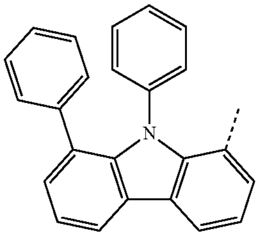
Ar-131
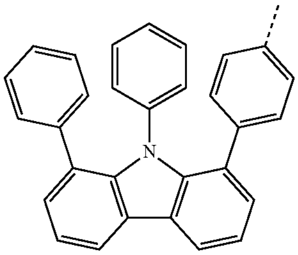

-continued
Ar-132
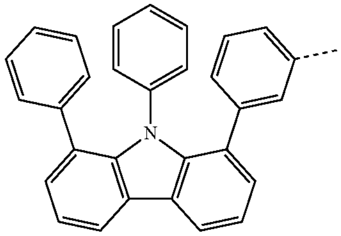
Ar-133
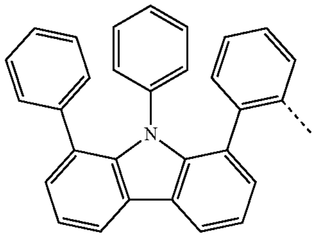
Ar-134
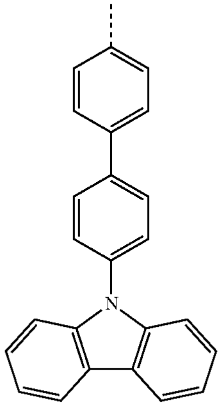
Ar-135
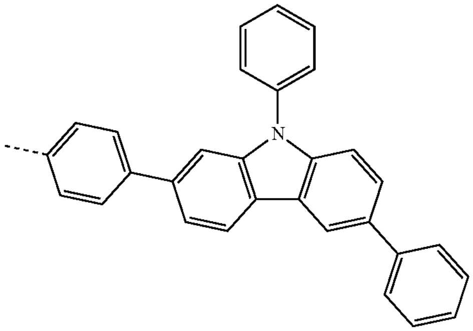
Ar-136
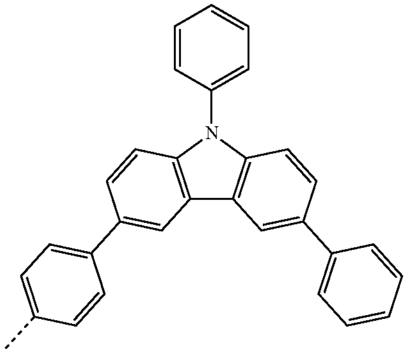
-continued
Ar-137
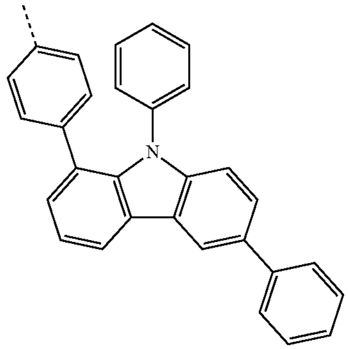
Ar-138
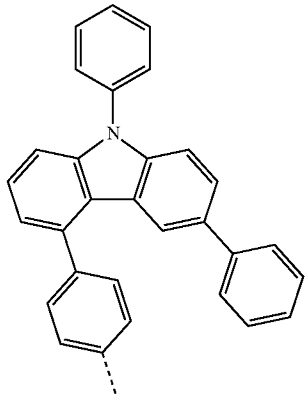
Ar-139
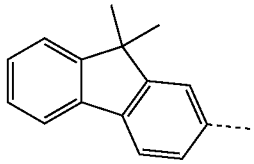
Ar-140
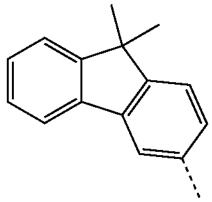
Ar-141
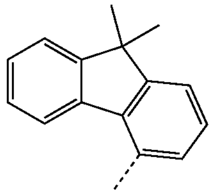
Ar-142
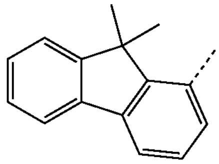

-continued
Ar-143
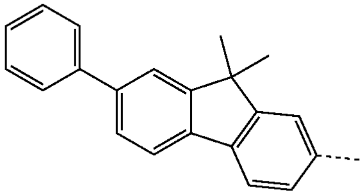
Ar-144
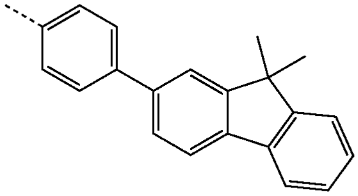
Ar-145
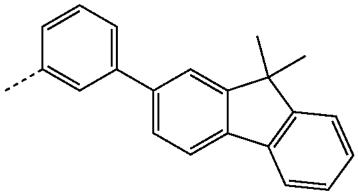
Ar-146
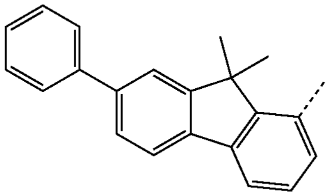
Ar-147
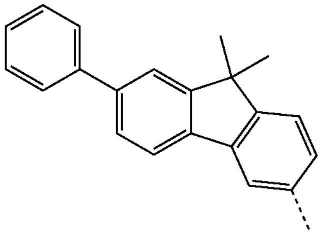
Ar-148
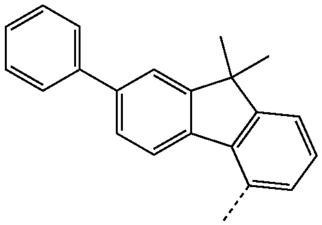
Ar-149
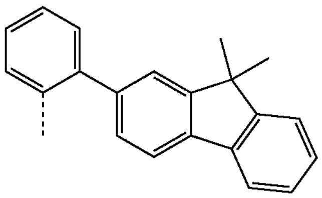
-continued
Ar-150
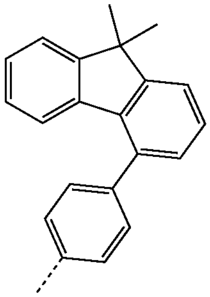
Ar-151
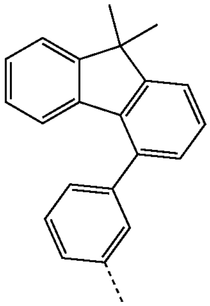
Ar-152
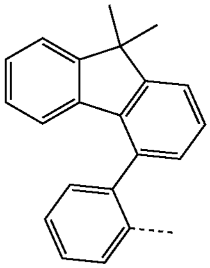
Ar-153
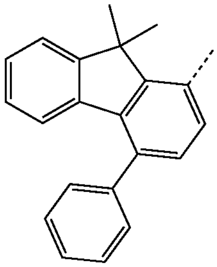
Ar-154
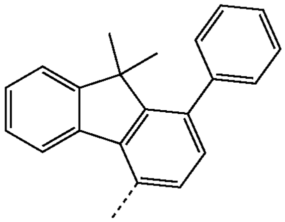
Ar-155
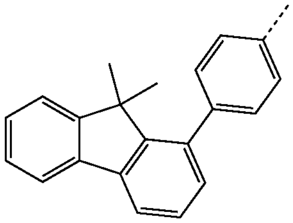

-continued
Ar-156
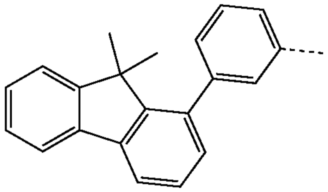
Ar-157
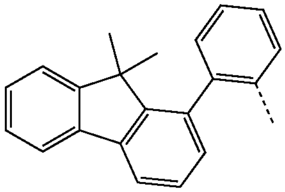
Ar-158
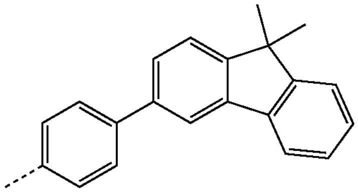
Ar-159
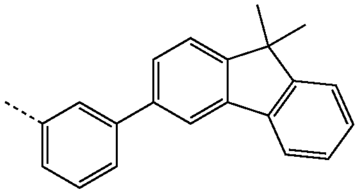
Ar-160
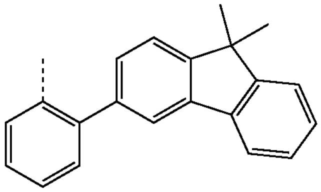
Ar-161
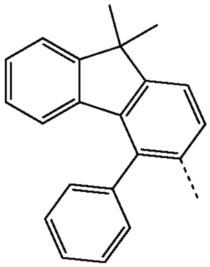
Ar-162
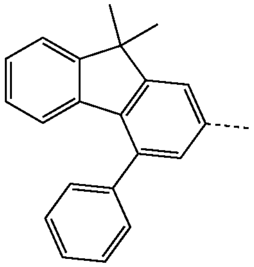
-continued
Ar-163
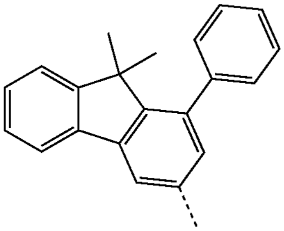
Ar-164
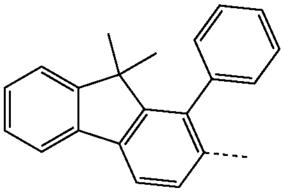
Ar-165
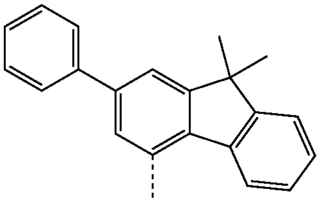
Ar-166
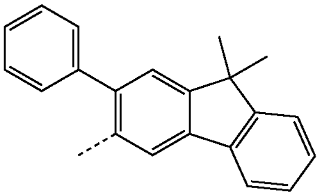
Ar-167
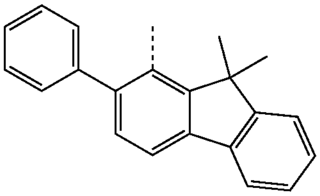
Ar-168
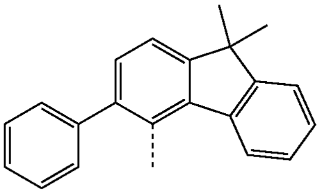
Ar-169
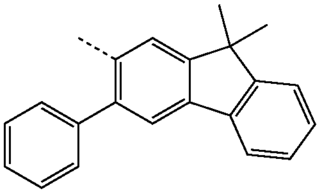

-continued
Ar-170
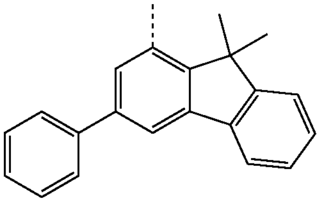
Ar-171
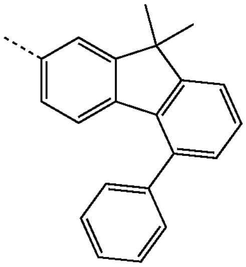
Ar-172
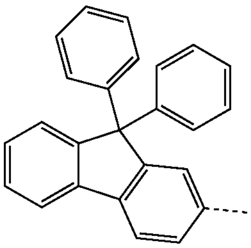
Ar-173
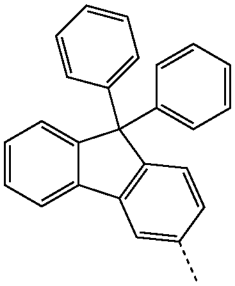
Ar-174
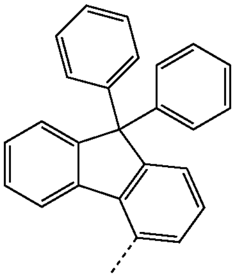
Ar-175
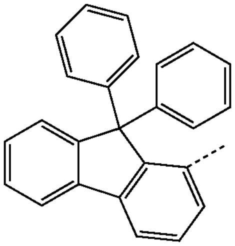
-continued
Ar-176
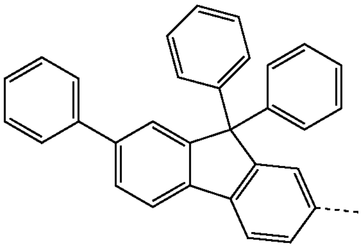
Ar-177
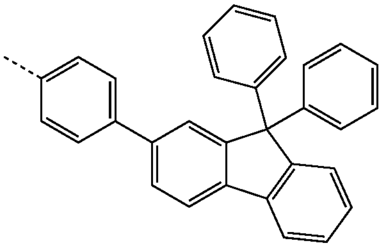
Ar-178
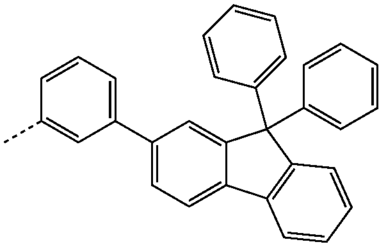
Ar-179
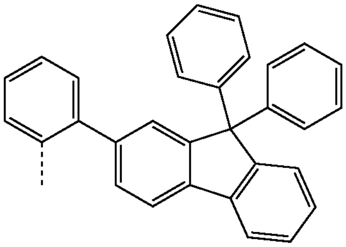
Ar-180
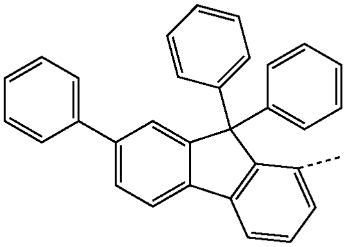
Ar-181
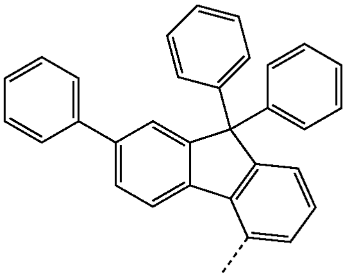

-continued
Ar-182
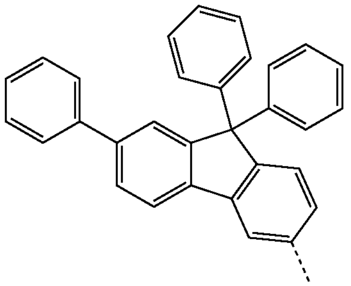
Ar-183
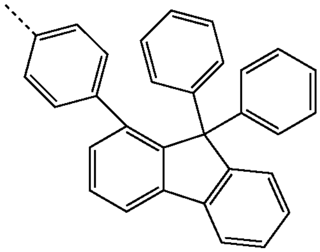
Ar-184
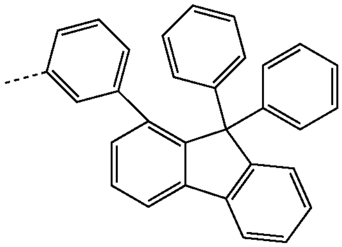
Ar-185
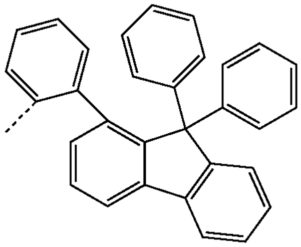
Ar-186
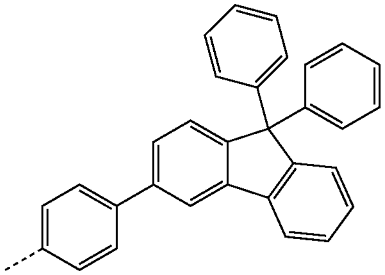
-continued
Ar-187
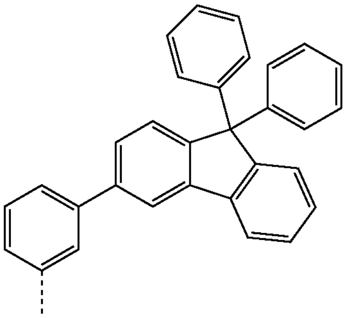
Ar-188
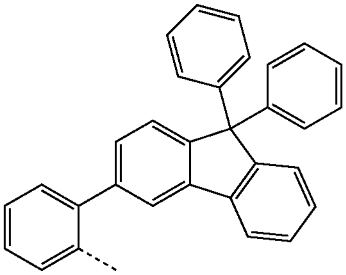
Ar-189
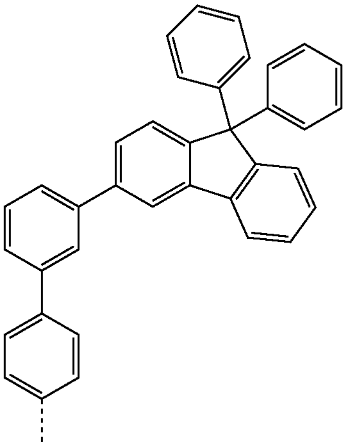
Ar-190
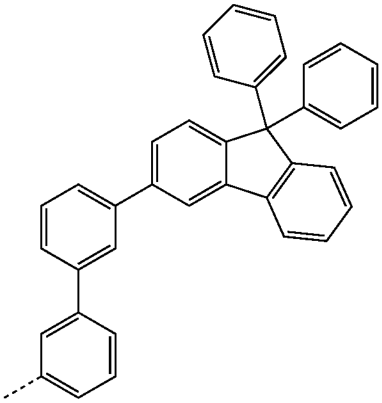

-continued
Ar-191
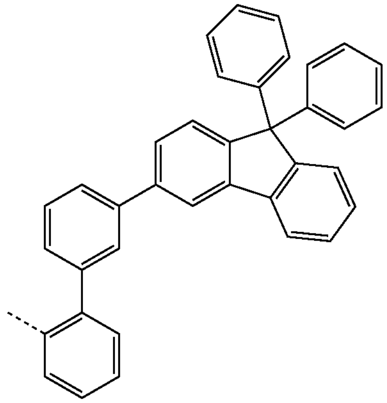
Ar-192
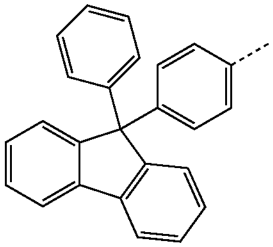
Ar-193
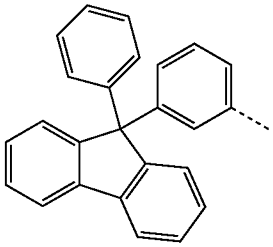
Ar-194
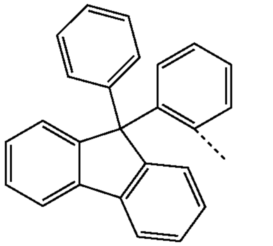
Ar-195
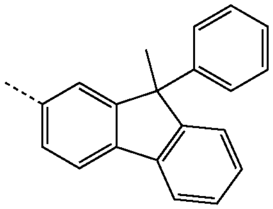
Ar-196
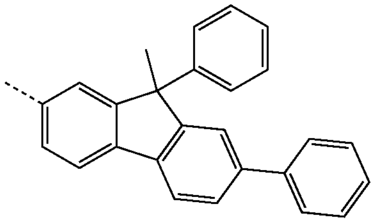
-continued
Ar-197
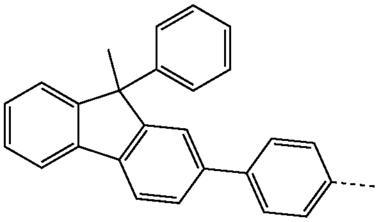
Ar-198
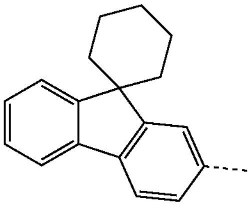
Ar-199
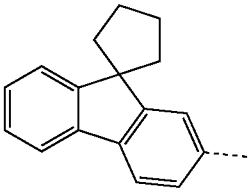
Ar-200
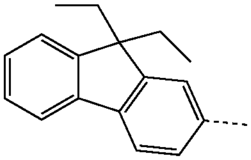
Ar-201
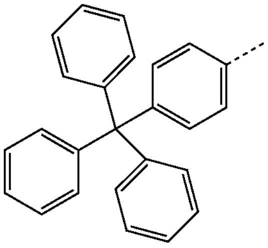
Ar-202
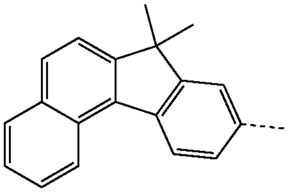
Ar-203
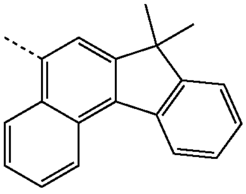

-continued
Ar-204
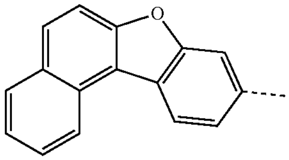
Ar-205
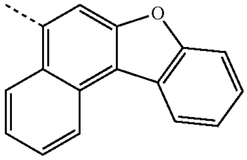
Ar-206
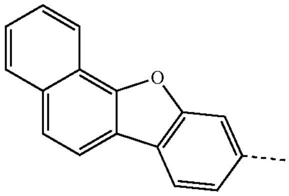
Ar-207
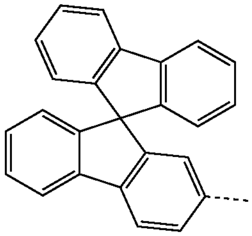
Ar-208
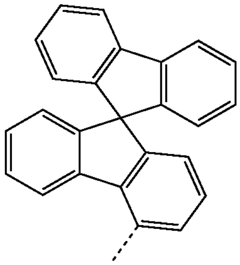
Ar-209
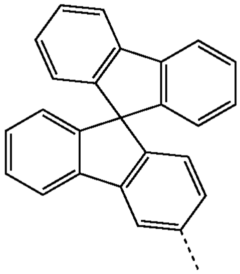
Ar-210
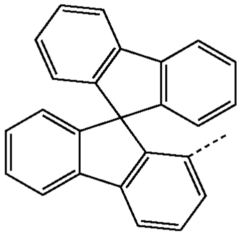
-continued
Ar-211
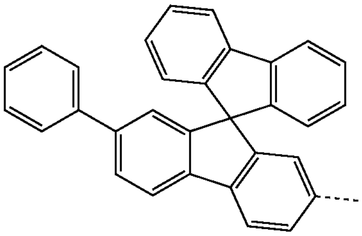
Ar-212
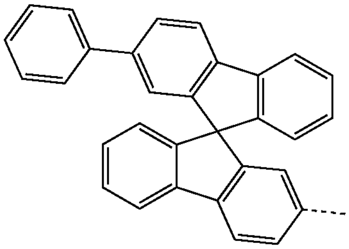
Ar-213
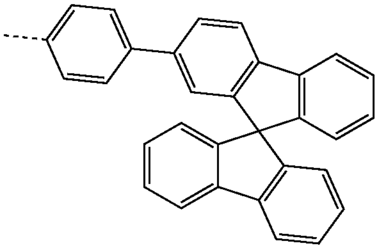
Ar-214
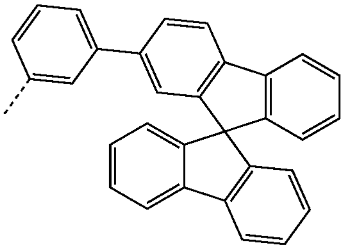
Ar-215
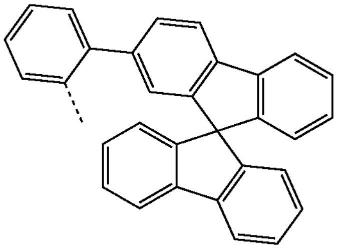
Ar-216
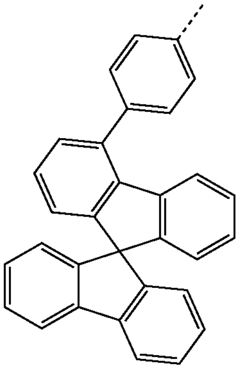

-continued
Ar-217
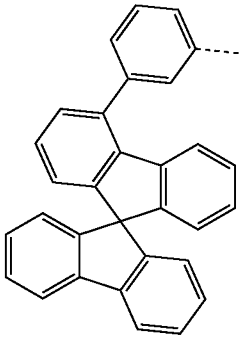
Ar-218
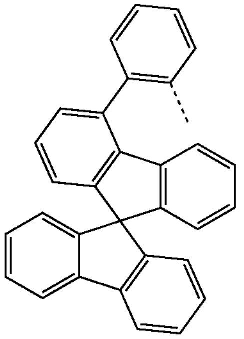
Ar-219
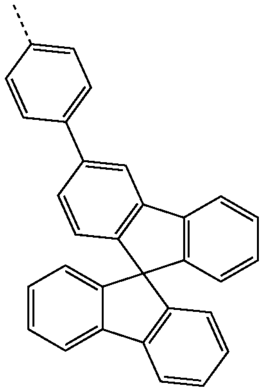
Ar-220
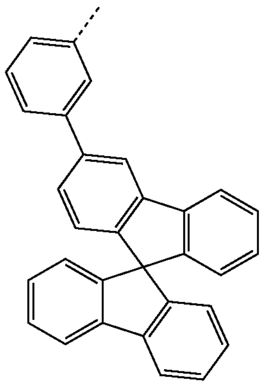
-continued
Ar-221
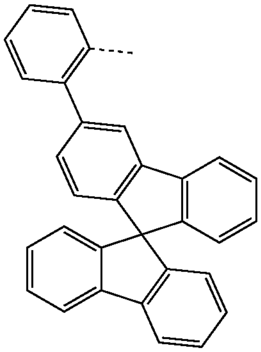
Ar-222
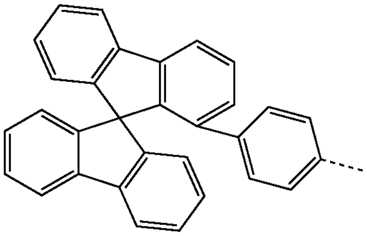
Ar-223
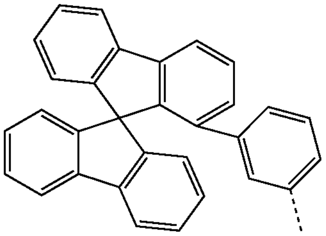
Ar-224
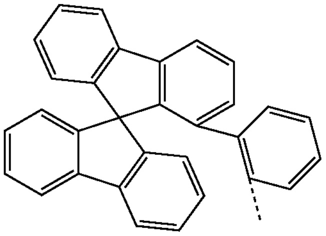
Ar-225
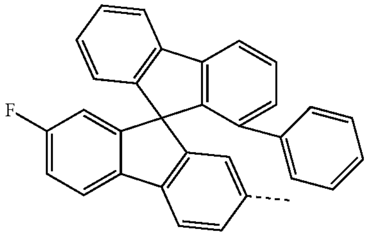
Ar-226
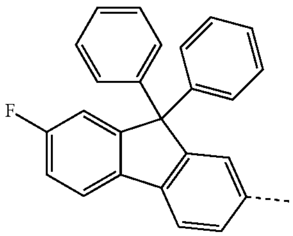

-continued
Ar-227
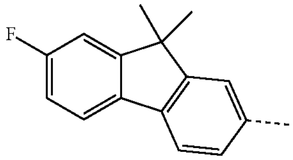
Ar-228
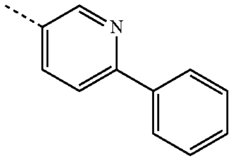
Ar-229
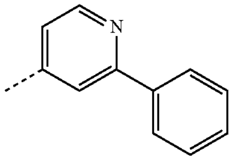
Ar-230
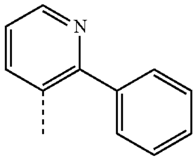
Ar-231
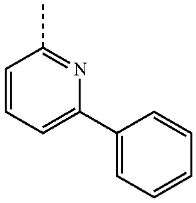
Ar-232
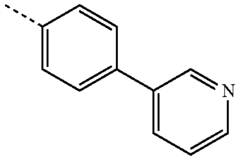
Ar-233
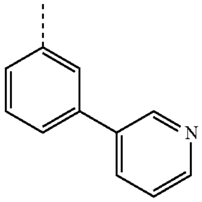
Ar-234
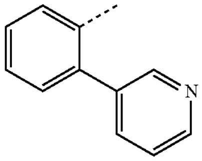
Ar-235
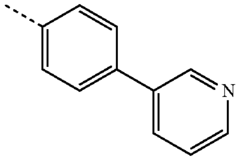
-continued
Ar-236
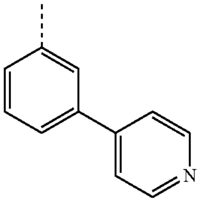
Ar-237
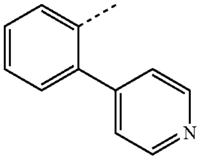
Ar-238
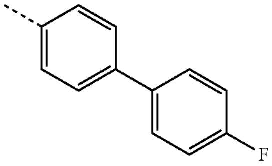
Ar-239
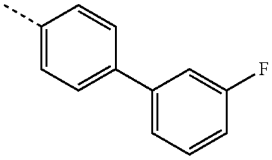
Ar-240
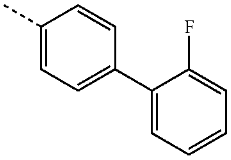
Ar-241
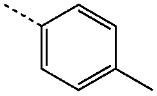
Ar-242
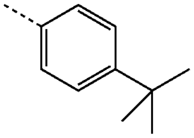
Ar-243
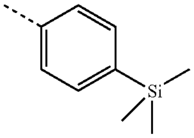
Ar-244
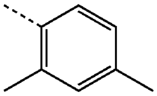
Ar-245
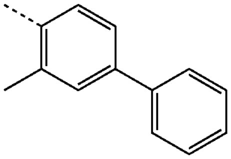

-continued

Ar-246

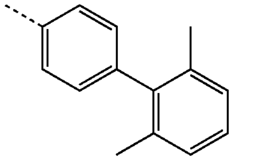

Ar-247

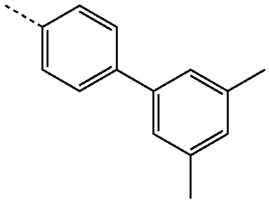

Ar-248

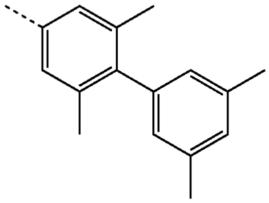

Ar-250

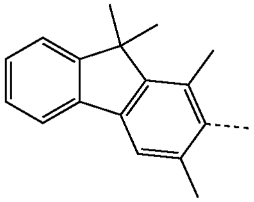

Ar-251

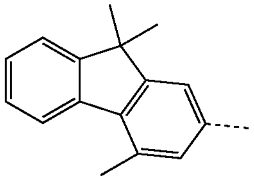

Ar-252

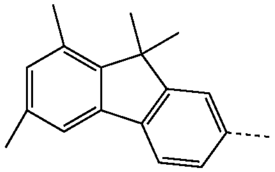

where the groups may be substituted at the free positions with groups $R^4$, but are preferably unsubstituted in these positions, and where the dotted line symbolizes the bonding position to the nitrogen atom.

According to a preferred embodiment, index m is 0, meaning that groups $Ar^1$ are not connected by a group E.

According to an alternative embodiment, which may be preferred under certain conditions, index m is 1, meaning that groups $Ar^1$ are connected by a group E.

In the case that groups $Ar^1$ are connected by a group E, it is preferred that groups $Ar^1$ are selected, identically or differently, from phenyl and fluorenyl, each of which may be substituted by one or more groups $R^4$.

Furthermore, in such case, it is preferred that the group E which connects the groups $Ar^1$ is located on the respective group $Ar^1$, preferably on the respective group $Ar^1$ which is phenyl or fluorenyl, in ortho-position to the bond of the group $Ar^1$ to the amine nitrogen atom. Furthermore, preferably, in such case a six-ring with the amine nitrogen atom is formed of the groups $Ar^1$ and E if E is selected from $C(R^4)_2$, $NR^4$, O and S; and a five-ring is formed if E is a single bond.

According to an alternative embodiment, which may be preferred under certain conditions, index m is 1, meaning that groups $Ar^1$ are connected by a group E.

In the case that groups $Ar^1$ are connected by a group E, it is preferred that groups $Ar^1$ are selected, identically or differently, from phenyl and fluorenyl, each of which may be substituted by one or more groups $R^4$.

Furthermore, in such case, it is preferred that the group E which connects the groups $Ar^1$ is located on the respective group $Ar^1$, preferably on the respective group $Ar^1$ which is phenyl or fluorenyl, in ortho-position to the bond of the group $Ar^1$ to the amine nitrogen atom. Furthermore, preferably, in such case a six-ring with the amine nitrogen atom is formed of the groups $Ar^1$ and E if E is selected from $C(R^4)_2$, $NR^4$, O and S; and a five-ring is formed if E is a single bond.

In the case that groups $Ar^1$ are connected by a group E, particularly preferred embodiments of the moieties

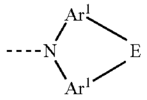

are selected from the following formulae

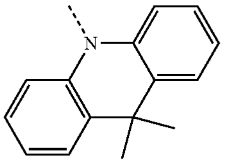

N-1

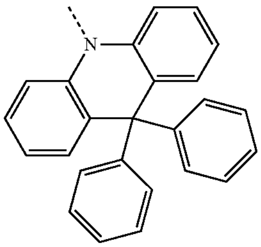

N-2

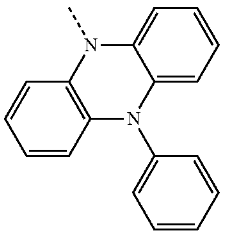

N-3

-continued
N-4
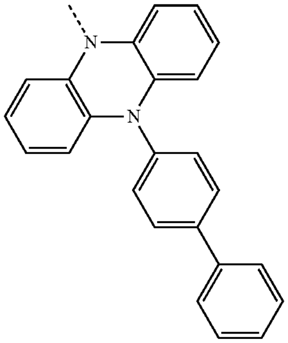
N-5
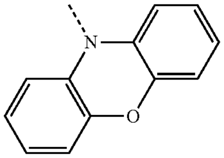
N-6
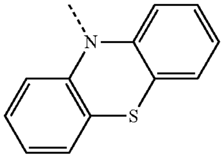
N-7
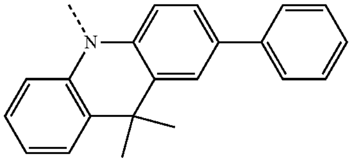
N-8
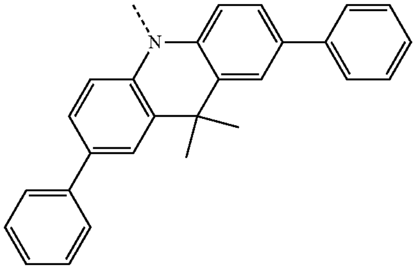
N-9
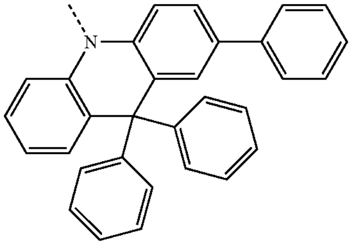
-continued
N-10
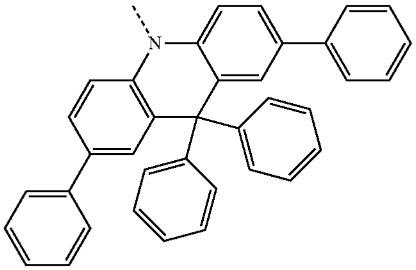
N-11
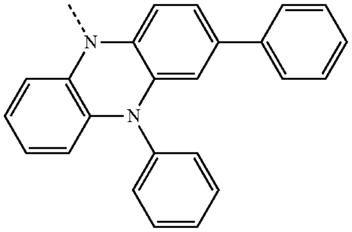
N-12
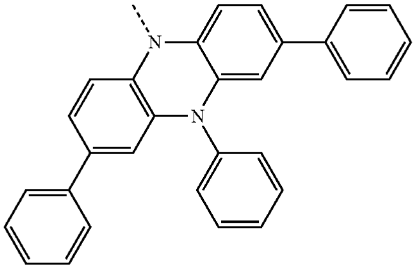
N-13
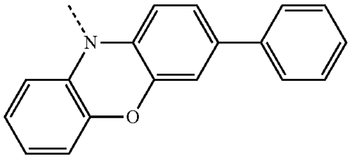
N-14
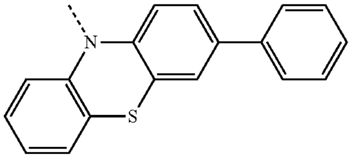
N-15
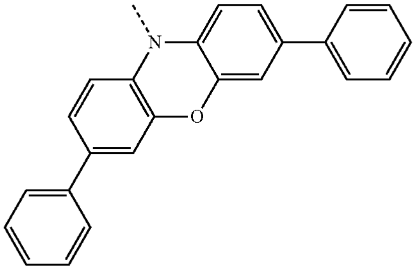

-continued
N-16
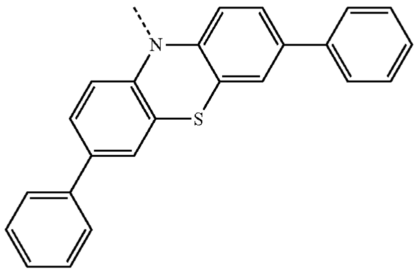
N-17
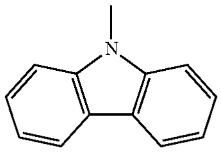
N-18
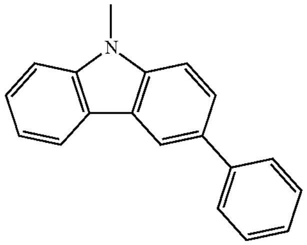
N-19
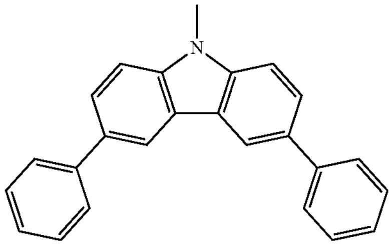
N-20
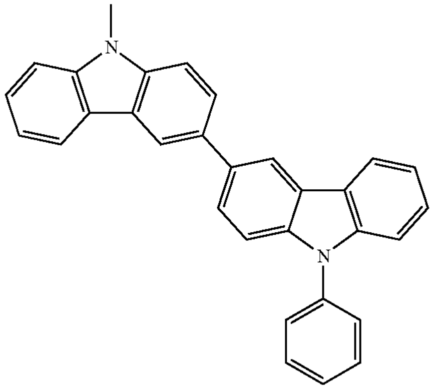
N-21
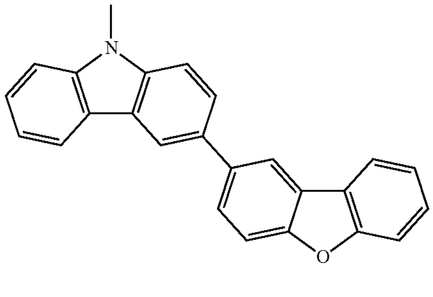
-continued
N-22
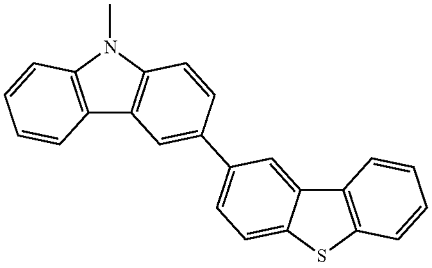
N-23
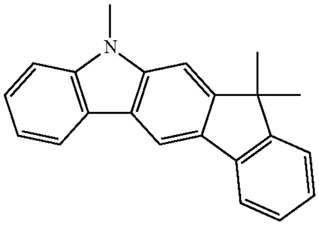
N-24
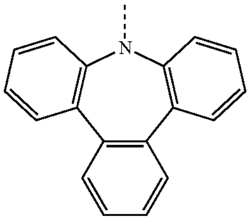
N-25
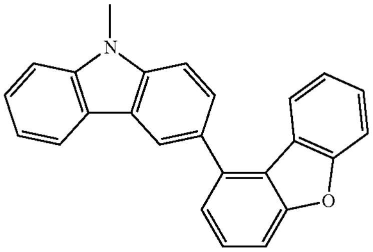
N-26
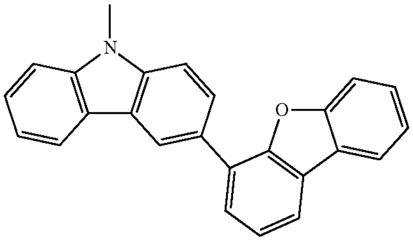
N-27
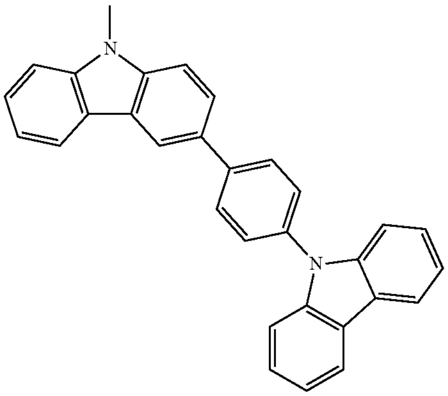

-continued

N-28

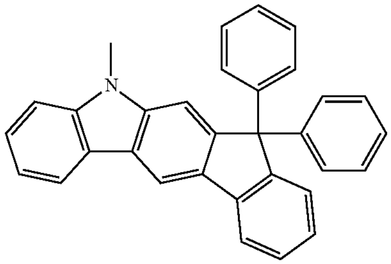

N-29

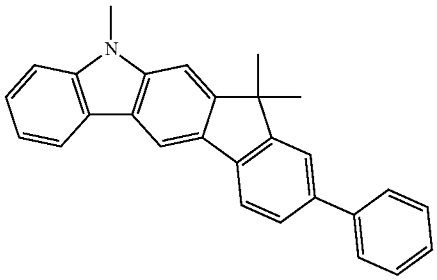

N-30

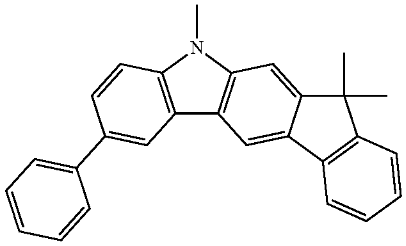

N-31

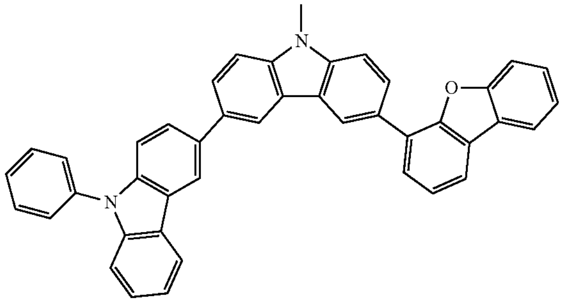

N-32

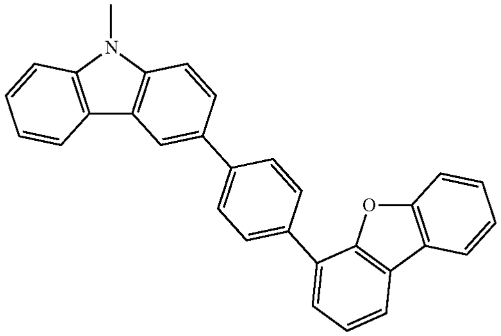

where the groups may be substituted at the free positions with groups $R^4$, but are preferably unsubstituted in these positions, and where the dotted line symbolizes the bonding position of the nitrogen atom to the linker group L, i.e., the alkylene group linking groups FG and X in formula (1) (in case k=0), or the bonding position to the group $Ar^L$ (in case k=1).

For the case m=0, particularly preferable moieties

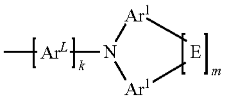

for hole transporting group HT conform to the following formulae

A-1

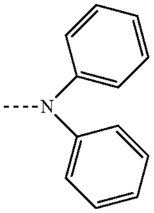

A-2

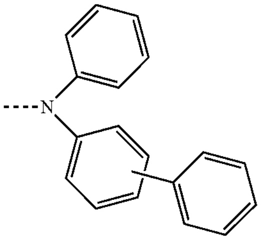

A-3

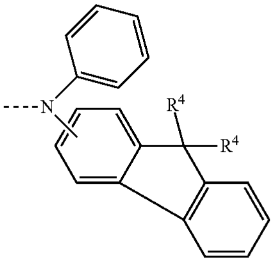

A-4

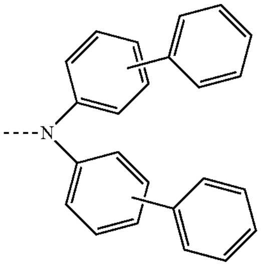

A-5

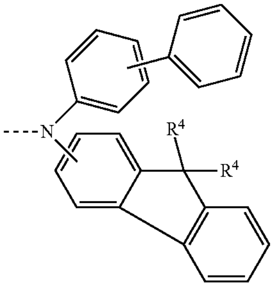

-continued
A-6
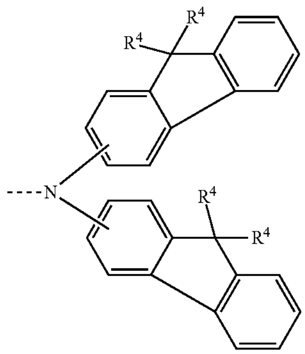
A-7
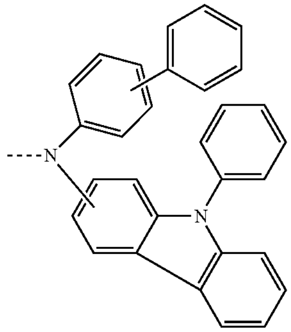
A-8
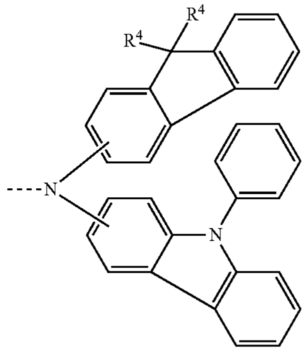
A-9
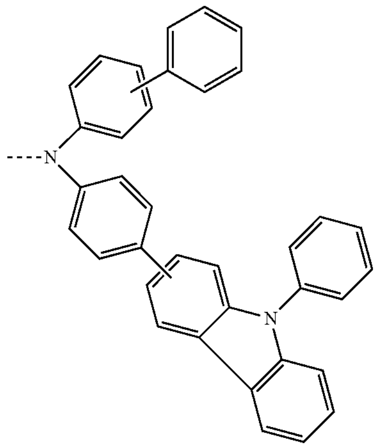
-continued
A-10
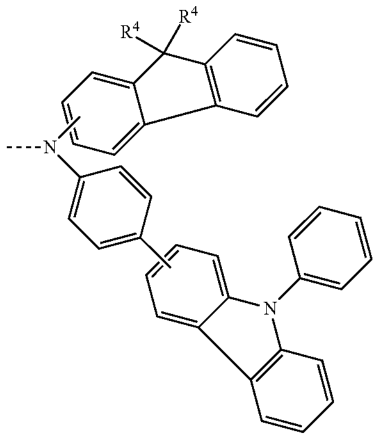
A-11
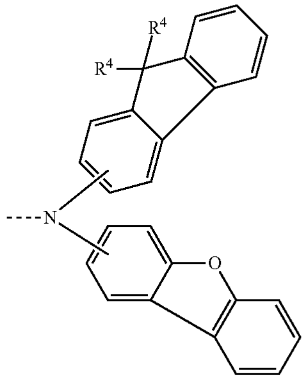
A-12
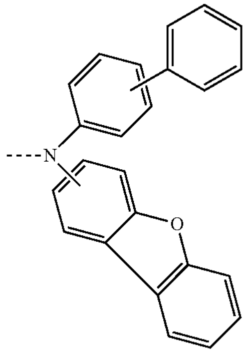
A-13
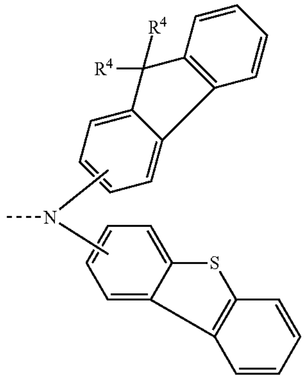

-continued
A-14
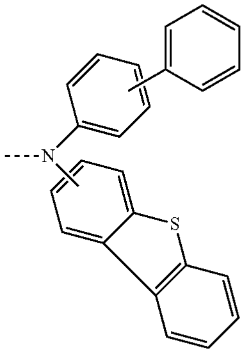
A-15
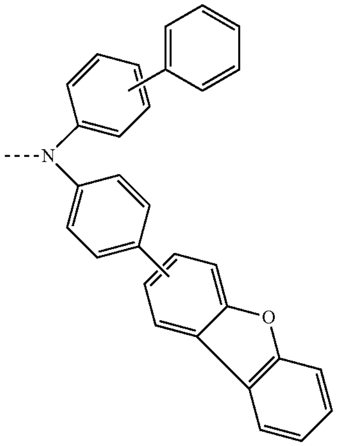
A-16
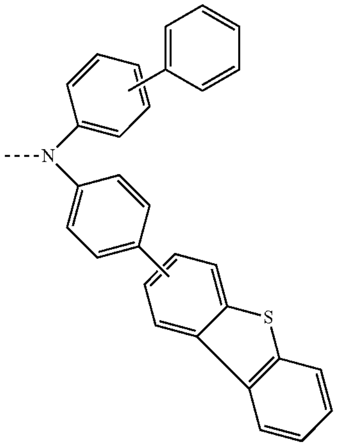
-continued
A-17
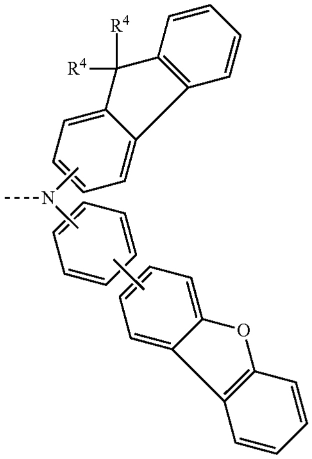
A-18
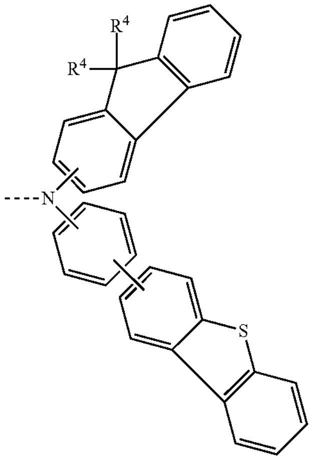
A-19
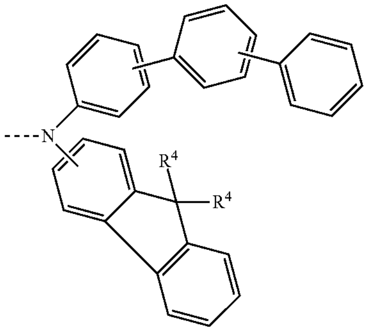
A-20
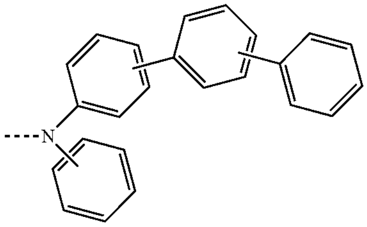

-continued
A-21
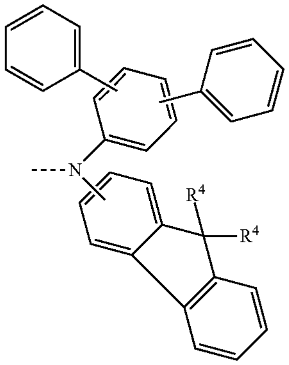
A-22
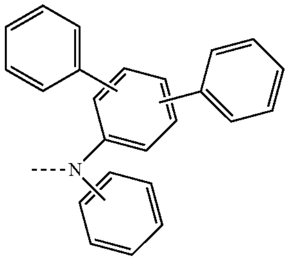
A-23
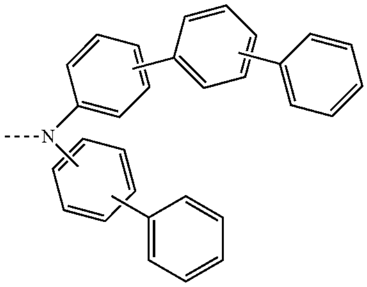
A-24
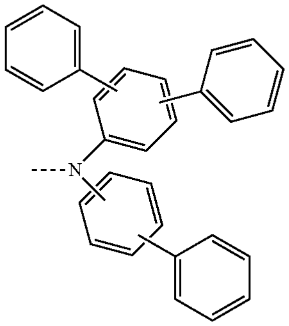
A-25
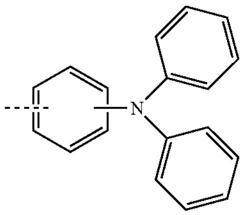
-continued
A-26
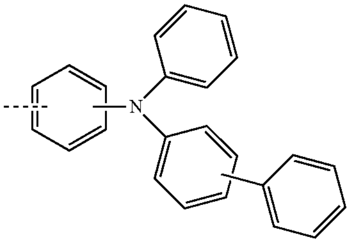
A-27
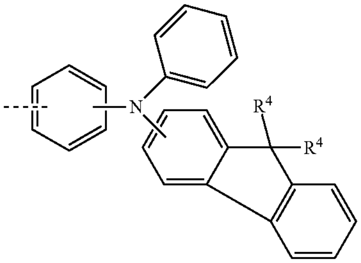
A-28
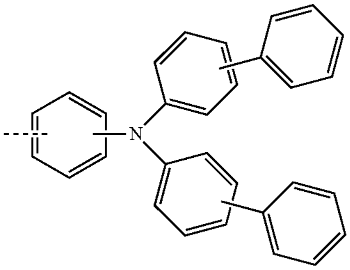
A-29
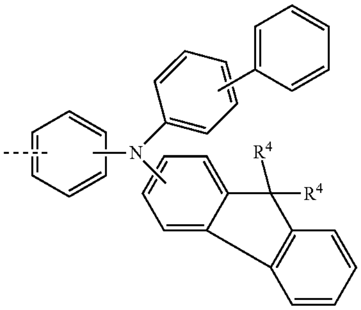
A-30
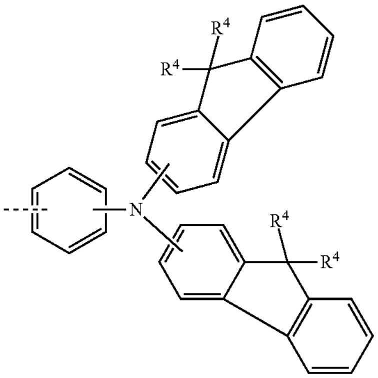

-continued
A-31
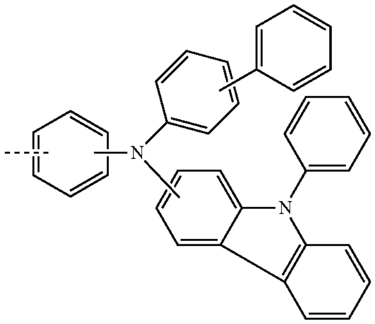
A-32
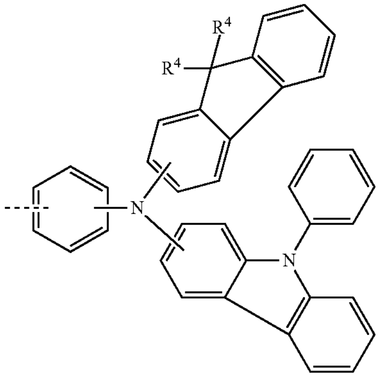
A-33
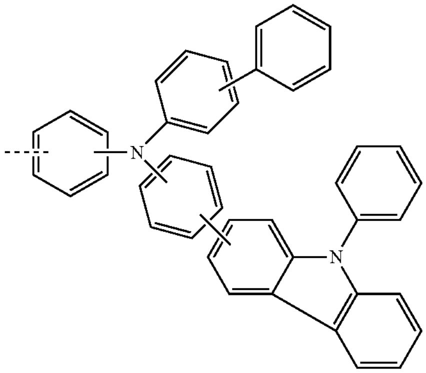
A-34
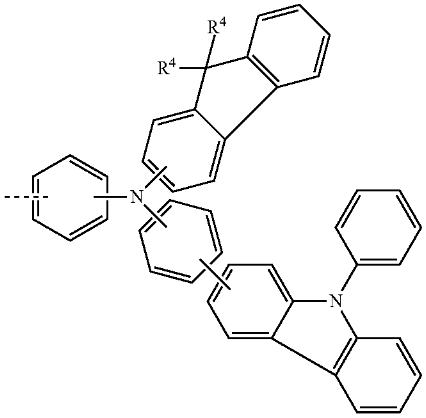
-continued
A-35
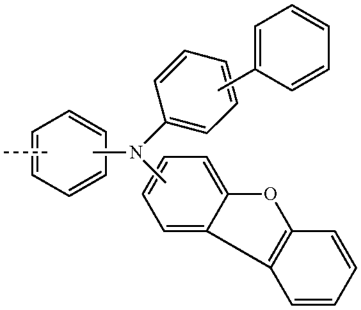
A-36
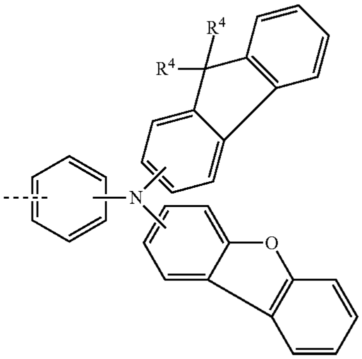
A-37
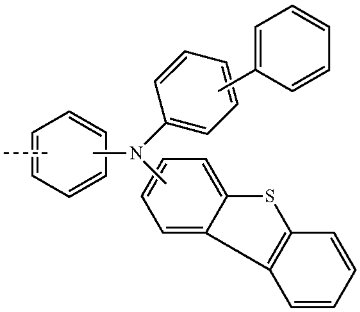
A-38
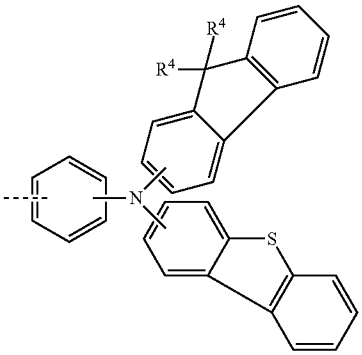

-continued
A-39
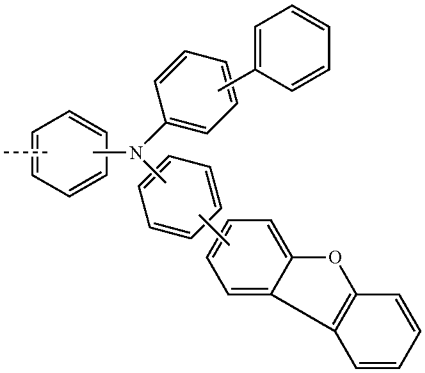
A-40
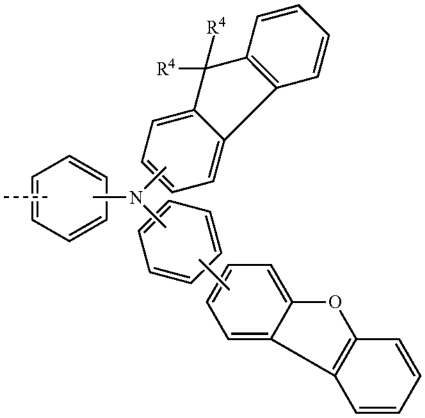
A-41
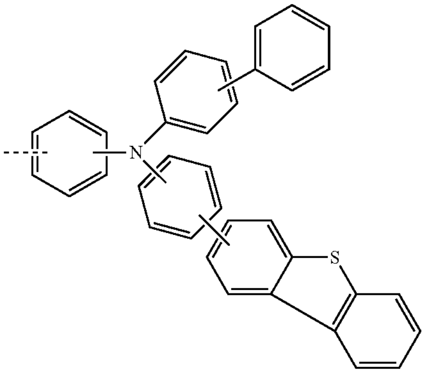
A-42
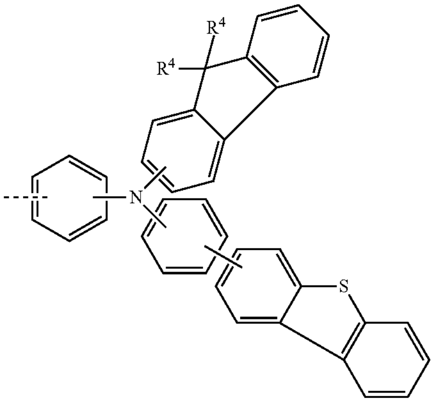
-continued
A-43
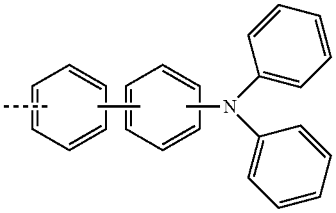
A-44
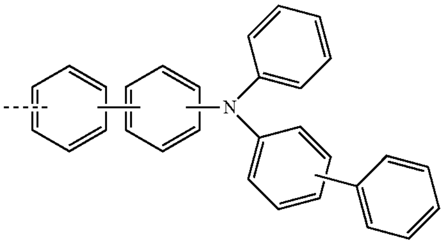
A-45
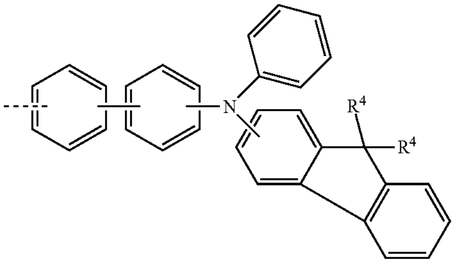
A-46
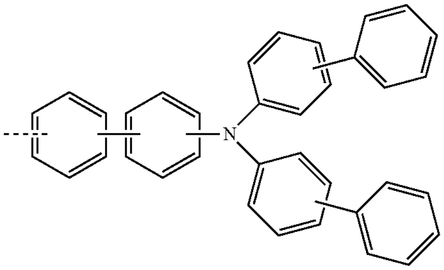
A-47
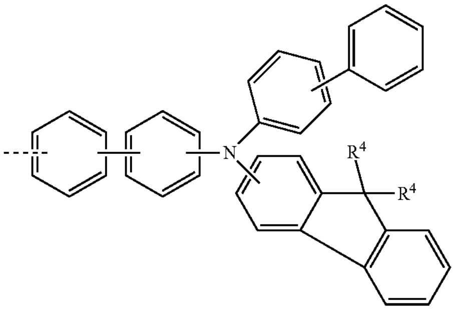

-continued

A-48

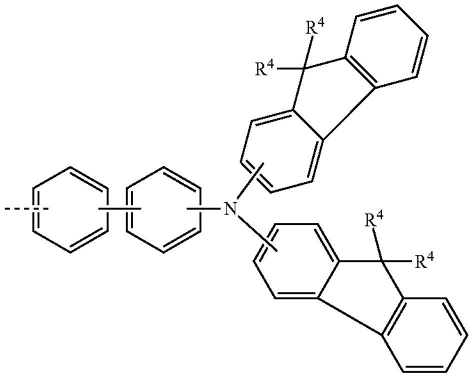

where the groups may be substituted at the free positions with groups $R^4$, but are preferably unsubstituted in these positions, and where the dotted line symbolizes the bonding position to the linker group L, i.e., the alkylene group linking groups FG and X in formula (1).

Groups $R^4$ are preferably selected, identically or differently, from H, F, CN, $Si(R^5)_3$, straight-chain alkyl groups having 1 to 20 C atoms, branched or cyclic alkyl groups having 3 to 20 C atoms, aromatic ring systems having 6 to 40 aromatic ring atoms, and heteroaromatic ring systems having 5 to 40 aromatic ring atoms; where two or more radicals $R^4$ may be connected to each other to form a ring; where the said alkyl groups and the said aromatic and heteroaromatic ring systems may in each case be substituted by one or more radicals $R^5$.

Groups $R^5$ are preferably selected, identically or differently, from H, F, CN, $Si(R^6)_3$, straight-chain alkyl groups having 1 to 20 C atoms, branched or cyclic alkyl groups having 3 to 20 C atoms, aromatic ring systems having 6 to 40 aromatic ring atoms, and heteroaromatic ring systems having 5 to 40 aromatic ring atoms; where two or more radicals $R^5$ may be connected to each other to form a ring; where the said alkyl groups and the said aromatic and heteroaromatic ring systems may in each case be substituted by one or more radicals $R^6$.

Preferred compounds according to formula (1) are shown in the following Table 1:

TABLE 1

(1)

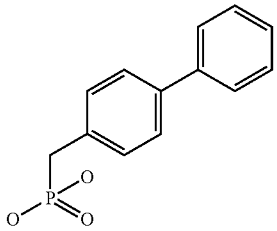 [SMILES: O=P(O)(O)Cc1ccc(-c2ccccc2)cc1]

TABLE 1-continued (2)

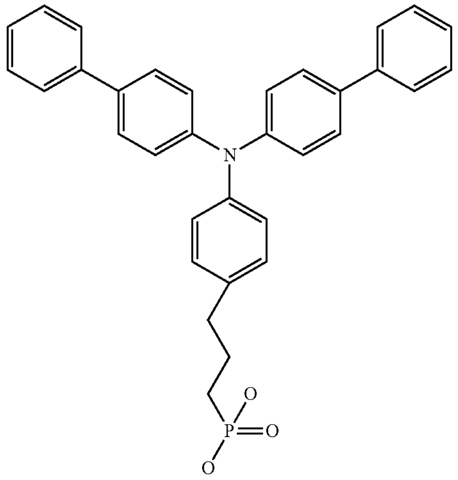 [SMILES: O=P(O)(O)CCCc1ccc(N(c2ccc(-c3ccccc3)cc2)c2ccc(-c3ccccc3)cc2)cc1]

(3)

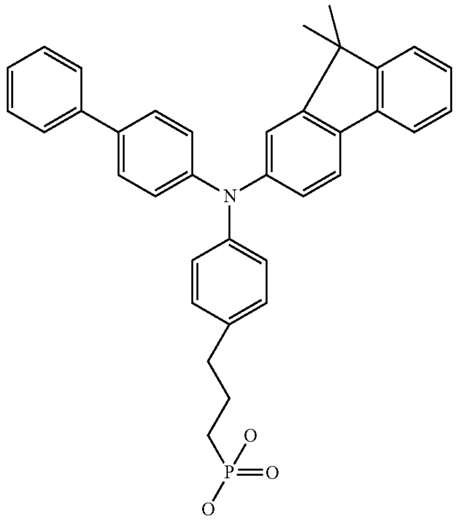 [SMILES: CC1(C)c2ccccc2-c2ccc(N(c3ccc(CCCP(=O)(O)O)cc3)c3ccc(-c4ccccc4)cc3)cc21]

(4)

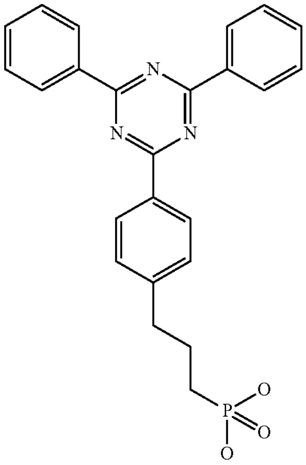 [SMILES: O=P(O)(O)CCCc1ccc(-c2nc(-c3ccccc3)nc(-c3ccccc3)n2)cc1]

TABLE 1-continued
(5)
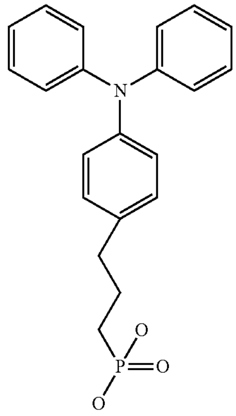 [SMILES: O=P(O)(O)CCCc1ccc(N(c2ccccc2)c2ccccc2)cc1]
(6)
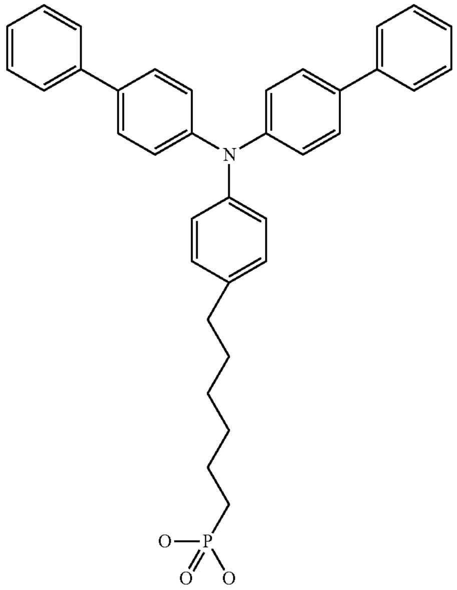 [SMILES: O=P(O)(O)CCCCCCc1ccc(N(c2ccc(-c3ccccc3)cc2)c2ccc(-c3ccccc3)cc2)cc1]
(7)
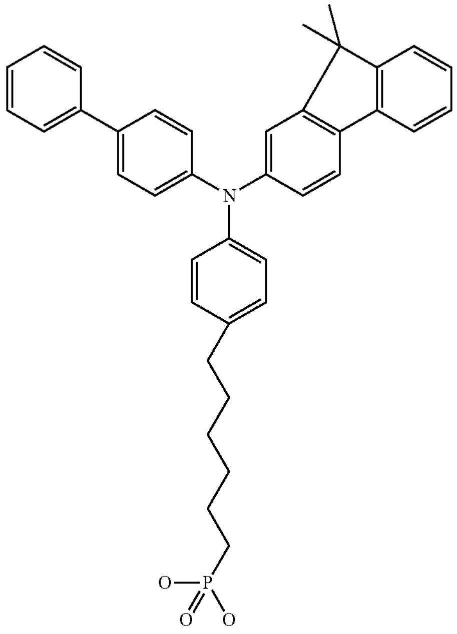 [SMILES: CC1(C)c2ccccc2-c2ccc(N(c3ccc(CCCCCCP(=O)(O)O)cc3)c3ccc(-c4ccccc4)cc3)cc21]
TABLE 1-continued
(8)
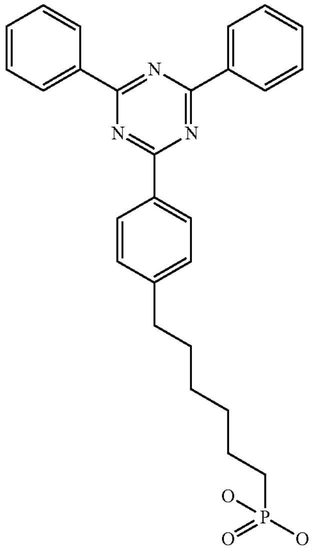 [SMILES: O=P(O)(O)CCCCCCc1ccc(-c2nc(-c3ccccc3)nc(-c3ccccc3)n2)cc1]
(9)
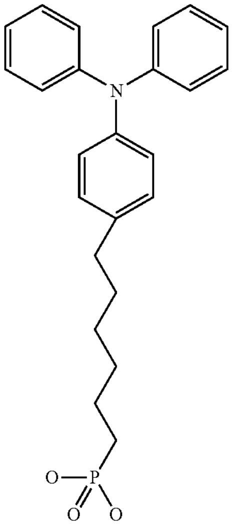 [SMILES: O=P(O)(O)CCCCCCc1ccc(N(c2ccccc2)c2ccccc2)cc1]
(10)
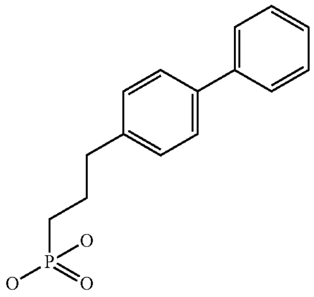 [SMILES: O=P(O)(O)CCCc1ccc(-c2ccccc2)cc1]

TABLE 1-continued
(11)
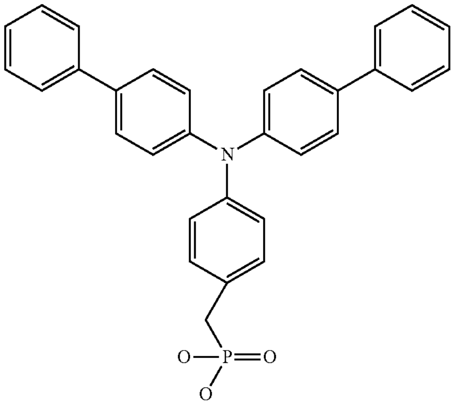 [SMILES: O=P(O)(O)Cc1ccc(N(c2ccc(-c3ccccc3)cc2)c2ccc(-c3ccccc3)cc2)cc1]
(12)
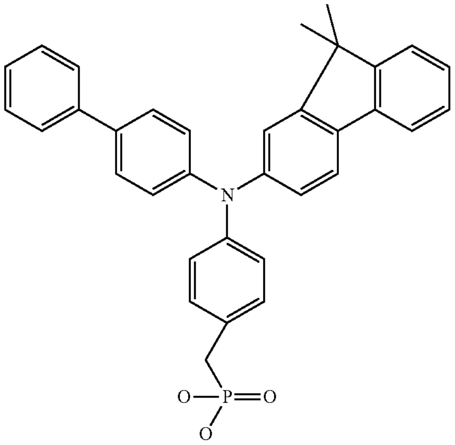 [SMILES: CC1(C)c2ccccc2-c2ccc(N(c3ccc(CP(=O)(O)O)cc3)c3ccc(-c4ccccc4)cc3)cc21]
(13)
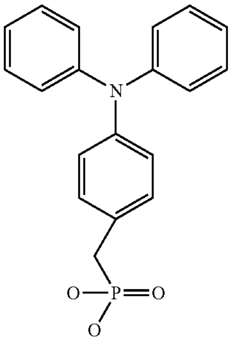 [SMILES: O=P(O)(O)Cc1ccc(N(c2ccccc2)c2ccccc2)cc1]
(14)
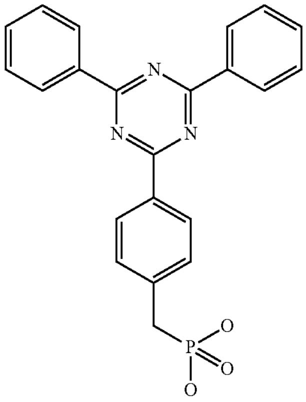 [SMILES: O=P(O)(O)Cc1ccc(-c2nc(-c3ccccc3)nc(-c3ccccc3)n2)cc1]
TABLE 1-continued
(15)
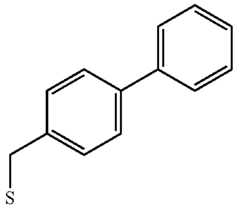 [SMILES: SCc1ccc(-c2ccccc2)cc1]
(16)
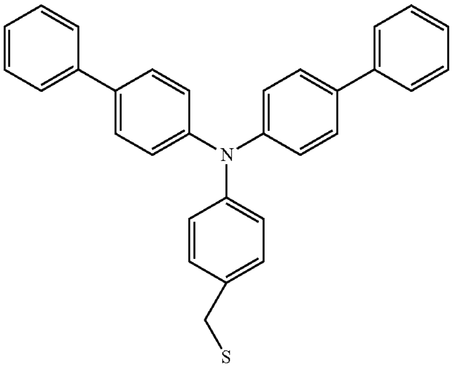 [SMILES: SCc1ccc(N(c2ccc(-c3ccccc3)cc2)c2ccc(-c3ccccc3)cc2)cc1]
(17)
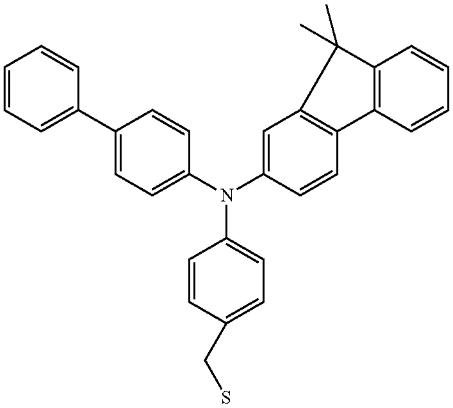 [SMILES: CC1(C)c2ccccc2-c2ccc(N(c3ccc(CS)cc3)c3ccc(-c4ccccc4)cc3)cc21]
(18)
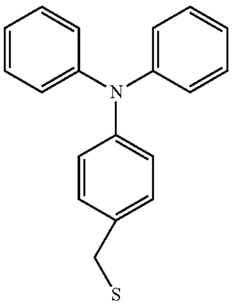 [SMILES: SCc1ccc(N(c2ccccc2)c2ccccc2)cc1]

TABLE 1-continued
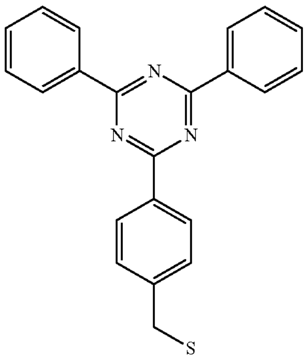 [SMILES: SCc1ccc(-c2nc(-c3ccccc3)nc(-c3ccccc3)n2)cc1]
(19)
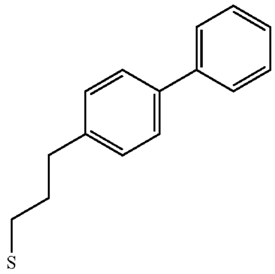 [SMILES: SCCCc1ccc(-c2ccccc2)cc1]
(20)
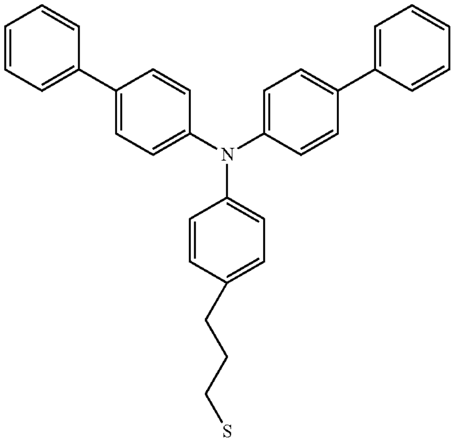 [SMILES: SCCCc1ccc(N(c2ccc(-c3ccccc3)cc2)c2ccc(-c3ccccc3)cc2)cc1]
(21)
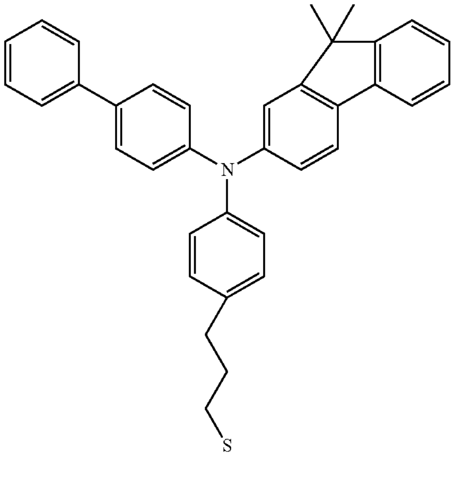 [SMILES: CC1(C)c2ccccc2-c2ccc(N(c3ccc(CCCS)cc3)c3ccc(-c4ccccc4)cc3)cc21]
(22)
TABLE 1-continued
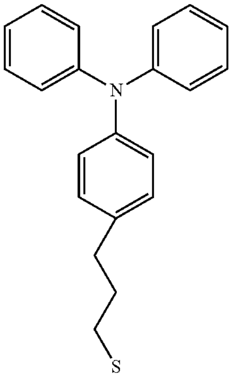 [SMILES: SCCCc1ccc(N(c2ccccc2)c2ccccc2)cc1]
(23)
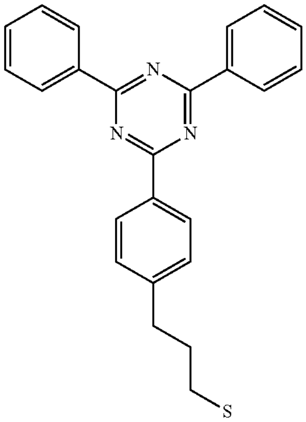 [SMILES: SCCCc1ccc(-c2nc(-c3ccccc3)nc(-c3ccccc3)n2)cc1]
(24)
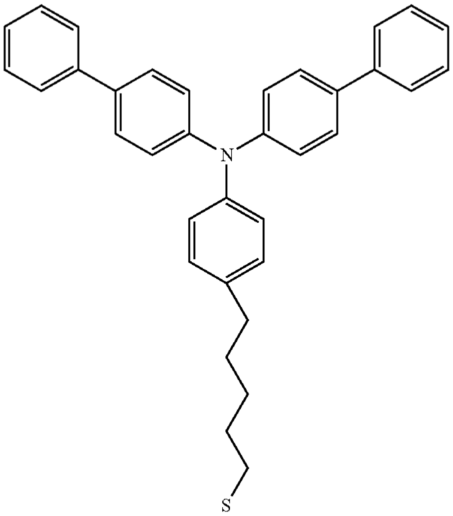 [SMILES: SCCCCCc1ccc(N(c2ccc(-c3ccccc3)cc2)c2ccc(-c3ccccc3)cc2)cc1]
(25)

TABLE 1-continued
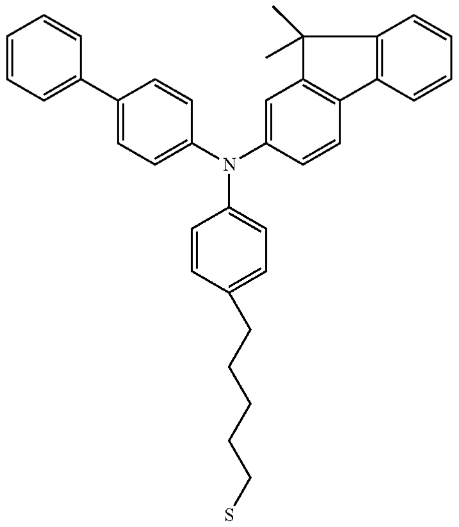 [SMILES: CC1(C)c2ccccc2-c2ccc(N(c3ccc(CCCCCS)cc3)c3ccc(-c4ccccc4)cc3)cc21]
(26)
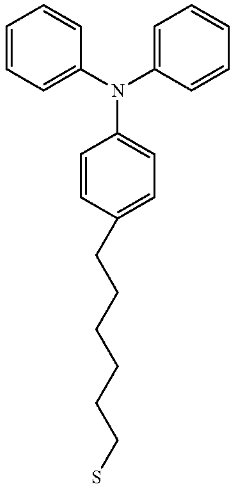 [SMILES: SCCCCCCc1ccc(N(c2ccccc2)c2ccccc2)cc1]
(27)
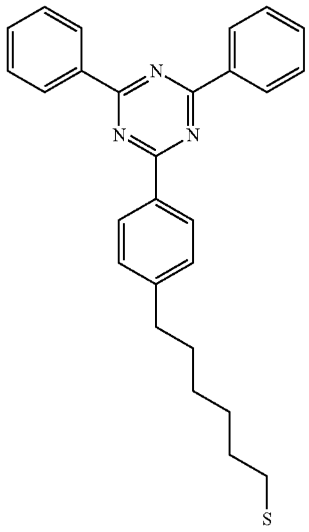 [SMILES: SCCCCCCc1ccc(-c2nc(-c3ccccc3)nc(-c3ccccc3)n2)cc1]
(28)
TABLE 1-continued
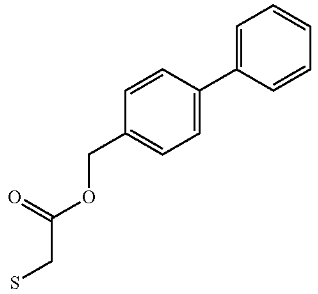 [SMILES: O=C(CS)OCc1ccc(-c2ccccc2)cc1]
(29)
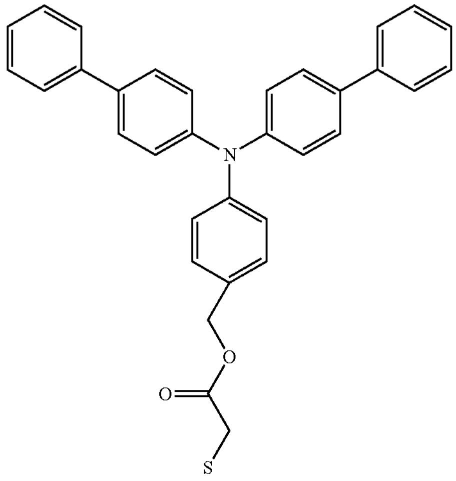 [SMILES: O=C(CS)OCc1ccc(N(c2ccc(-c3ccccc3)cc2)c2ccc(-c3ccccc3)cc2)cc1]
(30)
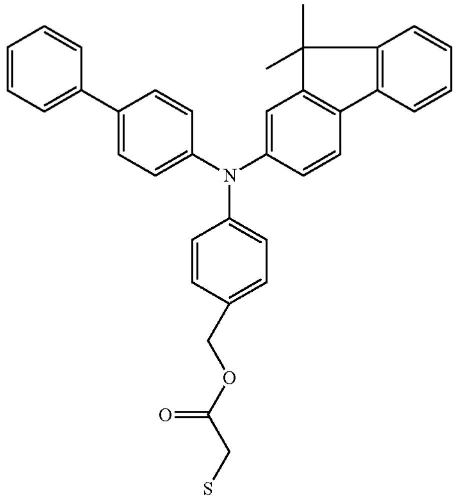 [SMILES: CC1(C)c2ccccc2-c2ccc(N(c3ccc(COC(=O)CS)cc3)c3ccc(-c4ccccc4)cc3)cc21]
(31)

TABLE 1-continued
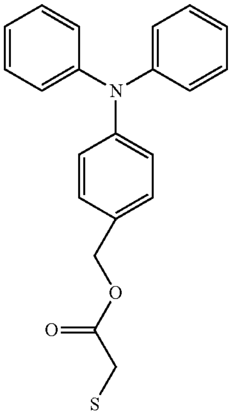 [SMILES: O=C(CS)OCc1ccc(N(c2ccccc2)c2ccccc2)cc1]
(32)
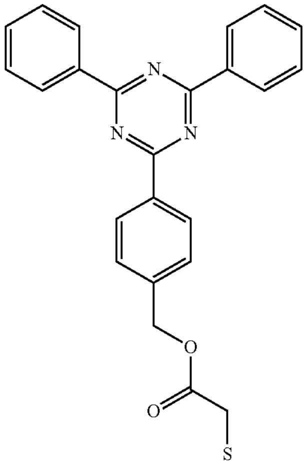 [SMILES: O=C(CS)OCc1ccc(-c2nc(-c3ccccc3)nc(-c3ccccc3)n2)cc1]
(33)
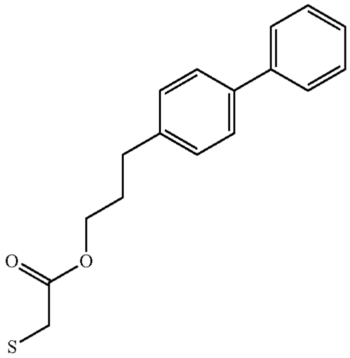 [SMILES: O=C(CS)OCCCc1ccc(-c2ccccc2)cc1]
(34)
TABLE 1-continued
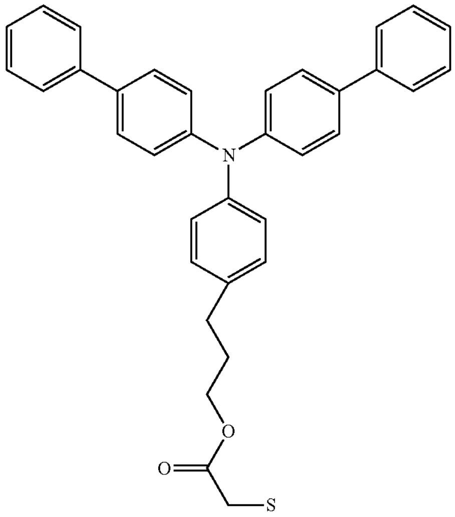 [SMILES: O=C(CS)OCCCc1ccc(N(c2ccc(-c3ccccc3)cc2)c2ccc(-c3ccccc3)cc2)cc1]
(35)
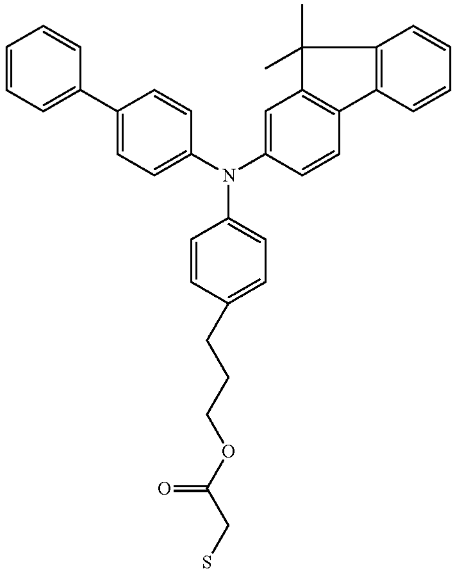 [SMILES: CC1(C)c2ccccc2-c2ccc(N(c3ccc(CCCOC(=O)CS)cc3)c3ccc(-c4ccccc4)cc3)cc21]
(36)
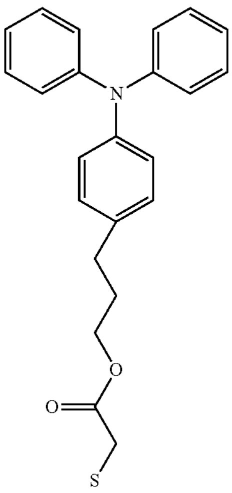 [SMILES: O=C(CS)OCCCc1ccc(N(c2ccccc2)c2ccccc2)cc1]
(37)

TABLE 1-continued
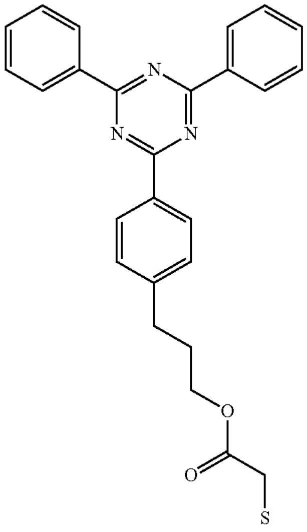 [SMILES: O=C(CS)OCCCc1ccc(-c2nc(-c3ccccc3)nc(-c3ccccc3)n2)cc1]
(38)
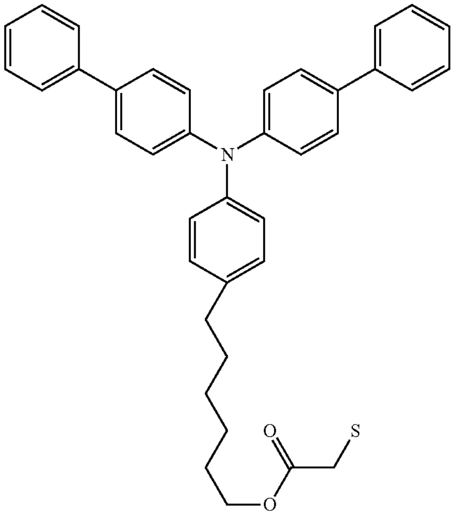 [SMILES: O=C(CS)OCCCCCCc1ccc(N(c2ccc(-c3ccccc3)cc2)c2ccc(-c3ccccc3)cc2)cc1]
(39)
TABLE 1-continued
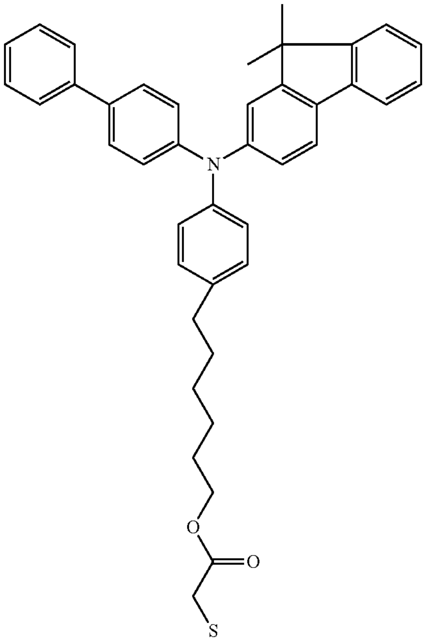 [SMILES: CC1(C)c2ccccc2-c2ccc(N(c3ccc(CCCCCCOC(=O)CS)cc3)c3ccc(-c4ccccc4)cc3)cc21]
(40)
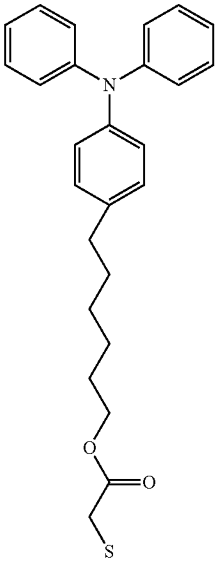 [SMILES: O=C(CS)OCCCCCCc1ccc(N(c2ccccc2)c2ccccc2)cc1]
(41)

TABLE 1-continued (42)

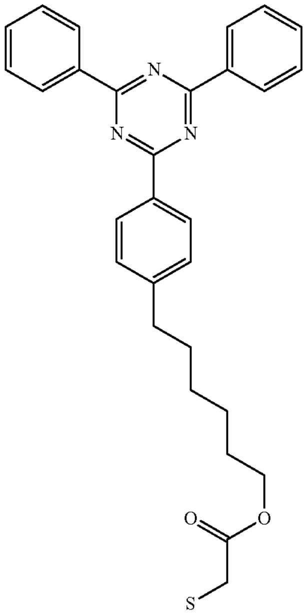 [SMILES: O=C(CS)OCCCCCCc1ccc(-c2nc(-c3ccccc3)nc(-c3ccccc3)n2)cc1]

The compound according to the invention as described above, which comprises in its structure an anchor group (i.e., group AG), a conjugated, conductive functional group (i.e., group FG) and a flexible, conjugation interrupting linker (i.e., group L) that decouples the anchor group from the functional group is suitable as ligand for binding to the surface of a semiconducting nanoparticle, thereby ensuring passivation of the nanoparticle surface and solubility of the nanoparticle in solution. Further, it allows for an improved surface binding process and increased ligand density on the surface and enables improved charge transport through the layer and into the quantum material, thereby improving the overall performance of an electronic device.

Semiconductor Nanoparticle

The present invention further relates to a semiconductor nanoparticle. According to the invention, the semiconductor nanoparticle comprises a core, one or more shell layers and at least one ligand that is attached to the outermost surface of the one or more shell layers, said at least on ligand being selected from the compounds according to the invention as described above.

Semiconducting/semiconductor nanoparticles or semi-conducting/semiconductor nanocrystals in the context of this application are understood to mean semiconducting light emitting nanoparticles.

According to the present invention, as an inorganic part of the semiconductor nanoparticle, a wide variety of publicly known semiconducting light emitting nanoparticles can be used as desired.

Further, as used herein the term "attached" should be understood to include covalent bonding or ionic bonding, or dipole-dipole interaction, without being limited thereto.

A type of shape of the semiconductor nanoparticle of the present invention is not particularly limited. Any type, for examples, spherical shaped, elongated shaped, star shaped, polyhedron shaped semiconductor nanoparticle, can be used.

According to the present invention, said one or more shell layers of the semiconductor nanoparticle is preferably a single shell layer, a double shell layer, or multishell layers having more than two shell layers, most preferably it is a double shell layer.

As used herein, the term "shell layer" means the structure covering fully or partially said core. Preferably, said one or more shell layers fully covers said core. The terms "core" and "shell" are well known in the art and typically used in the field of quantum materials, such as U.S. Pat. No. 8,221,651 B2.

As used herein, the term "nano" means the a particle with at least one dimension size, i.e. the diameter of the particle, is in between 0.1 nm and 999 nm, preferably, it is from 0.1 nm to 150 nm. The term nano-sized material refers to a corresponding material of that size.

The size of the nanoparticles can be measured by using the standard technique transmission electron microscope.

In a preferred embodiment of the present invention, the semiconducting light emitting nanoparticle of the present invention is a quantum sized material which is also called quantum material The quantum sized material or quantum material can be a quantum dot or a quantum rod, Preferably, the quantum-sized material or quantum material is a quantum dot.

As used herein, the term "quantum sized" means the size of the semiconductor material itself without ligands or another surface modification, which can show the quantum confinement effect, like described in, for example, ISBN: 978-3-662-44822-9. Generally, it is said that the quantum sized materials can emit tunable, sharp and vivid colored light due to "quantum confinement" effect.

Preferably, the diameter of the overall structure of the quantum sized material is from 1 nm to 100 nm, more preferably, it is from 1 nm to 30 nm, even more preferably, it is from 5 nm to 15 nm. Accordingly, the semiconductor nanoparticle of the present invention is preferably a so-called "quantum dot" (QD).

According to the present invention, said core of the semiconductor nanoparticle can vary. For example, CdS, CdSe, CdTe, ZnS, ZnSe, ZnSeS, ZnTe, ZnO, GaAs, GaP, GaSb, HgS, HgSe, HgSe, HgTe, InAs, InP, InPS, InPZnS, InPZn, InPGa, InSb, AlAs, AlP, AlSb, $Cu_2S$, $Cu_2Se$, $CuInS_2$, $CuInSe_2$, $Cu_2(ZnSn)S_4$, $Cu_2(InGa)S_4$, $TiO_2$ alloys and a combination of any of these can be used.

In a preferred embodiment of the present invention, said core of the semiconductor nanoparticle comprises one or more of group 13 elements of the periodic table and one or more of group 15 elements of the periodic table. For example, GaAs, GaP, GaSb, InAs, InP, InPS, InPZnS, InPZn, InPGa, InSb, AlAs, AlP, AlSb, $CuInS_2$, $CuInSe_2$, $Cu_2(InGa)S_4$, and a combination of any of these.

Even more preferably, the core comprises In and P atoms, for example, InP, InPS, InPZnS, InPZn or InPGa.

According to a further preferred embodiment of the present invention, said at least one of the shell layers comprises a $1^{st}$ element of group 12, 13 or 14 of the periodic table and a $2^{nd}$ element of group 15 or 16 of the periodic table. Preferably, all shall layers comprises a $1^{st}$ element of group 12, 13 or 14 of the periodic table and a $2^{nd}$ element of group 15 or 16 of the periodic table.

More preferably, at least one of the shell layers comprises a $1^{st}$ element of group 12 of the periodic table and a $2^{nd}$ element of group 16 of the periodic table. For example, CdS, CdZnS, ZnS, ZnSe, ZnSSe, ZnSSeTe, CdS/ZnS, ZnSe/ZnS or ZnS/ZnSe shell layers can be used. Even more preferably, all shall layers comprises a $1^{st}$ element of group 12 of the periodic table and a $2^{nd}$ element of group 16 of the periodic table.

Particularly preferably, at least one shell layer is represented by following formula (II), $$ZnS_xSe_yTe_z, \quad (II),$$

in which 0≤x≤1, 0≤y≤1, 0≤z≤1, and x+y+z=1, with 0≤x≤1, 0≤y≤1, z=0, and x+y=1 being even more preferred.

ZnS, ZnSe, ZnSeS, ZnSeSTe, CdS/ZnS, ZnSe/ZnS, ZnS/ZnSe shell layers are most preferably used.

It is further preferred that all shell layers are represented by formula (II).

For example, as a semiconducting light emitting nanoparticle for green and/or red emission use, CdSe/CdS, CdSeS/CdZnS, CdSeS/CdS/ZnS, ZnSe/CdS, CdSe/ZnS, InP/ZnS, InP/ZnSe, InP/ZnSe/ZnS, InP/ZnS/ZnSe, InPZn/ZnS, InPZn/ZnSe/ZnS, InPZn/ZnS/ZnSe, ZnSe/CdS, ZnSe/ZnS semiconducting light emitting nanoparticle or combination of any of these, can be used.

More preferably, InP/ZnS, InP/ZnSe, InP/ZnSe/ZnS, InP/ZnS/ZnSe, InPZn/ZnS, InPZn/ZnSe/ZnS, InPZn/ZnS/ZnSe can be used.

In a preferred embodiment of the present invention, said shell layers of the semiconductor nanoparticle are double shell layers.

Said semiconducting light emitting nanoparticles are publically available, for example, from Sigma-Aldrich and/or described in, for example, *ACS Nano,* 2016, 10 (6), pp 5769-5781, Chem. Moter. 2015, 27, 4893-4898, and the international patent application No. WO 2010/095140 A2.

It is preferred according to the present invention that the semiconductor nanoparticle comprises at least two different ligands attached to its outermost surface, preferably exactly two different ligands, wherein the ligands are selected from the compounds according to the invention as described above.

Further preferably, the semiconductor nanoparticle comprises a first ligand and a second ligand, both selected from the compounds according to the invention as described above, and wherein the first ligand comprises an organic functional group selected from an electron transporting group (i.e. the electron-transporting property is superior to the hole-transport property) and wherein the second ligand comprises an organic functional group selected from a hole transporting group (i.e. the hole-transporting property is superior to the electron-transport property). Here, as both the highest excited state of the electron-transporting ligand as well as the hole-transporting type ligand are equal or higher in energy than the excited state of the quantum dot (most preferably higher in energy by 0.15 eV), the combination of the first ligand and the second ligand is capable of forming an excited state complex (so-called exciplex) as an supramolecular excited state with lower energy than the sum of the isolated charged groups. This energy of this exciplex (host) can be transferred to the semiconductor nanoparticle (guest) by means of energy transfer (e.g. Førster resonance energy transfer (FRET)), thereby fulfilling the boundary condition that the emission spectrum of the host material (i.e. the exciplex of the first and second ligand) overlaps with the absorption band of the accepting quantum-dot (most preferably the longest-wavelength-side absorption band in the absorption spectrum is 5000 $M^{-1}$ $cm^{-1}$). Through energy transfer to the core via an exciplex the efficiency (e.g. quantum efficiency) can be further improved.

One or even both electron- and/or hole-transporting type moieties can be present on additional molecules in the emissive layer which are not the quantum-dot, i.e. of co-host type, the exciplex may form between hole-transporting co-host and electron-transporting ligand of the quantum dot or vice versa, or even the exciplex may be formed solely from both sorts of transporting units provided by two or more co-hosts. In all these cases the energy can be as well transferred to the quantum-dot fulfilling the conditions mentioned above. FRET from the exciplex to the core of the quantum-dot results in improved performance characteristics (particularly efficiency such as EQE) of the electroluminescent devices.

Additional Ligands

The semiconductor nanoparticle according to the present invention may optionally comprises one or more different types of ligands (i.e., not selected from the compounds according to the invention) attached to the outermost surface of the shell layers, in addition to the at least one ligand selected from the compounds of the present invention as described herein.

Accordingly, the outermost surface of the shell layers of the semiconducting light emitting nanoparticle may be overcoated with different types of surface ligands together with/in addition to the at least one ligand selected from the compounds of the invention as described above, if desired.

Without wishing to be bound by theory, it is believed that such surface ligands can effect that the semiconducting light emitting nanoparticles is dispersed in a solvent more easily.

According to a preferred embodiment of the present invention, the total amount of the ligand or ligands selected from the compounds of the present invention attached to the outermost surface of the one or more shell layers as defined above is in the range from 1 wt % to 99.9 wt %, preferably 30 wt % to 99.9 wt %, preferably in the range from 50 wt % to 99.9 wt %, and most preferably in the range from 70 wt % to 99.9 wt % of the total ligands attached onto the outermost surface of the shell layer(s). The final composition of the ligands content attached the outermost surface of the one or more shell layers is determined through Thermogravimetric Analysis (TGA—Mettler Toledo TGA/DSC 3+).

The surface ligands in common use include phosphines and phosphine oxides such as Trioctylphosphine oxide (TOPO), Trioctylphosphine (TOP), and Tributylphosphine (TBP); phosphonic acids such as Dodecylphosphonic acid (DDPA), Tridecylphosphonic acid (TDPA), Octadecylphosphonic acid (ODPA), and Hexylphosphonic acid (HPA); amines such as Oleylamine, Dedecyl amine (DDA), Tetradecyl amine (TDA), Hexadecyl amine (HDA), and Octadecyl amine (ODA), Oleylamine (OLA), thiols such as hexadecane thiol, dodecanethiol and hexane thiol; carboxylic acids such as oleic acid, stearic acid, myristic acid, palmitic acid; acetic acid and a combination of any of these.

Examples of surface ligands have been described in, for example, the international patent application No. WO 2012/059931A.

The semiconductor nanocrystal according to the invention comprising at least one ligand selected from the compounds of the invention as described above bonded to the surface has a high fluorescent quantum yield, can realize a high contrast, can improve charge transport into the semiconductor nanocrystal and within the semiconductor nanocrystal layer, and by doing so improves the efficiency of an electronic device, in particular an electroluminescent device.

Composition

Especially when being used in electronic devices, the semiconductor nanoparticle according to the present invention may be combined with further semiconductor nanoparticles or further organic functional materials, which are commonly used in electronic devices according to the prior art, to form a composition. A great variety of suitable organic functional materials is known to those skilled in the art in the field of electronic devices.

The present invention thus further provides for a composition comprising at least one first semiconductor nanoparticle according to the invention as described above and at least one further organic functional material selected from electron injecting materials, electron transporting materials, hole blocking materials, n-dopants, host materials, matrix materials, wide band gap materials, fluorescent emitter materials, delayed fluorescent materials, phosphorescent emitter materials, electron blocking materials, hole transporting materials, hole injecting materials and p-dopants.

Preferably, the composition comprises at least one first semiconductor nanoparticle according to the invention and at least two different organic functional materials, preferably exactly two different organic functional materials, as defined above, which functional materials are more preferably selected from matrix materials, electron transporting materials and hole transporting materials.

Delayed fluorescent materials, such as delayed fluorescent emitters or delayed fluorescent hosts, are well known in the art and disclosed in, e.g., Ye Tao et al., Adv. Mater. 2014, 26, 7931-7958, M. Y. Wong et al., Adv. Mater. 2017, 29, 1605444, WO 2011/070963, WO 2012/133188, WO 2015/022974 and WO 2015/098975. Typically, the delayed fluorescent materials are characterized in that they exhibit a rather small energy gap between their singlet energy ($S_1$) and triplet energy ($T_1$). Preferably $\Delta E_{ST}$ is smaller than 0.5 eV, very preferably smaller than 0.3 eV and particularly preferably smaller than 0.2 eV, wherein $\Delta E_{ST}$ represents the energy difference between the singlet energy ($S_1$) and the triplet energy ($T_1$).

Within the present invention, wide band gap materials are understood to mean a material as disclosed in U.S. Pat. No. 7,294,849, which is characterized in having a band gap of at least 3.5 eV, wherein the term "band gap" means the energy gap between the highest occupied molecular orbital (HOMO) and the lowest unoccupied molecular orbital (LUMO). Such systems are well known in the art and exhibit particularly advantageous performance characteristics in electroluminescent devices.

The term "phosphorescent emitting compounds" typically encompasses compounds where the emission of light is effected through a spin-forbidden transition, for example a transition from an excited triplet state or a state having a higher spin quantum number, for example a quintet state.

Preferably the term phosphorescent emitting compound refers to a compound that emits radiation from a triplet state.

Suitable phosphorescent emitting compounds are especially the ones that have already been described above.

Preferred fluorescent emitting compounds are selected from the class of the arylamines. An arylamine or an aromatic amine in the context of this invention is understood to mean a compound containing three substituted or unsubstituted aromatic or heteroaromatic ring systems bonded directly to the nitrogen. Preferably, at least one of these aromatic or heteroaromatic ring systems is a fused ring system, more preferably having at least 14 aromatic ring atoms. Preferred examples of these are aromatic anthracenamines, aromatic anthracenediamines, aromatic pyrenamines, aromatic pyrenediamines, aromatic chrysenamines or aromatic chrysenediamines. An aromatic anthracenamine is understood to mean a compound in which a diarylamino group is bonded directly to an anthracene group, preferably in the 9 position. An aromatic anthracenediamine is understood to mean a compound in which two diarylamino groups are bonded directly to an anthracene group, preferably in the 9, 10 positions. Aromatic pyrenamines, pyrenediamines, chrysenamines and chrysenediamines are defined analogously, where the diarylamino groups are bonded to the pyrene preferably in the 1 position or 1,6 positions. Further preferred emitting compounds are indenofluorenamines or -fluorenediamines, for example according to WO 2006/108497 or WO 2006/122630, benzoindenofluorenamines or -fluorenediamines, for example according to WO 2008/006449, and dibenzoindenofluoreneamines or -diamines, for example according to WO 2007/140847, and the indenofluorene derivatives having fused aryl groups disclosed in WO 2010/012328. Likewise preferred are the pyrenearylamines disclosed in WO 2012/048780 and in WO 2013/185871. Likewise preferred are the benzoindenofluorenamines disclosed in WO 2014/037077, the benzofluorenamines disclosed in WO 2014/106522, the extended benzoindenofluorenes disclosed in WO 2014/111269 and in WO 2017/036574, the phenoxazines disclosed in WO 2017/028940 and in WO 2017/028941, and the fluorene derivatives bonded to furan units or to thiophene units that are disclosed in WO 2016/150544, or other materials as used according to the prior art.

Useful host or matrix materials, which are preferably used in combination with fluorescent emitting materials, include materials of various substance classes. Preferred matrix materials are selected from the classes of the oligoarylenes (e.g. 2,2',7,7'-tetraphenylspirobifluorene according to EP 676461 or dinaphthylanthracene), especially of the oligoarylenes containing fused aromatic groups, the oligoarylenevinylenes (e.g. DPVBi or spiro-DPVBi according to EP 676461), the polypodal metal complexes (for example according to WO 2004/081017), the hole-conducting compounds (for example according to WO 2004/058911), the electron-conducting compounds, especially ketones, phosphine oxides, sulphoxides, etc. (for example according to WO 2005/084081 and WO 2005/084082), the atropisomers (for example according to WO 2006/048268), the boronic acid derivatives (for example according to WO 2006/117052) or the benzanthracenes (for example according to WO 2008/145239). Particularly preferred matrix materials are selected from the classes of the oligoarylenes comprising naphthalene, anthracene, benzanthracene and/or pyrene or atropisomers of these compounds, the oligoarylenevinylenes, the ketones, the phosphine oxides and the sulphoxides. Very particularly preferred matrix materials are selected from the classes of the oligoarylenes comprising anthracene, benzanthracene, benzophenanthrene and/or pyrene or atropisomers of these compounds. An oligoarylene in the context of this invention shall be understood to mean a compound in which at least three aryl or arylene groups are bonded to one another. Preference is further given to the anthracene derivatives disclosed in WO 2006/097208, WO 2006/131192, WO 2007/065550, WO 2007/110129, WO 2007/065678, WO 2008/145239, WO 2009/100925, WO 2011/054442 and EP 1553154, the pyrene compounds disclosed in EP 1749809, EP 1905754 and US 2012/0187826, the benzanthracenylanthracene compounds disclosed in WO 2015/158409, the indenobenzofurans disclosed in WO 2017/025165, and the phenanthrylanthracenes disclosed in WO 2017/036573, or other materials as used according to the prior art.

Preferred host or matrix materials used in combination with phosphorescent emitting materials are aromatic ketones, aromatic phosphine oxides or aromatic sulphoxides or sulphones, for example according to WO 2004/013080, WO 2004/093207, WO 2006/005627 or WO 2010/006680, triarylamines, carbazole derivatives, e.g. CBP (N,N-biscarbazolylbiphenyl) or the carbazole derivatives disclosed in WO 2005/039246, US 2005/0069729, JP 2004/288381, EP 1205527 or WO 2008/086851, indolocarbazole derivatives, for example according to WO 2007/063754 or WO 2008/056746, indenocarbazole derivatives, for example according to WO 2010/136109, WO 2011/000455 or WO 2013/041176, azacarbazole derivatives, for example according to EP 1617710, EP 1617711, EP 1731584, JP 2005/347160, bipolar matrix materials, for example according to WO 2007/137725, silanes, for example according to WO 2005/111172, azaboroles or boronic esters, for example according to WO 2006/117052, triazine derivatives, for example according to WO 2010/015306, WO 2007/063754 or WO 2008/056746, zinc complexes, for example according to EP 652273 or WO 2009/062578, diazasilole or tetraazasilole derivatives, for example according to WO 2010/054729, diazaphosphole derivatives, for example according to WO 2010/054730, bridged carbazole derivatives, for example according to US 2009/0136779, WO 2010/050778, WO 2011/042107, WO 2011/088877 or WO 2012/143080, triphenylene derivatives, for example according to WO 2012/048781, or lactams, for example according to WO 2011/116865 or WO 2011/137951, or other materials as used according to the prior art.

It is further preferred that the composition comprising the at least first semiconductor nanoparticle further comprises a plurality of host or matrix materials (so-called "mixed matrix systems"), preferably two or three different host or matrix materials, more preferably two different host or matrix materials. More preferably, in this case, one of the two different materials is a host or matrix material having hole-transporting properties, that is, a material that significantly contributes to the hole transport, and the other one is a host or matrix material having electron-transporting properties, that is, a material that significantly contributes to the electron transport. One source of more detailed information about mixed matrix systems is the application WO 2010/108579.

Further preferably, according to the present invention a wide variety of publically known transparent matrix materials suitable for electronic devices may be used.

According to the present invention, the term "transparent" means at least around 60% of incident light transmit at the thickness used in an optical medium, such as an optical film, a color filter, a color conversion film, a remote phosphor tape, or the like, of an electronic device and at a wavelength or a range of wavelength used during operation of said optical medium. Preferably, it is over 70%, more preferably over 75%, and most preferably over 80%.

Preferably, the transparent matrix material is a transparent polymer. For example, the transparent polymer for the transparent matrix material is selected from poly(meth) acrylates, epoxys, polyurethanes and polysiloxanes.

Us used herein, the term "polymer" means a material having a repeating unit and a weight average molecular weight (Mw) of 1000 or more. Preferably, the weight average molecular weight (Mw) of the polymer used as the transparent matrix material is in the range from 1000 to 300000, more preferably from 10000 to 250000.

Further preferably, the glass transition temperature (Tg) of the transparent polymer is 70° C. or more and 250° C. or less. Tg can be measured based on changes in the heat capacity observed in Differental scanning colorimetry like described in http://pslc.ws/macrog/dsc.htm.

Suitable electron transport materials (or hole blocking materials, or hole injecting materials) can be any materials used in the prior art as electron transport materials, preferably in an electron transport layer (or hole blocker layer or electron injection layer) of an electronic device. Especially preferred are aluminium complexes, for example $Alq_3$, zirconium complexes, for example $Zrq_4$, lithium complexes, for example Liq, benzimidazole derivatives, triazine derivatives, pyrimidine derivatives, pyridine derivatives, pyrazine derivatives, quinoxaline derivatives, quinoline derivatives, oxadiazole derivatives, aromatic ketones, lactams, boranes, diazaphosphole derivatives and phosphine oxide derivatives. Further suitable materials are derivatives of the above-mentioned compounds as disclosed in JP 2000/053957, WO 2003/060956, WO 2004/028217, WO 2004/080975 and WO 2010/072300.

Suitable hole transport materials (or electron blocking materials, or hole injecting materials) can be any materials used in the prior art as hole transport materials, preferably in a hole transport layer (or electron blocker layer or hole injection layer) of an electronic device. Preferred examples of hole transport materials are indenofluoreneamines and derivatives (for example in accordance with WO 06/122630 or WO 06/100896), the amine derivatives as disclosed in EP 1661888, hexaazatriphenylene derivatives (for example in accordance with WO 01/049806), amine derivatives with condensed aromatics (for example in accordance with U.S. Pat. No. 5,061,569), the amine derivatives as disclosed in WO 95/09147, monobenzoindeno-fluoreneamines (for example in accordance with WO 08/006449) or dibenzoindenofluoreneamines (for example in accordance with WO 07/140847). Suitable hole-transport and hole-injection materials are furthermore derivatives of the compounds depicted above, as disclosed in JP 2001/226331, EP 676461, EP 650955, WO 01/049806, U.S. Pat. No. 4,780,536, WO 98/30071, EP 891121, EP 1661888, JP 2006/253445, EP 650955, WO 06/073054 and U.S. Pat. No. 5,061,569 n-Dopants used according to the present invention are preferably those organic electron donor compounds capable of reducing one or more of the other compounds in the mixture. Preferred examples of n-dopants are $W(hpp)_4$ and further electron-rich metal complexes according to WO 2005/086251 A2, P=N-compounds (e.g. WO 2012/175535 A1, WO 2012/175219 A1), naphthylencarbodiimides (e.g. WO 2012/168358 A1), fluorenes (e.g. WO 2012/031735 A1), radicals and biradicals (e.g. EP 1837926 A1, WO 2007/107306 A1), pyridines (e.g. EP 2452946 A1, EP 2463927 A1), N-heterocyclic compounds (e.g. WO 2009/000237 A1) and acridines and phenazines (e.g. US 2007/145355 A1), or other materials as used according to the prior art.

p-Dopants used according to the present invention are preferably those organic electron acceptor compounds capable of oxidizing one or more of the other compounds in the mixture. Preferred examples of p-dopants are $F_4$-TCNQ, $F_6$-TNAP, NDP-2 (company Novaled), NDP-9 (company Novaled), quinones (e.g. EP 1538684 A1, WO 2006/081780 A1, WO 2009/003455 A1, WO 2010/097433 A1), radialenes (e.g. EP 1988587 A1, US 2010/102709 A1, EP 2180029 A1, WO 2011/131185 A1, WO 2011134458 A1, US 2012/223296 A1), S-containing transition metal complexes (e.g. WO 2007/134873 A1, WO 2008/061517 A2, WO 2008/061518 A2, DE 102008051737 A1, WO 2009/089821 A1, US 2010/096600 A1), bisimidazoles (e.g. WO 2008/138580 A1), phthalocyanines (e.g. WO 2008/058525 A2), boratetraazapentalenes (e.g. WO 2007/115540 A1) fullerenes (e.g. DE 102010046040 A1) and main group halogenides (e.g. WO 2008/128519 A2), or other materials as used according to the prior art.

According to another preferred embodiment of the invention, the composition may comprise the at least one first semiconductor nanoparticle of the invention as described above and at least one second semiconductor nanoparticle.

The at least one second semiconductor nanoparticle may be added to the at least one first semiconductor nanoparticle exclusively or in addition to the at least one further organic functional material as defined above to thereby form a composition.

Thus, according to a further preferred embodiment of the invention, the composition may comprise the at least one first semiconductor nanoparticle of the invention as described above, at least one second semiconductor nanoparticle and at least one further organic functional material as defined above.

Preferably, the at least one second semiconductor nanoparticle is selected from the semiconductor nanoparticles according to the invention as described above. Further preferably, the at least one second semiconductor nanoparticle and the first semiconductor nanoparticle differ from each other. That is, for example, the first and second semiconductor nanoparticles each may have different ligands attached to their outermost surface, which are selected from the compounds according to the invention as described above.

In the case that the composition comprises—exclusively or in addition to the at least one further organic functional material as defined above—at least one second semiconductor nanoparticle which differs from the at least one first semiconductor nanoparticle, it is preferred according to one embodiment of the composition that the at least one first semiconductor nanoparticle comprises at least one ligand attached to its outermost surface which comprises a delayed fluorescent group, and wherein the at least one second semiconductor nanoparticle comprises at least one ligand attached to its outermost surface which comprises a hole transporting group or an electron transporting group. Here, charge carriers can recombine to form an excited state in the delayed fluorescent group, and the excited state energy can then be transferred to the semiconductor nanoparticle (commonly referred to as "hyperfluorecence") by means of energy transfer (e.g. Førster resonance energy transfer).

According to another preferred embodiment of the composition comprising first and second semiconductor nanoparticles, which differ from each other as described above, the at least one first semiconductor nanoparticle comprises at least one ligand attached to its outermost surface which comprises a phosphorescent group, and wherein the at least one second semiconductor nanoparticle comprises at least one ligand attached to its outermost surface which comprises a hole transporting group or an electron transporting group. Here, charge carriers can recombine to form an excited state in the phosphorescent group, and the excited state energy can then be transferred to the semiconductor nanoparticle (commonly referred to as "hyperphosphorescence") by means of energy transfer (e.g. Førster energy transfer).

Both, hyperfluorecence and hyperphosphorescence as described above may lead to an increase in quantum efficiency.

According to a further preferred embodiment of the composition comprising first and second semiconductor nanoparticles, which differ from each other as described above, the at least one first semiconductor nanoparticle comprises at least one ligand attached to its outermost surface which comprises an electron transporting group, and wherein the at least one second semiconductor nanoparticle comprises at least one ligand attached to its outermost surface which comprises a hole transporting group, which makes possible exciplex formation as described above.

In each embodiment of the composition disclosed above, the ligands attached to the surface of the first and second semiconductor nanoparticles, respectively, are selected from the compounds according to the present invention. Accordingly, preferred hole transporting groups and electron transporting groups comprised in the ligands as described above are selected from hole transporting groups HT and electron transporting groups ET as defined herein with respect to the present invention. Likewise, preferred phosphorescent groups and delayed fluorescent groups mentioned above are selected from the phosphorescent groups and the delayed fluorescent group defined above.

Formulation

For the processing of the compounds, semiconductor particles or compositions of the invention from a liquid phase, for example by spin-coating or by printing methods, formulations comprising the compounds, semiconductor particles or compositions of the invention are required. These formulations may, for example, be solutions, dispersions or emulsions. For this purpose, it may be preferable to use mixtures of two or more solvents. Suitable and preferred solvents are, for example, toluene, anisole, o-, m- or p-xylene, methyl benzoate, mesitylene, tetralin, veratrole, THF, methyl-THF, THP, chlorobenzene, dioxane, phenoxytoluene, especially 3-phenoxytoluene, (−)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, methyl benzoate, NMP, p-cymene, phenetole, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane or mixtures of these solvents.

The invention therefore further provides for a formulation, in particular a solution, dispersion or emulsion, comprising a compound selected from the compounds of the present invention as described above, or a semiconductor nanoparticle according to the invention as described above, or a composition according to the invention as described above, and at least one solvent, preferably an organic solvent. The way in which such solutions can be prepared is known to those skilled in the art and is described, for example, in WO 2002/072714, WO 2003/019694 and the literature cited therein.

Process

The problem addressed by the present invention is also solved by a process for the preparation of a semiconductor nanoparticle according to the invention, wherein the process comprises providing a compound according to the invention, which serves as the ligand, and a semiconductor nanoparticle comprising a core and one or more shell layers into a solvent to get a mixture.

Preferably, said process is carried out under an inert condition, such as N2 or argon atmosphere. Further preferably, in said process the compound serving as ligand and the semiconductor nanoparticle are stirred for 1 sec or more, more preferably, 30 sec or more. Even more preferably, the stirring time in said process is in the range from 1 min to 100 hours, preferably 10 min to 1 hour.

Further preferably, the process is carried out at a temperature in the range from 0° C. to 100° C., more preferably at room temperature.

As the solvent, for example, toluene, hexane, chloroform, ethyl acetate, benzene, xylene, ethers, tetrahydrofuran, dichloromethane and heptane and a mixture of thereof, may be used, without being limited thereto.

The thus obtained semiconductor nanoparticles may be purified by subsequent precipitating and/or resuspending steps.

The synthesis steps and conditions for preparing and purifying the semiconductor nanoparticles according to the invention are familiar to the person skilled in the art and are described in the literature (for example in R. Gomes et al., *J. Phys. Chem. Lett.* 2011, 2, 145-152; J. S. Owen *J. Chem. Soc.* 2008, 130, 12279-12281).

The present invention also relates to a semiconductor nanoparticle obtainable or obtained from the process.

Electronic Device

The semiconductor nanoparticles and the compositions of the invention are suitable for use in electronic devices, especially in organic electroluminescent devices such as OLEDs, in particular in the emissive layer.

The present invention therefore further provides for an electronic device comprising at least one semiconductor nanoparticle according to the invention as described above, or a composition according to the invention as described above.

The electronic device is preferably selected from the group consisting of organic integrated circuits (OICs), organic field-effect transistors (OFETs), organic thin-film transistors (OTFTs), organic solar cells (OSCs), organic optical detectors, organic photoreceptors and, more preferably, organic electroluminescent devices (EL devices). Preferred EL devices are organic light-emitting transistors (OLETs), organic field-quench devices (OFQDs), organic light-emitting electrochemical cells (OLECs, LECs, LEECs), organic laser diodes (O-lasers) and organic light emitting diodes (OLEDs), of which OLEDs are most preferred.

Further preferably, the electronic device is an organic electroluminescent device that comprises the semiconductor nanoparticle or the composition of the invention in the emissive layer.

Particularly preferably, the electronic device is an organic electroluminescent device comprising anode, cathode and at least one organic layer, characterized in that the at least one organic layer, which is particularly preferably the emissive layer, comprises at least one semiconductor nanoparticle or a composition according to the invention as described above.

Within the present invention, the term “organic layer” is understood to mean any layer of an electronic device which comprises one or more organic compounds as functional materials.

Apart from the cathode, anode and emitting layer, the organic electroluminescent device may also comprise further layers. These are selected, for example, from in each case one or more hole injection layers, hole transport layers, hole blocking layers, electron transport layers, electron injection layers, electron blocking layers, exciton blocking layers, interlayers, charge generation layers (IDMC 2003, Taiwan; Session 21 OLED (5), T. Matsumoto, T. Nakada, J. Endo, K. Mori, N. Kawamura, A. Yokoi, J. Kido, *Multiphoton Organic EL Device Having Charge Generation Layer*) and/or organic or inorganic p/n junctions.

The sequence of the layers of an organic electroluminescent device within the context of the present invention is preferably as follows: anode-hole injection layer-hole transport layer-optionally further hole transport layer(s)-optionally electron blocking layer-emitting layer-optionally hole blocking layer-electron transport layer-electron injection layer-cathode. It is additionally possible for further layers to be present in the organic electroluminescent device.

A hole transport layer according to the present application is a layer having a hole-transporting function between the anode and emitting layer. An electron transport layer according to the present application is a layer having an electron-transporting function between the cathode and emitting layer Hole injection layers and electron blocking layers are understood in the context of the present application to be specific embodiments of hole transport layers. A hole injection layer, in the case of a plurality of hole transport layers between the anode and emitting layer, is a hole transport layer which directly adjoins the anode or is separated therefrom only by a single coating of the anode. An electron blocking layer, in the case of a plurality of hole transport layers between the anode and emitting layer, is that hole transport layer which directly adjoins the emitting layer on the anode side. The same applies accordingly to electron injection layers and hole blocking layers, which are understood in the context of the present application to be specific embodiments of electron transport layers. Suitable hole transport materials (or electron blocking materials, or hole injecting materials) to be used in a hole transport layer, a hole injection layer or an electron blocking layer may be selected from those organic functional materials as described above with respect to the composition of the invention. Suitable electron transport materials (or hole blocking materials, or electron injecting materials) to be used in an electron transport layer, an electron injection layer or a hole blocking layer may be selected from those organic functional materials as described above with respect to the composition of the invention.

The organic light emitting diode of the invention may contain two or more emitting layers. More preferably, these emitting layers in this case have several emission maxima between 380 nm and 750 nm overall, such that the overall result is white emission; in other words, various emitting compounds which may fluoresce or phosphoresce and which emit blue, green, yellow, orange or red light may be used in the emitting layers, alone or in combination, or in combination with the semiconducting light emitting nanoparticles of the invention. Especially preferred are three-layer systems, i.e. systems having three emitting layers, where the three layers show blue, green and orange or red emission (for the basic construction see, for example, WO 2005/011013). The semiconducting light emitting nanoparticles according to the invention may be present in one or more (if present) emissive layers. Preferably, the semiconductor nanoparticle or the composition according to the invention is present in at least one emissive layer, more preferably in all emissive layers that are present.

Suitable phosphorescent emitting compounds or fluorescent emitting compounds which may be used in an emitting layer in combination with the semiconducting light emitting nanoparticle of the invention may be selected from those organic functional materials as described above with respect to the composition of the invention. Likewise, the matrix or host materials suitable to be used in an emitting layer may be selected from those organic functional materials as described above with respect to the composition of the invention.

An emitting layer of an organic electroluminescent device may also comprise systems comprising a plurality of matrix materials (mixed matrix systems). The mixed-matrix systems preferably comprise two or three different matrix materials, particularly preferably two different matrix materials. Preferably, one of the two materials here represents a material having hole-transporting properties and the other material represents a material having electron-transporting properties. Particularly suitable matrix materials, which can be employed in combination with the semiconductor nanoparticles according to the invention as matrix components of a mixed-matrix system may be selected from those organic functional materials as described above with respect to the composition of the invention.

Preferred cathodes of the electronic device are metals having a low work function, metal alloys or multilayer structures composed of various metals, for example alkaline earth metals, alkali metals, main group metals or lanthanoids (e.g. Ca, Ba, Mg, Al, In, Mg, Yb, Sm, etc.). Additionally suitable are alloys composed of an alkali metal or alkaline earth metal and silver, for example an alloy composed of magnesium and silver. In the case of multilayer structures, in addition to the metals mentioned, it is also possible to use further metals having a relatively high work function, for example Ag or Al, in which case combinations of the metals such as Ca/Ag, Mg/Ag or Ba/Ag, for example, are generally used. It may also be preferable to introduce a thin interlayer of a material having a high dielectric constant between a metallic cathode and the organic semiconductor. Examples of useful materials for this purpose are alkali metal or alkaline earth metal fluorides, but also the corresponding oxides or carbonates (e.g. LiF, $Li_2O$, $BaF_2$, MgO, NaF, CsF, $Cs_2CO_3$, etc.). It is also possible to use lithium quinolinate (LiQ) for this purpose. The layer thickness of this layer is preferably between 0.5 and 5 nm.

Preferred anodes are materials having a high work function. Preferably, the anode has a work function of greater than 4.5 eV versus vacuum. Firstly, metals having a high redox potential are suitable for this purpose, for example Ag, Pt or Au. Secondly, metal/metal oxide electrodes (e.g. Al/Ni/$NiO_x$, Al/$PtO_x$) may also be preferred. For some applications, at least one of the electrodes has to be transparent or partly transparent in order to enable the irradiation of the organic material (organic solar cell) or the emission of light (OLED, O-laser). Preferred anode materials here are conductive mixed metal oxides. Particular preference is given to indium tin oxide (ITO) or indium zinc oxide (IZO). Preference is further given to conductive doped organic materials, especially conductive doped polymers. In addition, the anode may also consist of two or more layers, for example of an inner layer of ITO and an outer layer of a metal oxide, preferably tungsten oxide, molybdenum oxide or vanadium oxide.

The device is structured appropriately (according to the application), contact-connected and finally sealed, in order to rule out damaging effects by water and air.

In a preferred embodiment, the electronic device is characterized in that one or more layers are coated by a sublimation process. In this case, the materials are applied by vapour deposition in vacuum sublimation systems at an initial pressure of less than $10^{-5}$ mbar, preferably less than $10^{-6}$ mbar. In this case, however, it is also possible that the initial pressure is even lower, for example less than $10^{-7}$ mbar.

Preference is likewise given to an electronic device, characterized in that one or more layers are coated by the OVPD (organic vapour phase deposition) method or with the aid of a carrier gas sublimation. In this case, the materials are applied at a pressure between $10^{-5}$ mbar and 1 bar. A special case of this method is the OVJP (organic vapour jet printing) method, in which the materials are applied directly by a nozzle and thus structured (for example M. S. Arnold et al., Appl. Phys. Lett. 2008, 92, 053301).

Preference is additionally given to an electronic device, characterized in that one or more layers are produced from solution, for example by spin-coating, or by any printing method, for example screen printing, flexographic printing, nozzle printing or offset printing, but more preferably LITI (light-induced thermal imaging, thermal transfer printing) or inkjet printing. Solubility of the compounds can be improved by suitable substitution of the compounds as known to the person skilled in the art, for example by substitution with groups that increase solubility in organic solvents, such as aromatic groups (e.g. terphenyl groups) or alkyl groups.

It is further preferable that an electronic device of the invention is produced by applying one or more layers from solution and one or more layers by a sublimation method.

The electronic device according to the invention, which comprises at least one semiconductor nanoparticle or a composition of the invention as described above, is advantageous in terms of operating voltage and external quantum efficiency, as will be shown below.

Accordingly, the electronic devices comprising at least one semiconductor nanoparticle or a composition of the invention can be used in displays, as light sources in lighting applications and as light sources in medical and/or cosmetic applications (e.g. light therapy).

The invention is described in more detail below with the help of examples which are not to be considered as limiting the scope of the invention.

EXAMPLES

Working Example 1—Preparation of Compound (1)

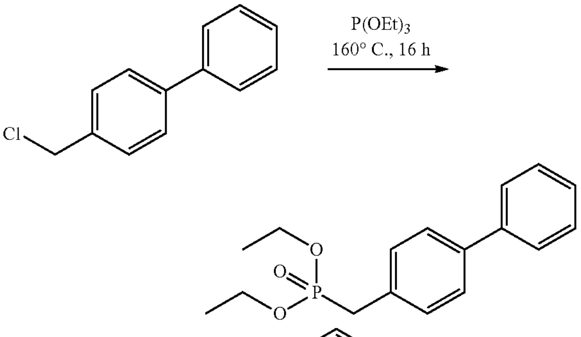

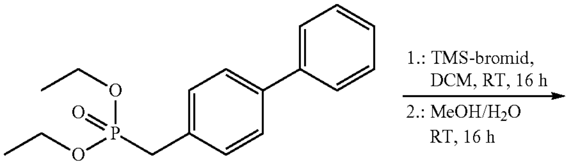

-continued

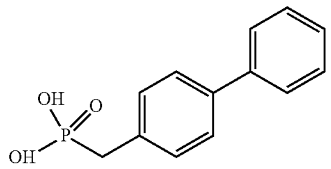

1. Biphenyl-4-ylmethyl Phosphonic Acid Diethyl Ester 2.3 g of 4-phenylbenzyl chloride (98%, Sigma-Aldrich) is dissolved in 48.52 g of triethylphosphite (98%, Sigma-Aldrich) in a 100 mL, 3-neck round bottom flask, connected to a condenser, under argon atmosphere. The system is heated to 160° C. for 26 hours. The product formed is then separated by column chromatography using silica as adsorbent and ethylacetate and heptane as eluents.

2. Biphenyl-4-ylmethyl Phosphonic Acid (Compound (1))

2.0 g of the above obtained product, biphenyl-4-ylmethyl phosphonic acid diethyl ester (96%, determined by gas chromatography-mass spectroscopy (GCMS) on commercially available equipment (HP 6890 Series, 5973 detector)) is mixed with 3.05 g of bromotrimethylsilane in 20 mL of dichloromethane in a 100 mL, 3-neck round bottom flask, connected to a condenser, under argon atmosphere. The mixture is mixed for 16 hours at room temperature. Then the solvent is evaporated using a rotating evaporator. The dried residue is dissolved in methanol (10% water, Sigma Aldrich) and mixed for 16 hours at room temperature, under argon. The suspension is filtrated over a paper filter and washed twice with methanol to obtain the product (yield: 62%).

Working Example 2—Preparation of Compound (2)

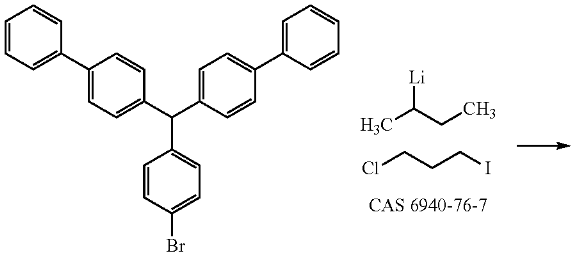

CAS 499128-71-1

-continued

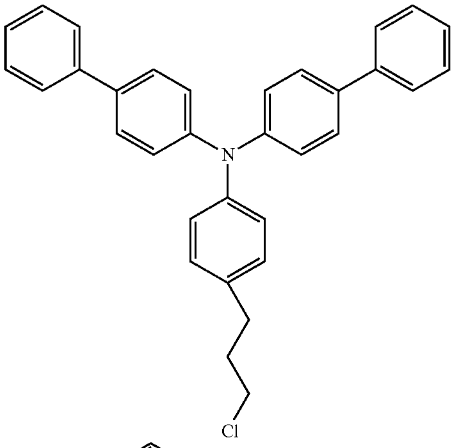

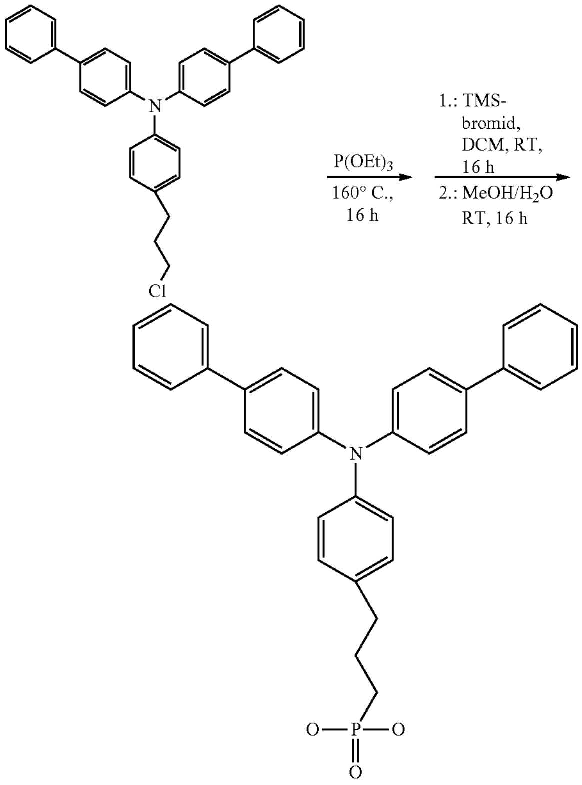

1. Bis-biphenyl-4-yl-[4-(3-chloro-propyl)-phenyl]-amine

In a glove box, 6.48 mL of tert-butyllithium (t-BuLi), 1.7 M solution in pentane (Sigma-Aldrich), is put in a dropping funnel. 2.5 g of bis-biphenyl-4-yl-(4-bromo-phenyl)-amine (Merck) is dissolved in dried tetrahydrofuran (THF) in a 100 mL 3-neck flask and then cooled down to −78° C. using a dry ice bath (Aceton). The dropping funnel with t-BuLi is taken out from glove box and connected to the flask. The t-BuLi is slowly dropped directly into the solution. Afterwards the funnel is carefully rinsed with dry THF. The solution is stirred for 1 hour at −78° C.

Then, 0.62 mL of 1-bromo-3-chloropropan is slowly added with an argon-flushed syringe to the reaction. The solution is let to heat back to room temperature and then further stirred overnight under argon. Afterwards, the mixture is cooled down again to 0° C. in an ice bath and 10 mL $H_2O$ are slowly added with a syringe. Afterwards 5 mL 1M HCl are slowly added. Additional 5 mL 1M HCl are added after the solution became greenish. The ice bath is removed and the mixture is stirred until it reaches room temperature (RT). The reaction product has two phases. The organic phase is separated and the aqueous phase is extracted with dichloromethane (3×15 mL) and dried with $MgSO_4$.

2. 3-[4-(Bis-biphenyl-4-yl-amino)-phenyl]propylp-phosphonic Acid Diethyl Ester 1.34 g bis-biphenyl-4-yl-[4-(3-chloro-propyl)-phenyl]-amine (97%) are mixed with 50 mL TEP in an one neck flask and stirred for 72 hours at 160° C. under argon.

3. {3-[4-(Bis-biphenyl-4-yl-amino)-phenyl]-propyl}-phosphonic Acid (Compound (2))

0.77 g of 3-[4-(Bis-biphenyl-4-yl-amino)-phenyl]-propyl}-phosphonic acid diethyl ester are dissolved in 20 mL dichlomethane and mixed with 0.63 g (0.55 mL) bromotrimethyl silane (3 eq) under argon and stirred at room temperature for 12 hours. Methanol (10% $H_2O$) is added directly to the solution, which becomes whitish. The mixture is stirred at room temperature under argon overnight. Afterwards, the mixture is evaporated and a yellowish gel is formed. The gel is recrystallized in 5 mL acetonitrile, to obtain a white slightly yellowish wax and a yellowish supernatant. The supernatant is removed and the wax washed twice with little amounts of acetonitrile. The wax is recrystallized in 3 mL ethanol. A white wax is received. 5 mL heptane are added and the wax is resuspended at room temperature, filtrated (washed 2× with heptane) and dried in a vacuum chamber. A white slightly greenish solid is received (yield: 38%).

The synthesis of further compounds (3), (4), (6) and (7)—as shown in Table 2 below—is carried out analogously:

TABLE 2

| compound | Product | Yield |
|---|---|---|
| (3) | 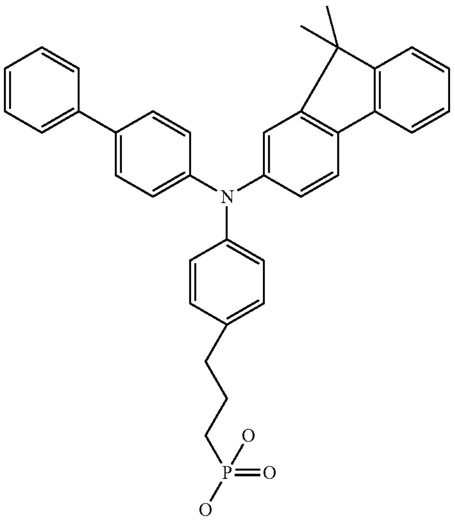 [SMILES: CC1(C)c2ccccc2-c2ccc(N(c3ccc(CCCP(=O)(O)O)cc3)c3ccc(-c4ccccc4)cc3)cc21] | 70% |

TABLE 2-continued

| compound | Product | Yield |
|---|---|---|
| (4) | 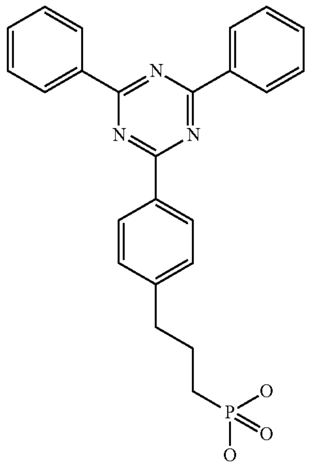 [SMILES: O=P(O)(O)CCCc1ccc(-c2nc(-c3ccccc3)nc(-c3ccccc3)n2)cc1] | 35% |
| (6) | 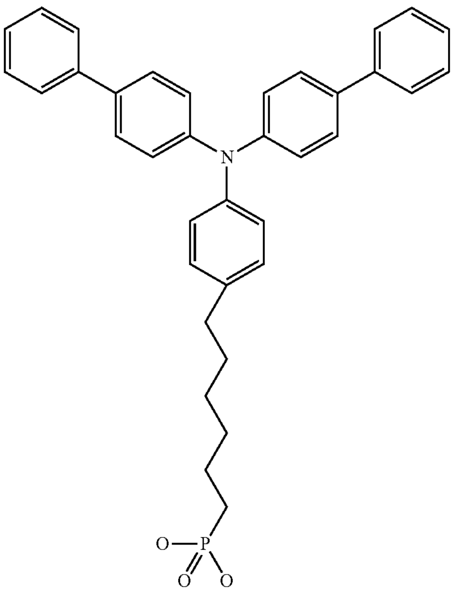 [SMILES: O=P(O)(O)CCCCCCc1ccc(N(c2ccc(-c3ccccc3)cc2)c2ccc(-c3ccccc3)cc2)cc1] | 65% |

TABLE 2-continued

| compound | Product | Yield |
|---|---|---|
| (7) | 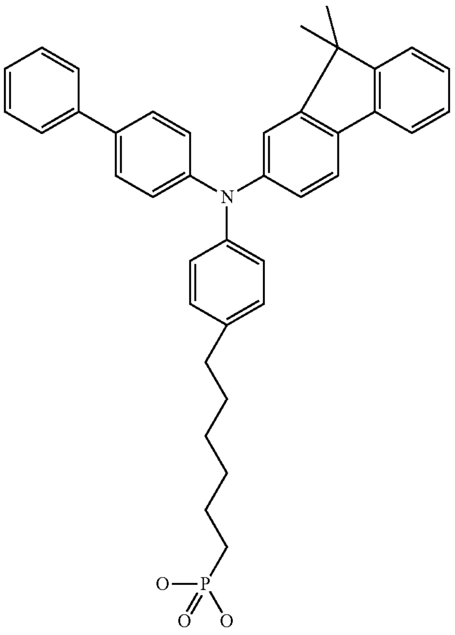 [SMILES: CC1(C)c2ccccc2-c2ccc(N(c3ccc(CCCCCCP(=O)(O)O)cc3)c3ccc(-c4ccccc4)cc3)cc21] | 67% |
| (31) | 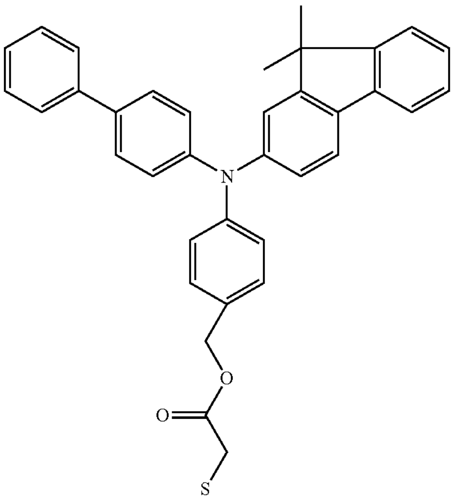 [SMILES: CC1(C)c2ccccc2-c2ccc(N(c3ccc(COC(=O)CS)cc3)c3ccc(-c4ccccc4)cc3)cc21] | 80% |

TABLE 2-continued

| compound | Product | Yield |
|---|---|---|
| (33) | 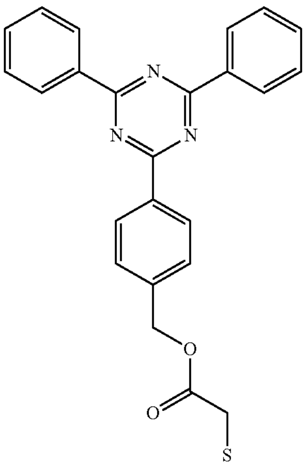 [SMILES: O=C(CS)OCc1ccc(-c2nc(-c3ccccc3)nc(-c3ccccc3)n2)cc1] | 30% |
| (35) | 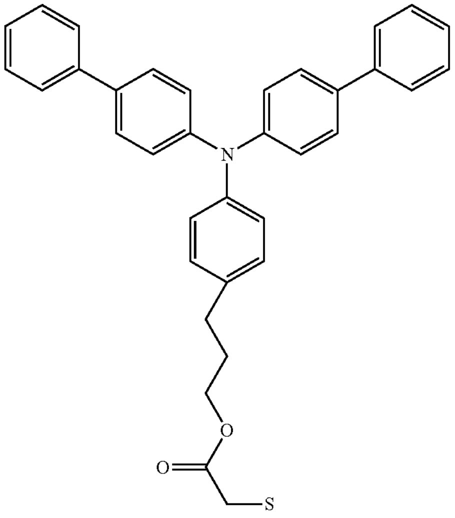 [SMILES: O=C(CS)OCCCc1ccc(N(c2ccc(-c3ccccc3)cc2)c2ccc(-c3ccccc3)cc2)cc1] | 80% |

Working Example 3—Preparation of Semiconductor Nanoparticle

InP/ZnS core/shell nanoparticles were synthesized in a similar method as described in: Hussain et. al. *ChemPhysChem,* 2009, 10, 1466-1470 5 mL of a InP/ZnS core/shell nanoparticles (PL emission peak 625 nm) containing solution (50 mg/mL in toluene) are mixed with 0.25 g of a replacing surface ligand (i.e., compound (2) of working example 2) and stirred overnight at 50° C. under argon atmosphere. The mixture is then transferred into a centrifuge vial and 5 mL dried methanol is added. After that, the mixture is centrifuged at 4000 rpm for 5 minutes under argon. Afterwards, the colorless supernatant is removed and the red precipitation is suspended in 5 mL dried toluene.

Similar procedures can be used for the other ligands according to the invention. Quantities of the added ligand are calculated based on molar amounts.

Working Example 4—Fabrication of Solution Processed OLED (Device E1)

The production of solution-based OLEDs has already been described many times in the literature, for example in WO 2004/037887 and WO 2010/097155. The process is adapted to the circumstances described below (layer-thickness variation, materials).

The inventive material combinations are used in the following layer sequence:

substrate,
ITO (50 nm),
Buffer (20 nm),
hole transport layer (20 nm),
emission layer (EML) (30 nm),
electron-transport layer (ETL) (50 nm),
electron injection layer (EIL) (3 nm),
cathode (Al) (100 nm).

Glass plates coated with structured ITO (indium tin oxide) in a thickness of 50 nm serve as substrate. These are coated with the buffer (PEDOT) Clevios P VP Al 4083 (Heraeus Clevios GmbH, Leverkusen) by spin coating. The spin coating of the buffer is carried out from water in air. The layer is subsequently dried by heating at 180° C. for 10 minutes. The hole transport layers and the emission layers are applied to the glass plates coated in this way.

For the hole-transport layer, the polymer of the structure shown in Table 3 is used, which is synthesised in accordance with WO 2010/097155. The polymer is dissolved in toluene, so that the solution has a solid content of about 5 g/L, in order to prepare a 20 nm thick layer. The layer is applied by spin coating in an argon atmosphere, and dried by heating at 220° C. for 30 min.

For the emission layer, red light emitting InP/ZnS nanoparticles according to the invention, that is, quantum dots having attach to their surface ligands according to the invention, are used, which are dissolved in toluene. The solids content of such solutions is about 15 mg/mL, in order to prepare a 30 nm thick layer. The layer is applied by spin coating in an argon atmosphere, and dried by heating at 120° C. for 10 minutes.

TABLE 4

| Chemical structures of the materials used for thermally evaporated layers in OLEDs |
|---|
| 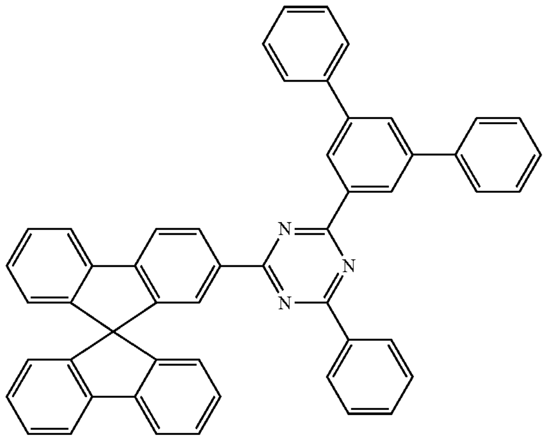 |
| ETL |
| 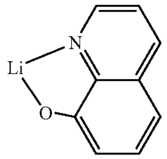 |
| EIL |

TABLE 3

| Structural formulae of the additional materials used for the solution processed layers in OLEDs |
|---|
| 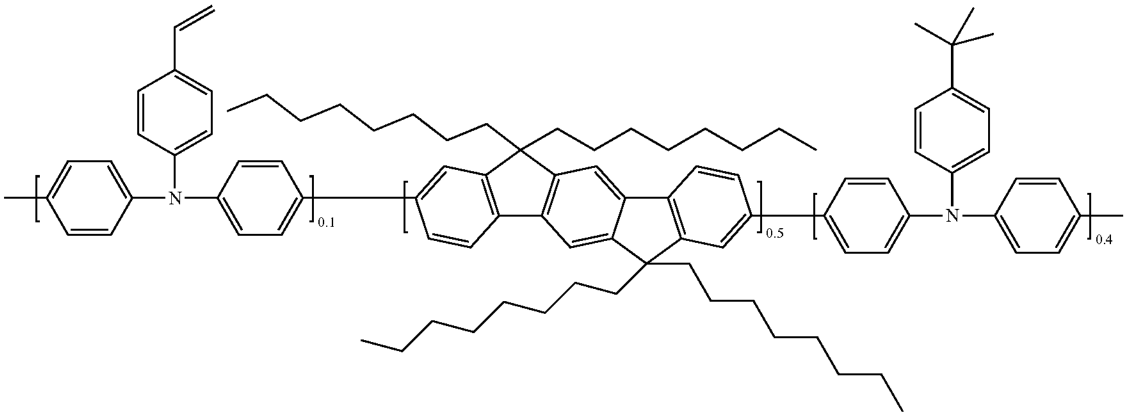 |
| HTL |

The materials for the electron-transport layer and the electron injection layer are likewise applied by thermal vapour deposition in a vacuum chamber and are shown in Table 4. The electron-transport layer consists of the material ETL and the electron injection layer consists of EIL. The cathode is formed by the thermal evaporation of an aluminium layer with a thickness of 100 nm.

Comparative Example 1—Fabrication of Solution Processed OLED (Device V1)

A solution-based OLED is prepared in the same way as described in working example 4 above, using the same compounds/materials except that state-of-the-art red light emitting semiconductor nanoparticles, that is, QDs covered with common alkyl ligands, are used for preparation of the emissive layer.

Working Example 5—Device Characterization

The OLEDs are characterised by standard methods. For this purpose, the electroluminescence spectra and the external quantum efficiency (EQE, measured in %) are determined from current/voltage/luminance characteristic lines (IUL characteristic lines) assuming a Lambertian emission profile. The electroluminescence (EL) spectra are recorded at a luminous density of 100 $cd/m^2$ and the CIE 1931 x and y coordinates are then calculated from the EL spectrum. The device data of the OLEDs prepared according to working example 4 and comparative example 1 is summarized in Table 5. In the following section, the examples are described in more detail to show the advantages of the OLEDs of the invention.

Use of InP/ZnS Nanoparticles According to the Invention as Emitting Material in OLEDs The InP/ZnS nanoparticles according to the invention are especially suitable as emitting material in an OLED device. The properties of the OLEDs prepared are summarised in Table 5. Example E1 shows properties of OLEDs containing materials of the present invention.

TABLE 5

Device data of solution processed OLEDs

| Example | Voltage @ 10 $mA/cm^2$ V | EQE @ 10 $cd/m^2$ % | CIE x | CIE y |
|---|---|---|---|---|
| V1 | 7.6 | 3.0 | 0.62 | 0.36 |
| E1 | 3.3 | 4.5 | 0.62 | 0.36 |

As can be seen from the data shown in Table 5, an OLED using in the emissive layer the semiconductor nanoparticle according to the invention (E1), that is, quantum dots having attached to their surface ligands according to the invention, in this example structure (35) provides a significantly improvement in lower driving voltage and increased EQE compared to the state-of-the-art (V1, i.e. QDs covered with common carboxylic and thiol alkyl ligands, as described in: Hussain et. al. *ChemPhysChem,* 2009, 10, 1466-1470).

The invention claimed is:

1. A compound comprising, in the given order, an anchor group, AG, capable of binding to a surface of a semiconductor nanoparticle, followed by an electronically inert and conjugating interrupting linker group, L, followed by an organic functional group, FG, wherein group FG is an electron transporting group selected from the following groups (ET-22)

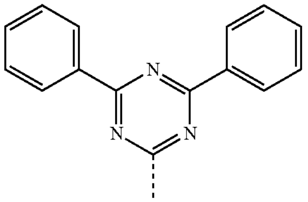

-continued (ET-23)

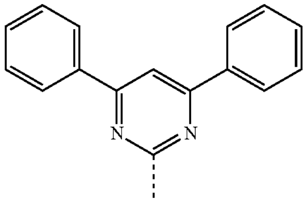

(ET-24)

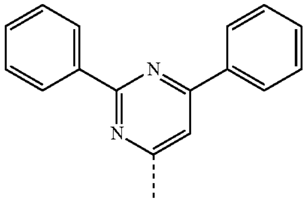

(ET-25)

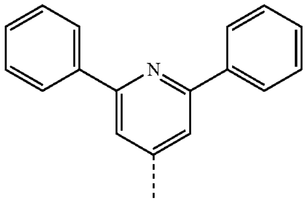

(ET-26)

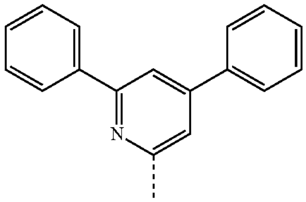

(ET-27)

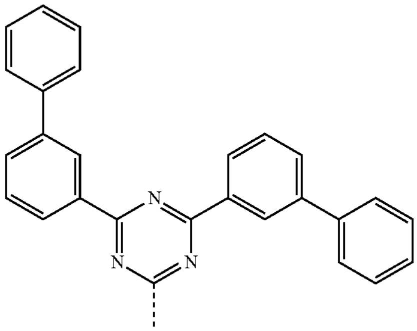

(ET-28)

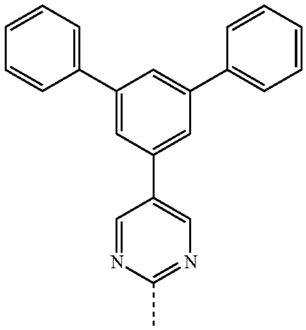

-continued
(ET-29)
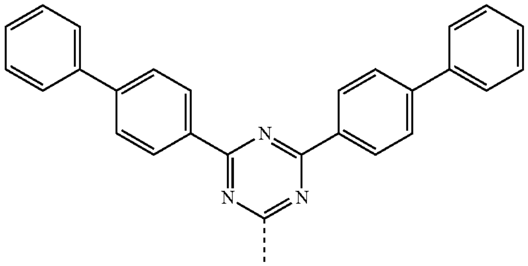
(ET-30)
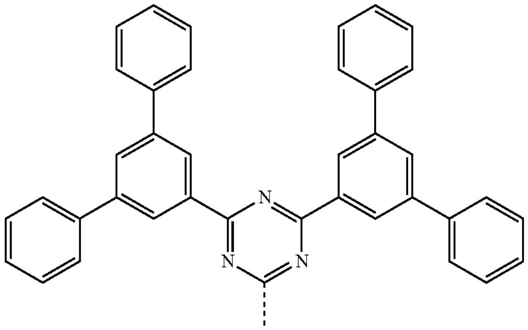
(ET-31)
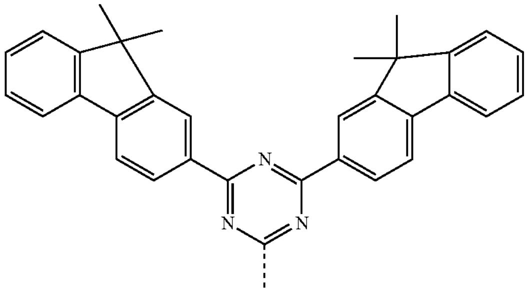
(ET-32)
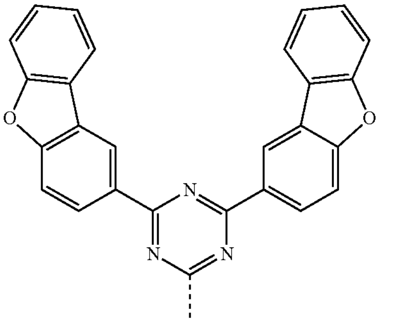
(ET-33)
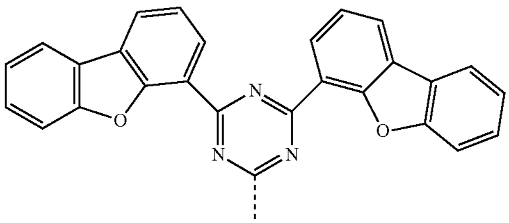
-continued
(ET-34)
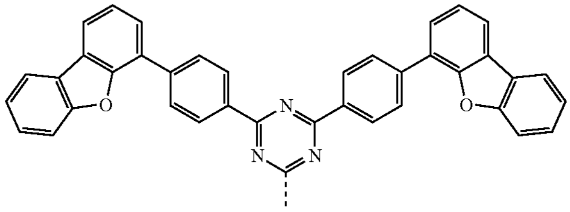
(ET-35)
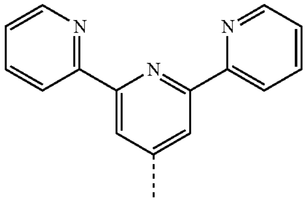
(ET-36)
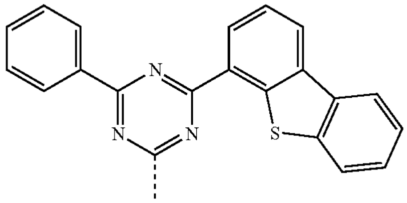
(ET-37)
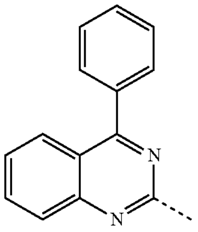
(ET-38)
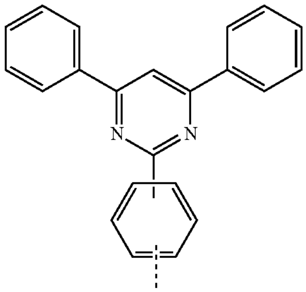
(ET-39)
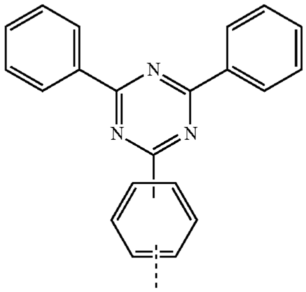

-continued
(ET-40)
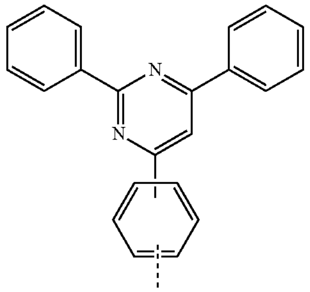
(ET-41)
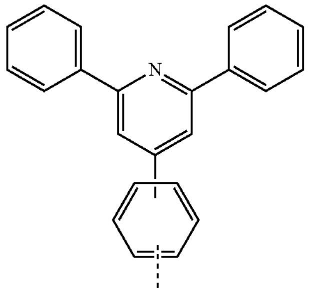
(ET-42)
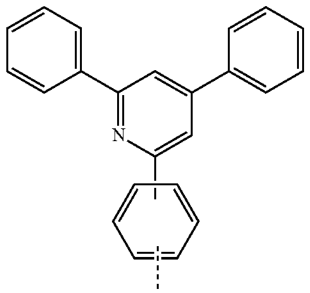
(ET-43)
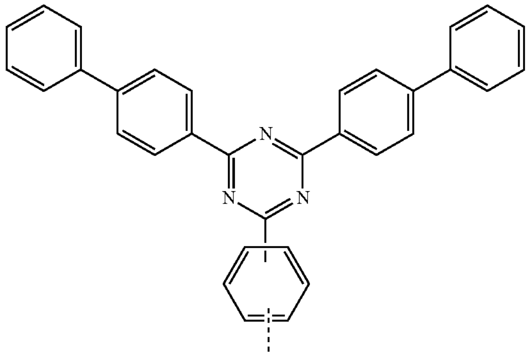
-continued
(ET-44)
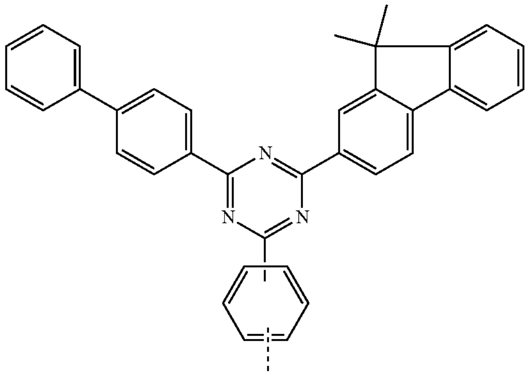
(ET-45)
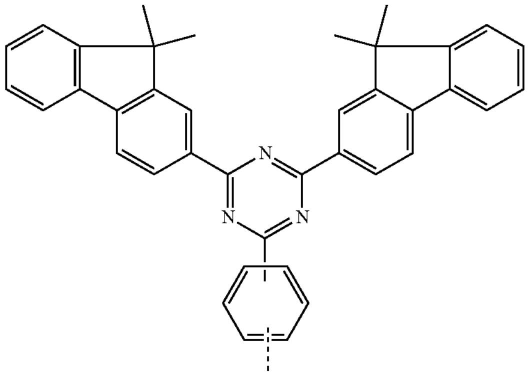
(ET-46)
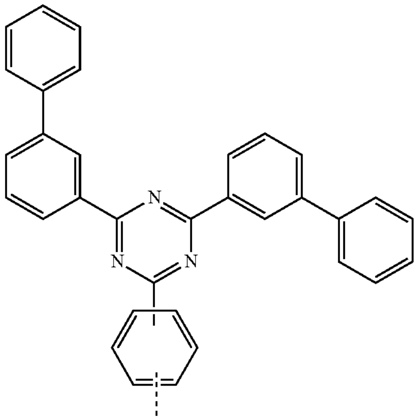
(ET-47)
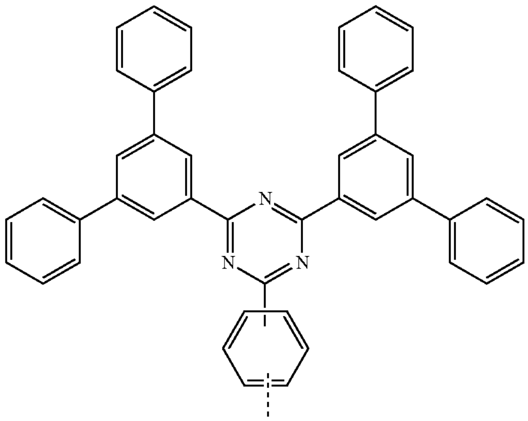

-continued (ET-48)

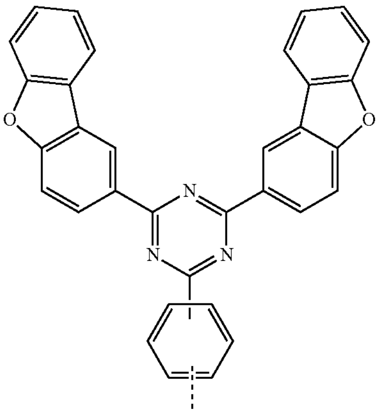

(ET-49)

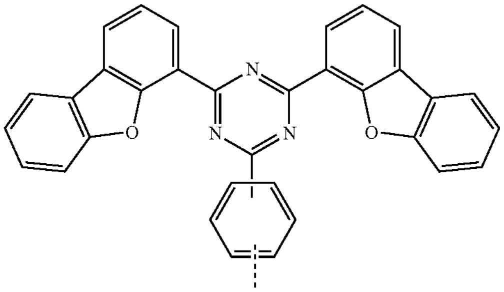

(ET-50)

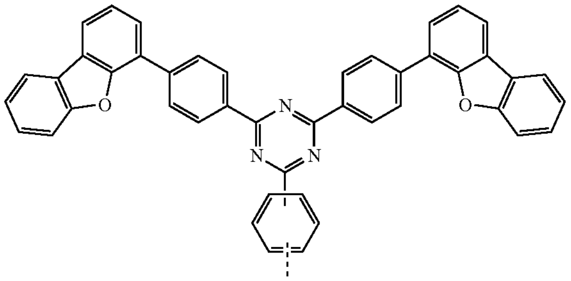

(ET-51)

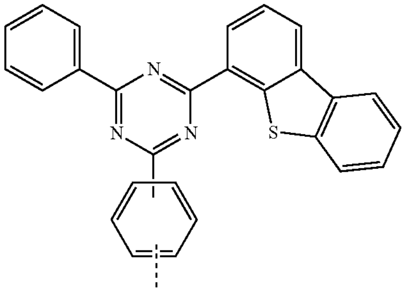

wherein the dashed line represents the bonding position to the linker group, wherein the compound has a molecular weight of 1000 g/mol or less, and wherein the anchor group, AG, is selected from the group consisting of thiols or salts thereof, phosphonic acids or salts thereof, carboxylic acids or salts thereof, selenols or salts thereof, sulfinic acids or salts thereof, mercaptoesters or salts thereof, carbodithioic acids or salts thereof, boronic acids or salts thereof, and phosphines.

2. The compound according to claim 1, wherein the anchor group, AG, is selected from the group consisting of thiols or salts thereof, phosphonic acids or salts thereof, carboxylic acids or salts thereof, mercaptoesters or salts thereof, and boronic acids or salts thereof.

3. The compound according to claim 1, wherein the linker group, L, is selected from the group consisting of a straight-chain alkylene group having 1 to 20 C atoms, or a cyclic or branched alkylene group having 3 to 20 C atoms, wherein one or more non adjacent methylene groups can each be replaced by —O—, —S—, —C(═O)O—, —C(═S)S—, aromatic rings, or heteroaromatic rings.

4. The compound according to claim 1, wherein the compound is of formula (1)

formula (1)

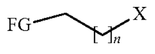

wherein the following applies to the symbols and indices wherein X is the anchor group, AG, and wherein X is selected from —SH, —C(═O)OH, —$NH_2$, —P(═O)(OH)(OH), —SeH, —P(R'R"), —$S^-Y^+$, —S(═O)OH, —S(═O)$O^-Y^+$, —C(═O)$O^-Y^+$, —OC(═O)R'''SH, —OC(═O)R'''$S^-Y^+$, —P(═O)(OH)($O^-Y^+$), —$Se^-Y^+$, —C(═S)SH, —C(═S)$S^-Y^+$, —$B(OH)_2$, —B(OH)$O^-Y^+$, —$B(O^-Y^+)_2$, —$B(O^-)_2$ $Z^{2+}$, —P(═O)($O^-Y^+$)($O^-Y^+$) or —P(═O)($O^-$)($O^-$) $Z^{2+}$;

Y+ is selected from $Na^+$, $K^+$, $Li^+$, ½$Cd^{2+}$, ½$Zn^{2+}$, ½$Mg^{2+}$, ½$Ca^{2+}$, ½$Sr^{2+}$, ⅓$In^{3+}$, ⅓$Ga^{3+}$;

$Z^{2+}$ is $Cd^{2+}$, $Zn^{2+}$, $Mg^{2+}$, $Ca^{2+}$, $Sr^{2+}$;

R',R" are, identically or differently, selected from H, linear or branched alkyl groups having 1 to 20 C atoms;

R''' is selected from linear or branched alkyl groups having 1 to 10 C atoms; and n is an integer from 0 to 20.

5. A semiconductor nanoparticle comprising a core, one or more shell layers, and at least one ligand that is attached to the outermost surface of the one or more shell layers, wherein the at least one ligand is a compound according to claim 1.

6. A composition comprising:

at least one first semiconductor nanoparticle according to claim 5, and at least one second semiconductor nanoparticle, or said at least one first semiconductor nanoparticle and at least one further organic functional material selected from electron injecting materials, electron transporting materials, hole blocking materials, n-dopants, host materials, matrix materials, wide band gap materials, fluorescent emitter materials, delayed fluorescent materials, phosphorescent emitter materials, electron blocking materials, hole transporting materials, hole injecting materials, and p-dopants.

7. A composition comprising at least one first semiconductor nanoparticle according to claim 5, at least one second semiconductor nanoparticle and at least one further organic functional material selected from electron injecting materials, electron transporting materials, hole blocking materials, n-dopants, host materials, matrix materials, wide band gap materials, fluorescent emitter materials, delayed fluorescent materials, phosphorescent emitter materials, electron blocking materials, hole transport materials, hole injecting materials, and p-dopants.

8. A method for preparation of a semiconductor nanoparticle according to claim 5, comprising providing a semiconductor nanoparticle comprising a core and one or more shell layers into a solvent together with said compound to get a mixture.

9. An electronic device comprising at least one semiconductor nanoparticle according to claim 5 or a composition comprising said at least one first semiconductor nanoparticle and at least one second semiconductor nanoparticle, or comprising said at least one first semiconductor nanoparticle and at least one further organic functional material selected from electron injecting materials, electron transporting materials, hole blocking materials, n-dopants, host materials, matrix materials, wide band gap materials, fluorescent emitter materials, delayed fluorescent materials, phosphorescent emitter materials, electron blocking materials, hole transporting materials, hole injecting materials, and p-dopants.

10. The electronic device according to claim 9, wherein the device is an electroluminescent device.

11. The electronic device according to claim 9, wherein the device is an electroluminescent device that comprises the semiconductor nanoparticle or the composition in the emissive layer.

12. A semiconductor nanoparticle comprising a core, one or more shell layers and at least one ligand that is attached to the outermost surface of the one or more shell layers, wherein the semiconductor nanoparticle comprises at least two different ligands, wherein the ligands are selected from the compounds according to claim 1.

13. The semiconductor nanoparticle according to claim 12, wherein the semiconductor nanoparticle comprises a first ligand and a second ligand, and wherein the first ligand comprises an organic functional group selected from an electron transporting group and wherein the second ligand comprises an organic functional group selected from a hole transporting group.

14. A composition comprising at least one first semiconductor nanoparticle and at least one second semiconductor nanoparticle, each of said nanoparticles comprises a core, one or more shell layers, and at least one ligand that is attached to the outermost surface of the one or more shell layers, wherein the at least one ligand is a compound according to claim 1, and wherein the at least one second semiconductor nanoparticle and the at least one first semiconductor nanoparticle differ from each other.

15. The composition according to claim 14, wherein the at least one first semiconductor nanoparticle further comprises at least one ligand attached to its outermost surface which comprises a delayed fluorescent group.

16. The composition according to claim 14, wherein the at least one first semiconductor nanoparticle further comprises at least one ligand attached to its outermost surface which comprises a phosphorescent group.

17. A formulation comprising:

a compound according to claim 1; or a semiconductor nanoparticle comprising a core, one or more shell layers and at least one ligand that is attached to the outermost surface of the one or more shell layers, characterized in that the at least one ligand is selected from said compound; or a composition comprising said semiconductor nanoparticle and at least one second semiconductor nanoparticle, or comprising semiconductor nanoparticle and at least one further organic functional material selected from electron injecting materials, electron transporting materials, hole blocking materials, n-dopants, host materials, matrix materials, wide band gap materials, fluorescent emitter materials, delayed fluorescent materials, phosphorescent emitter materials, electron blocking materials, hole transporting materials, hole injecting materials, and p-dopants; and at least one solvent.

* * * * *